United States Patent [19]
Kool

[11] Patent Number: 5,683,874
[45] Date of Patent: Nov. 4, 1997

[54] SINGLE-STRANDED CIRCULAR OLIGONUCLEOTIDES CAPABLE OF FORMING A TRIPLEX WITH A TARGET SEQUENCE

[75] Inventor: Eric T. Kool, Rochester, N.Y.

[73] Assignee: Research Corporation Technologies, Inc., Tucson, Ariz.

[21] Appl. No.: 413,813

[22] Filed: Mar. 30, 1995

Related U.S. Application Data

[63] Continuation-in-part of Ser. No. 4,800, Jan. 11, 1993, Pat. No. 5,426,180, which is a continuation-in-part of Ser. No. 859,922, Mar. 26, 1992, abandoned, which is a continuation-in-part of Ser. No. 675,843, Mar. 27, 1991, abandoned.

[51] Int. Cl.$^6$ .............. C07H 21/04; C12Q 1/68
[52] U.S. Cl. .............. 435/6; 514/44; 536/23.1; 536/24.3; 536/24.5
[58] Field of Search .............. 435/6, 810; 514/44; 536/23.1, 24.3, 24.5

[56] References Cited

U.S. PATENT DOCUMENTS

| | | | |
|---|---|---|---|
| 4,766,062 | 8/1988 | Diamond et al. | 435/6 |
| 4,777,129 | 10/1988 | Dattagupta et al. | 435/6 |
| 5,176,996 | 1/1993 | Hogan et al. | 435/6 |
| 5,473,060 | 12/1995 | Gryaznov et al. | 536/24.3 |

FOREIGN PATENT DOCUMENTS

| | | |
|---|---|---|
| 0375408 | 6/1990 | European Pat. Off. |
| 9106626 | 5/1991 | WIPO |
| 9201813 | 2/1992 | WIPO |
| WO92/1784 | 10/1992 | WIPO |
| WO92/19732 | 11/1992 | WIPO |
| WO94/17086 | 8/1994 | WIPO |

OTHER PUBLICATIONS

Gura, *Science* 270, 575–577 (1995).
Prakash et al., *J. Am. Chem. Soc.* 114, 3523–3527 (1992).
Kool, *J. Am. Chem. Soc.* 113, 6265–6266 (1991).
Prakash et al., *J. Chem. Soc., Chem. Commun.*, 1161–1163 (1991).
Agrawal, et al (1988) "Oligodeoxynucleoside Phosphoramidates and Phosphorothioates as Inhibitors of Human Immunodeficiency Virus," *Proc. Natl. Acad. Sci. USA* 85:7079–7083.

(List continued on next page.)

*Primary Examiner*—Kenneth R. Horlick
*Attorney, Agent, or Firm*—Scully, Scott, Murphy & Presser

[57] ABSTRACT

The present invention provides single-stranded circular oligonucleotides each with at least one parallel binding (P) domain and/or at least one corresponding anti-parallel binding (AP) domain separated from each other by loop domains. When more than one P or AP domain is included in a circular oligonucleotide of the present invention, the additional P or AP domains can constitute loop domains for a pair of corresponding P and AP domains, and vice versa. The present invention further provides single-stranded circular oligonucleotides with at least one Hoogsten antiparallel (HAP) domain. Each P, AP and HAP domain has sufficient complementarity to bind to one strand of a defined nucleic acid target wherein the P domain binds in a parallel manner to the target and the HAP or AP domain binds in an anti-parallel manner to the target. Moreover, the present single-stranded circular oligonucleotides can bind to both single-stranded and double-stranded target nucleic acids. The present invention also provides methods of making and using these oligonucleotides as well as kits and pharmaceutical compositions containing these oligonucleotides.

50 Claims, 21 Drawing Sheets

OTHER PUBLICATIONS

Baumann, et al (1988), "Interaction of DNA Hairpin Loops and a Complementary Strand by a Triplet of Base Pairs," *Biochem. Biophys. Res. Commun.* 157:986–991.

Cooney, et al (1988), "Site–Specific Oligonucleotide Binding Represses Transcription of the Human c–myc Gene in Vitro," *Science* 241:456–459.

Durand et al (1992), "Triplex–Helix Formation by an Oligonucleotide Containing One $(dA)_{12}$ and Two $(dT)_{12}$ Sequences Bridged by Two Hexaethylene Glycol Chains," *Biochemistry* 31:9197–9204.

Erie, et al (1987), "A Dumbbell–Shaped, Double–Hairpin Structure of DNA: A Thermodynamic Investigation," *Biochemistry* 26:7150–7159.

Erie, et al (1989), "Melting Behavior of a Covalently Closed, Single–Stranded, Circular DNA," *Biochemistry* 28:268–273.

Giovannangeli, et al (1991), "Single–Stranded DNA as a Target for Triple–Helix Formation," *J. Am. Chem. Soc.* 113:7775–7777.

Goodchild, et al (1988), "Inhibition of Human Immunodeficiency Virus Replication by Antisense Oligodeoxynucleotides," *Proc. Natl. Acad. Sci. USA* 85:5507–5511.

Griffin et al (1989), "Recognition of Thymine–Adenine Base Pairs by Guanine In a Pyrimidine Triple Helix Motif," *Science* 245:967–971.

Lee, et al (1984), "Poly(pyrimidine)–Poly(purine) Synthetic DNA's Containing 5–methylcytosine Form Stable Triplexes at Neutral pH," *Nucleic Acids Research* 12:6603–6614.

Luebke, et al (1989), "Nonenzymatic Ligation of Oligodeoxyribonucleotides on a Duplex DNA Template by Triple–Helix Formation," *J. Am. Chem. Soc.* 111:8733–8735.

Maher, III et al (1991), "Oligonucleotide–Directed DNA Triple–Helix Formation: An Approach to Artificial Repressors?" *Antisense Research and Development* 1:277–281.

Mendel, et al (1987), "Hoogsteen Base Pairs Proximal and Distal to Echinomycin Binding Sites on DNA," *Proc. Natl. Acad. Sci. USA* 84:910–914.

Ono, et al (1991), "DNA Triplex Formation of Oligonucleotide Analogues Consisting of Linker Groups and Octamer Segments that Have Opposite Sugar–Phosphate Backbone Polarities," *Biochemistry* 30:9914–9921.

Povsic, et al (1989), "Triple Helix Formation by Oligonucleotides on DNA Extended to the Physiological pH Range," *J. Am. Chem. Soc.* 111:3059–3061.

Riordan, et al (1991), "Oligonucleotide–Based Therapeutics," *Nature* 350:442–443.

Uhlmann, et al (1990), "Antisense Oligonucleotides: A New Therapeutic Principle," *Chemical Reviews* 90:543–584.

Vroom, et al (1988), "Synthesis of Cyclic Oligonucleotides by a Modified Phosphotriester Approach," *Nucleic Acids Research* 18:4607–4620.

Xodo, et al (1990), "Spectroscopic and Calorimetric Investigation on the DNA Triplex Formed by d(CTCTTCTTTCTTTTCTTTCTTCTC) and d(GAGAAGAAAGA) at Acidic pH," *Nucleic Acids Research* 18:3557–3564.

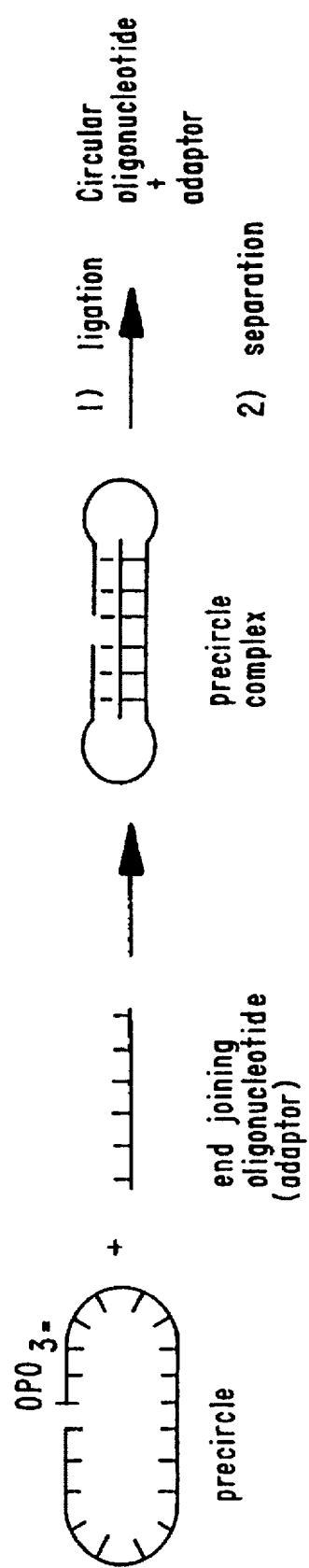

Precircles (1-3), Targets (4-5), Linear Oligonucleotides (9)
and Circles (6-8) used in Experiments 1  5'-TTTTTTCACACTTTTTTTTTTTTCACACTTTTTT (SEQ ID NO: 5)
2  5'-TCTTTCCACACCTTTCTTTTCTTCACACTTCTTT (SEQ ID NO: 6)
3  5'-TTTCTTCACACTTCTTTTCTTTCCACACCTTTCT (SEQ ID NO: 7)
4  5'-AAAAAAAAAAAA (SEQ ID NO: 8)
5  5'-AAGAAAAGAAAG (SEQ ID NO: 9)

6
```
        →    1
      TTTTTTTTTTTT
     C            C
    A              A
    C              C
    A              A
     C            C
      TTTTTTTTTTTT
```
(SEQ ID NO: 5)

7
```
        →    1
      CTTCTTTTCTTTCC
     A              A
    C                C
    A                A
      CTTCTTTTCTTTCC
```
(SEQ ID NO: 6)

8
```
           →
      CTTCTTTTCTTTCC
     A              A
    C                C
    A                A
      CTTCTTTTCTTTCC
           1
```
(SEQ ID NO: 7)

FIG.2A 9  5'-CTTTCTTTTCTT  (SEQ ID NO: 10)

10  5'-AAAAAAAAAAA  (SEQ ID NO: 11)

11  5'-AAGAAAGAAAAG  (SEQ ID NO: 12)

12  5'-AAGAAAGAAAAG  (SEQ ID NO: 13)

13  (SEQ ID NO: 14)

```
         1→
      TTCTTCTCTTTC
    C              C
   A                A
  C                  C
  A                  A
   C                C
    C              C
      TTCTTATCTTTC
```

14  5'-AAAAAAAAAAA  
   3'-TTTTTTTTTTT  (SEQ ID NO: 15)

15 5'-TCTCTTTTTTTTTTCTCTCTCTTTTTTTTTTTCTC  
  (SEQ ID NO:16)

16  5'-AAAGAGAGAGAAA  (SEQ ID NO:17)

17  (SEQ ID NO:18)

```
              1→
           TTTTTTTTT
         T           T
         C           C
         T           T
         C           C
         T           T
         C           C
         T           T
         C           C
         T           T
           TTTTTTTTT
```

18  5'-AGAGAGAGA  (SEQ ID NO:19)

19  5'-AAAAAAAAA  (SEQ ID NO:20)

20 5'-CACAAGAGAGAGAATCCCTAAAAAAAAAAACAC (SEQ ID NO:21)

21  5'-TCTCTCTCT  (SEQ ID NO:22)

22  5'-TTTTTTTT  (SEQ ID NO:23)

FIG.2B 0 1 8 24 48 72h
LINEAR 34mer 0 1 8 24 48 72h
CIRCULAR 34mer

SINGLE-STRANDED CIRCULAR OLIGONUCLEOTIDES CAPABLE OF FORMING A TRIPLEX WITH A TARGET SEQUENCE

The present application is a continuation-in-part of application U.S. Ser. No. 08/004,800 filed Jan. 11, 1993, U.S. Pat. No. 5,426,180 which is a continuation-in-part of U.S. Ser. No. 07/859,922 filed Mar. 26, 1992, now abandoned, which is a continuation-in-part of U.S. Ser. No. 07/675,843 filed Mar. 27, 1991, now abandoned.

This invention was made with United States government support under grant number GM-46625 awarded by the National Institutes of Health. The United States government has certain rights in the invention.

FIELD OF THE INVENTION

The present invention provides single-stranded circular oligonucleotides capable of binding to a target DNA or RNA and thereby regulating DNA replication, RNA transcription, protein translation, and other processes involving nucleic acid templates. Furthermore, circular oligonucleotides can be labeled for use as probes to detect or isolate a target nucleic acid. Moreover, circular oligonucleotides are resistant to exonucleases and thus superior to linear oligonucleotides for diagnostic and therapeutic applications.

BACKGROUND OF THE INVENTION

An oligonucleotide binds to a target nucleic acid by forming hydrogen bonds between bases in the target and the oligonucleotide. Common B DNA has conventional adenine-thymine (A-T) and guanine-cytosine (G-C) Watson and Crick base pairs with two and three hydrogen bonds, respectively. Conventional hybridization technology is based upon the capability of sequence-specific DNA or RNA probes to bind to a target nucleic acid via Watson-Crick hydrogen bonds. However, other types of hydrogen bonding patterns are known wherein some atoms of a base which are not involved in Watson-Crick base pairing can form hydrogen bonds to another nucleotide. For example, thymine (T) can bind to an A-T Watson-Crick base pair via hydrogen bonds to the adenine, thereby forming a T-AT base triad. Hoogsteen (1959, *Acta Crystallography* 12:822) first described the alternate hydrogen bonds present in T-AT and C-GC base triads. More recently, G-TA base triads, wherein guanine can hydrogen bond with a central thymine, have been observed (Griffin et al., 1989, *Science* 245:967–971). If an oligonucleotide could bind to a target with both Watson-Crick and alternate hydrogen bonds an extremely stable complex would form that would have a variety of in vivo and in vitro utilities. However, to date there has been no disclosure of an oligonucleotide with the necessary structural features to achieve stable target binding with both Watson-Crick and alternate hydrogen bonds.

Oligonucleotides have been observed to bind by non-Watson-Crick hydrogen bonding in vitro. For example, Cooney et al., 1988, *Science* 241:456 disclose a 27-base single-stranded oligonucleotide which bound to a double-stranded nucleic acid via non-Watson-Crick hydrogen bonds. However, triple-stranded complexes of this type are not very stable, because the oligonucleotide is bound to its target only with less stable alternate hydrogen bonds, i.e., without any Watson-Crick bonds.

Oligonucleotides have been used for a variety of utilities. For example, oligonucleotides can be used as probes for target nucleic acids that are immobilized onto a filter or membrane, or are present in tissues. Sambrook et al. (1989, *Molecular Cloning: A Laboratory Manual*, Vols. 1–3, Cold Spring Harbor Press, NY) provide a detailed review of hybridization techniques.

Furthermore, there has been great interest recently in developing oligonucleotides as regulators of cellular nucleic acid biological function. This interest arises from observations on naturally occurring complementary, or antisense, RNA used by some cells to control protein expression. However, the development of oligonucleotides for in vivo regulation of biological processes has been hampered by several long-standing problems, including the low binding stability and nuclease sensitivity of linear oligonucleotides.

For example, transcription of the human c-myc gene has been inhibited in a cell free, in vitro assay system by a 27-base linear oligonucleotide designed to bind to the c-myc promoter. Inhibition was only observed using a carefully controlled in vitro assay system wherein lower than physiological temperatures were employed, and many cellular enzymes had been removed or inactivated. These conditions were necessary because linear oligonucleotides bind with low affinity and are highly susceptible to enzymes which degrade linear pieces of DNA (Cooney et al.). Splicing of a pre-mRNA transcript essential for Herpes Simplex virus replication has also been inhibited with a linear oligonucleotide which was complementary to an acceptor splice junction. In this instance, a methylphosphonate linkage was employed in the linear oligonucleotide to increase its nuclease resistance. Addition of this chemically-modified oligonucleotide to the growth medium caused reduction in protein synthesis and growth of uninfected cells, most likely because of toxicity problems at high concentrations (Smith et al., 1986, *Proc. Natl. Acad. Sci. USA* 83:2787–2791).

In another example, linear oligonucleotides were used to inhibit human immunodeficiency virus replication in cultured cells. Linear oligonucleotides complementary to sites within or near the terminal repeats of the retrovirus genome and within sites complementary to certain splice junctions were most effective in blocking viral replication. However, these experiments required large amounts of the linear oligonucleotides before an effect was obtained, presumably because of the low binding stability and vulnerability of these linear oligonucleotides to nucleases (Goodchild et al., 1988, *Proc. Natl. Acad. Sci. USA* 85:5507–5511).

Accordingly, oligonucleotides that are useful as regulators of biological processes preferably possess certain properties. The oligonucleotide should bind strongly enough to its complementary target nucleic acid to have the desired regulatory effect. It is generally desirable that the oligonucleotide and its target be sequence specific. Further, the oligonucleotide should have a sufficient half-life under in vivo conditions to accomplish its desired regulatory action in the cell. Hence, the oligonucleotide should be resistant to enzymes that degrade nucleic acids, e.g. nucleases.

While linear oligonucleotides may satisfy the requirement for sequence specificity, linear oligonucleotides are sensitive to nucleases and generally require chemical modification to increase biological half-life. Such modifications increase the cost of making an oligonucleotide and may present toxicity problems. Furthermore, linear oligonucleotides bind to form a two-stranded complex like those present in cellular nucleic acids. Consequently, cellular enzymes can readily manipulate and dissociate a linear oligonucleotide bound in a double-stranded complex with target. The low binding strength and nuclease sensitivity of linear oligonucleotides can thus necessitate administration of high concentrations of oligonucleotide, in turn making such administration toxic or costly.

Furthermore, increased binding strength increases the effectiveness of a regulatory oligonucleotide. Therefore, an oligonucleotide with high binding affinity can be used at lower dosages. Lower dosages decrease costs and reduce the likelihood that a chemically-modified oligonucleotide will be toxic. Therefore, high oligonucleotide binding affinity for target is a highly desirable trait.

The present invention provides single-stranded circular oligonucleotides which, by nature of the circularity of the oligonucleotide and the domains present on the oligonucleotide, are nuclease resistant and bind with strong affinity and high selectivity to their targeted nucleic acids.

Some types of single-stranded circles of DNA or RNA are known. For example, the structures of some naturally occurring viral and bacteriophage genomes are single-stranded circular nucleic acids. Single-stranded circles of DNA have been studied by Erie et al. (1987, *Biochemistry* 26:7150–7159 and 1989, *Biochemistry* 28:268–273). However, none of these circular molecules are designed to bind a target nucleic acid. Hence, the present invention represents an innovation characterized by a substantial improvement relative to the prior art since the subject circular oligonucleotides exhibit high specificity, low or no toxicity and more resistance to nucleases than linear oligonucleotides, and high affinity binding to single- or double-stranded target nucleic acids.

SUMMARY OF THE INVENTION

The present invention provides a single-stranded circular oligonucleotide having at least one parallel binding (P) domain and at least one anti-parallel binding (AP) domain, and having a loop domain between each binding domain to form the circular oligonucleotide. Each P and corresponding AP domain has sufficient complementarity to bind detectably to one strand of a defined nucleic acid target with the P domain binding in a parallel manner to the target, and the AP domain binding in an anti-parallel manner to the target. Sufficient complementarity means that a sufficient number of base pairs exists between the target nucleic acid and the P and/or AP domains of the circular oligonucleotide to achieve stable, i.e. detectable, binding.

In the case where multiple P and AP binding domains are included in the circular oligonucleotides of the present invention, the loop domains separating the P and AP binding domains can constitute, in whole or in part, another P or AP domain which functions as a binding domain in an alternate conformation. In other words, depending upon the particular target, a binding domain (P or AP) can also function as a loop domain for another binding domain and vice versa.

The present invention further provides a single-stranded circular oligonucleotide having at least one of a parallel binding (P) domain, a Hoogsteen anti-parallel domain (HAP), and an anti-parallel binding (AP) domain and having a loop domain between each binding domain, or in the case of circular oligonucleotides having only one binding domain, a loop domain that connects the ends of the binding domain to circularize the oligonucleotide.

Another aspect of the present invention provides the subject single-stranded circular oligonucleotides derivatized with a reporter molecule to provide a probe for a target nucleic acid, or with a drug or other pharmaceutical agent to provide cell specific drug delivery, or with agents that can cleave or otherwise modify the target nucleic acid or, furthermore, with agents that can facilitate cellular uptake or target binding of the oligonucleotide.

An additional aspect of the present invention provides single-stranded circular oligonucleotides linked to a solid support for isolation of a nucleic acid complementary to the oligonucleotide.

Another aspect of the present invention provides a compartmentalized kit for detection or diagnosis of a target nucleic acid including at least one first container providing any one of the present circular oligonucleotides.

A further aspect of the present invention provides a method of detecting a target nucleic acid which involves contacting a single-stranded circular oligonucleotide with a sample containing the target nucleic acid, for a time and under conditions sufficient to form an oligonucleotide-target complex, and detecting the complex. This detection method can be by fluorescent energy transfer.

A still further aspect of the present invention provides a method of regulating biosynthesis of a DNA, an RNA or a protein. This method includes contacting at least one of the subject circular oligonucleotides with a nucleic acid template for the DNA, the RNA or the protein under conditions sufficient to permit binding of the oligonucleotide to a target sequence contained in the template, followed by binding of the oligonucleotide to the target, blocking access to the template and thereby regulating biosynthesis of the DNA, the RNA or the protein.

An additional aspect of the present invention provides pharmaceutical compositions for regulating biosynthesis of a nucleic acid or protein containing a biosynthesis regulating amount of at least one of the subject circular oligonucleotides and a pharmaceutically acceptable carrier.

A further aspect of the present invention provides a method of preparing a single-stranded circular oligonucleotide which includes binding a linear precircle to an end-joining-oligonucleotide, joining the two ends of the precircle and recovering the circular oligonucleotide product.

BRIEF DESCRIPTION OF THE DRAWINGS

FIG. 1 schematically illustrates a circularization reaction for synthesis of single-stranded circular oligonucleotides. A linear precircle oligonucleotide is bound to an oligonucleotide having the same sequence as the target, i.e. an end-joining-oligonucleotide, to form a precircle complex. After ligation, the circularized oligonucleotides are separated from the end-joining-oligonucleotide.

FIG. 2 depicts the sequence of linear precursors to circular oligonucleotides, i.e. precircles (1–3 having SEQ ID NO:5, SEQ ID NO:6 and SEQ ID NO:7), targets (4,5 having SEQ ID NO:8 and SEQ ID NO:9), circular oligonucleotides (6,7,8 and 13 having SEQ ID NO:5–7 and 14), and linear oligonucleotides (9–12 and 14 having SEQ ID NO:10–13 and 15) described in the examples.

(FIG. 14B middle three curves middle three curves, corresponding to molar ratios of SEQ ID NO:18 to SEQ ID NO:21 oligonucleotide of 0.25, 0.5 and 1.0).

DETAILED DESCRIPTION OF THE INVENTION

The present invention relates to single-stranded circular oligonucleotides, i.e. circles, which can bind to nucleic acid targets with high affinity and selectivity.

The strong, selective binding of these circles to either single- or double-stranded targets provides a variety of uses, including methods of regulating such biological processes as DNA replication, RNA transcription, RNA splicing and processing, protein translation and the like. The ability of these circles to selectively and stably bind to targeted nucleic acids makes them ideal as diagnostic probes or as markers to localize, for example, specific sites in a chromosome or other DNA or RNA molecules. Additionally, the present circles are useful for isolation of complementary nucleic acids or for sequence-specific delivery of drugs or other molecules into cells.

In particular, in one embodiment the single-stranded circular oligonucleotides of the present invention have at least one Hoogsteen parallel binding (P) domain and at least one Watson-Crick anti-parallel binding (AP) domain and have a loop domain between each binding domain, so that a circular oligonucleotide is formed. In another embodiment, the single stranded circular oligonucleotides have at least one of a P domain, a Hoogsteen anti-parallel (HAP) domain and an AP domain and a loop domain between each binding domain. In embodiments having one binding domain, the loop domain is between the ends of the binding domain so that a circular oligonucleotide is formed. Moreover, each P, HAP and AP domain exhibits sufficient complementarity to bind to one strand of a defined nucleic acid target with the P domain binding to the target in a parallel manner and the HAP and AP domains binding to the target in an anti-parallel manner.

Figure 21:
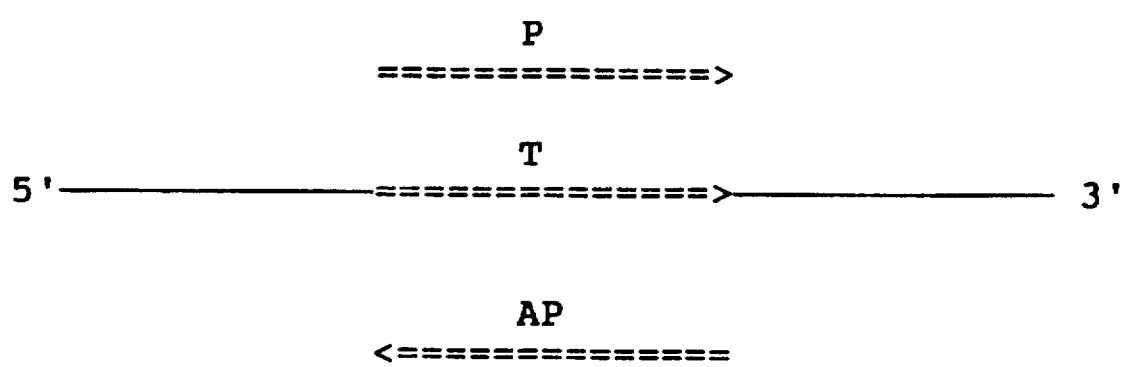
FIG. 21 shows a representative circular arrangement of one set of P and AP oligonucleotide domains relative to each other as well as when bound to a target. The arrows indicate the 5' to 3' orientation of each strand with the 5' end of each domain at the tail and the 3' end at the arrowhead.

The schematic illustration set forth below shows a representative circular arrangement of one set of P and AP oligonucleotide domains relative to each other as well as when bound to a target (T, as indicated in FIG. 21. The arrows indicate the 5' to 3' orientation of each strand with the 5' end of each domain at the tail and the 3' end at the arrowhead. Hence as used herein binding of nucleic acids in a parallel manner means that the 5' to 3' orientation is the same for each strand or nucleotide in the complex. This is the type of binding present between the target and the P domain. As used herein, binding of nucleic acids in an anti-parallel manner means that the 5' to 3' orientations of two strands or nucleotides in a complex lie in opposite directions, i.e. the strands are aligned as found in the typical Watson-Crick base pairing arrangement of double helical DNA.

When more than one P and AP binding domain is present, such binding domains are separated from other P and AP domains by loop domains whose lengths are sufficient to permit binding to multiple targets. Moreover, when a circular oligonucleotide has multiple AP and P domains, a loop domain for one pair of corresponding AP and P binding domains can constitute an AP or P domain for binding to another target. When a circular oligonucleotide has only one P or AP domain, the loop domain is between the ends of the binding domain and serves to circularize the oligonucleotide. When a circular oligonucleotide of the present invention includes, e.g., two pairs of corresponding binding domains, these pairs of corresponding binding domains can also bind separate target sites. Moreover, when a circle has multiple AP and P domains, the corresponding targets need not be linked on one nucleic acid strand. Furthermore, a loop domain of a circular oligonucleotide bound to a given target can be an AP or P domain for binding to a second target when the circular oligonucleotide releases from the first target.

In accordance with this invention, the nucleotide sequences of the P, HAP and AP domains can be determined from the defined sequence of the nucleic acid target by reference to the base pairing rules provided hereinbelow. A target can be either single- or double-stranded and is selected by its known functional and structural characteristics. For example, some preferred targets can be coding regions, origins of replication, reverse transcriptase binding sites, transcription regulatory elements, RNA splicing junctions, or ribosome binding sites, among others. A target can also be selected by its capability for detection or isolation of a DNA or RNA template. Preferred targets are rich in purines, i.e. in adenines and guanines.

The nucleotide sequence of the target DNA or RNA can be known in full or in part. When the target nucleotide sequence is completely known the sequences of the P and AP domains are designed with the necessary degree of complementarity to achieve binding, as detected by known procedures, for example by a change in light absorption or fluorescence. In some instances, the target sequence can be represented by a consensus sequence or be only partially known. For example, circular oligonucleotides (circles) which bind to an entire class of targets represented by a consensus sequence can be provided by designing the P, HAP and AP domains from the target consensus sequence. In this instance some of the targets may match the consensus sequence exactly and others may have a few mismatched bases, but not enough mismatch to prevent binding. Likewise, if a portion of a target sequence is known, one skilled in the art can refer to the base pairing rules provided hereinbelow to design circles which bind to that target with higher affinity than a linear oligonucleotide that has a sequence corresponding to that of the circle.

Thus, the present invention is also directed to circles having P, HAP and AP domains which are sufficiently complementary to bind to a nucleic acid target wherein a sufficient number, but not necessarily all, nucleotide positions in the P, HAP and AP domains are determined from the target sequence in accordance with the base pairing rules of this invention. The number of determined (i.e. known) positions is that number of positions which are necessary to provide sufficient complementarity for binding of the subject oligonucleotides to their targets, as detected by standard procedures including a change in light absorption upon binding or melting.

The base pairing rules of the present invention provide for the P domain to bind to the target by forming base pairs wherein the P domain and target nucleotides have the same 5' to 3' orientation. In particular, these rules are satisfied to the extent needed to achieve binding of a circular oligonucleotide to its nucleic acid target, i.e. the degree of complementarity need not be 100% so long as binding can be detected. Hence, the general rules for determining the sequence of the P domain are thus:

when a base for a position in the target is guanine or a guanine analog, then P has cytosine, or a suitable analog thereof, in a corresponding position;

when a base for a position in the target is adenine or an adenine analog then P has thymine or uracil, or suitable analogs thereof, in a corresponding position;

when a base for a position in the target is thymine or a thymine analog, then P has cytosine or guanine, or suitable analogs thereof, in a corresponding position;

when a base for a position in the target is cytosine or a cytosine analog, then P has cytosine, thymine or uracil, or suitable analogs thereof, in a corresponding position; and when a base for a position in the target is uracil or a uracil analog, then P has cytosine, guanine, thymine, or uracil, or suitable analogs thereof, in a corresponding position.

The base pairing rules of the present invention provide for the AP domain to bind to the target by forming base pairs wherein the AP domain and target nucleotides are oriented in opposite directions. In particular these rules are satisfied to the extent necessary to achieve detectable binding of a circular oligonucleotide to its nucleic acid target, i.e. the degree of complementarity can be less than 100%. Hence, the base pairing rules can be adhered to only insofar as is necessary to achieve sufficient complementarity for binding to be detected between the circular oligonucleotide and its target.

Thus, the general rules for determining the sequence of the AP domain are as follows:

when a base for a position in the target is guanine or a guanine analog, then AP has cytosine or uracil, or suitable analogs thereof, in a corresponding position;

when a base for a position in the target is adenine or an adenine analog, then AP has thymine or uracil, or suitable analogs thereof, in a corresponding position;

when a base for a position in the target is thymine or a thymine analog, then AP has adenine, or a suitable analog thereof, in a corresponding position; and when a base for a position in the target is cytosine or a cytosine analog, then AP has a guanine, or a suitable analog thereof, in corresponding position;

when a base for a position in the target is uracil or a uracil analog, then AP has adenine or guanine, or suitable analogs thereof, in a corresponding position.

In a preferred embodiment, the P, AP and loop domains are not complementary to each other.

The present invention contemplates circular oligonucleotides comprising a binding domain capable of binding to a duplex target whereby the binding domain of the circle binds by Hoogsteen base pairing to a strand of the duplex, thus forming a triple helical complex between one binding domain of the circle and the duplex target. The binding of the binding domain of the circle to the target can be in parallel or antiparallel orientation. When the orientation is parallel, the foregoing base pairing rules for the P domain apply. When the binding is in an antiparallel orientation, the domain is designed Hoogsteen-antiparallel (HAP) and the following rules apply:

when a base for a position in the target is guanine or a guanine analog, then HAP has guanine or a suitable analog thereof in a corresponding position;

when a base for a position in the target is adenine or an adenine analog, then HAP has adenine or thymine or uracil, or suitable analogs thereof, in a corresponding position;

when a base for a position in the target is thymine, cytosine, uracil or analogs thereof then HAP has adenine, cytosine, guanine, thymine, uracil or suitable analogs thereof.

Thus for binding to double-stranded DNA, the present invention provides a circular oligonucleotide comprising a P domain, and further provides a circular oligonucleotide comprising an HAP domain.

Table 1 summarizes the nucleotides that can form anti-parallel base pairs or parallel base pairs with a defined target nucleotide.

TABLE 1

| Target Nucleotide[a] | Anti-Parallel Domain Nucleotide[a] | Parallel Domain Nucleotide[a] | Hoogsteen Anti-Parallel Domain Nucleotide[a] |
|---|---|---|---|
| G | C or U | C | G |
| A | T or U | T or U | A, T or U |
| T | A | C or G | A, C, G, T or U |
| C | G | C, T or U | A, C, G, T or U |
| U | A or G | C, G, T or U | A, C, G, T or U |

[a] Or a suitable analog

Two complementary single-stranded nucleic acids form a stable double helix (duplex) when the strands bind, or hybridize, to each other in the typical Watson-Crick fashion, i.e. via anti-parallel GC and AT base pairs. For the present invention, stable duplex formation and stable triplex formation is achieved when the P and AP domains exhibit sufficient complementarity to the target sequence to achieve stable binding between the circular oligonucleotide and the target molecule. Stable binding occurs when an oligonucleotide remains detectably bound to target under the required conditions.

Complementarity between nucleic acids is the degree to which the bases in one nucleic acid strand can hydrogen bond, or base pair, with the bases in a second nucleic acid strand. Hence, complementarity can sometimes be conveniently described by the percentage, i.e. proportion, of nucleotides which form base pairs between two strands or within a specific region or domain of two strands. For the present invention sufficient complementarity means that a sufficient number of base pairs exist between a target nucleic acid and the HAP or P and/or AP domains of the circular oligonucleotide to achieve detectable binding. Moreover, the degree of complementarity between the P domain and the target and the AP domain and the target need not be the same. When expressed or measured by percentage of base pairs formed, the degree of complementarity can range from as little as about 30–40% complementarity to full, i.e. 100%, complementarity. In general, the overall degree of complementarity between the HAP or P or AP domain and the target is preferably at least about 50%. However, the HAP or P domain can sometimes have less complementarity with the target than the AP domain has with the target, for example the HAP or P domain can have about 30% complementarity with the target while the AP domain can have substantially more complementarity, e.g. 50% to 100% complementarity.

Moreover, the degree of complementarity that provides detectable binding between the subject circular oligonucleotides and their respective targets is dependent upon the conditions under which that binding occurs. It is well known that binding, i.e. hybridization, between nucleic acid strands depends on factors besides the degree of mismatch between two sequences. Such factors include the GC content of the region, temperature, ionic strength, the presence of formamide and types of counter ions present. The effect that these conditions have upon binding is known to one skilled in the art. Furthermore, conditions are frequently determined by the circumstances of use. For example, when a circular oligonucleotide is made for use in vivo, no formamide will be present and the ionic strength, types of counter ions, and temperature correspond to physiological conditions. Binding conditions can be manipulated in vitro to optimize the utility of the present oligonucleotides. A thorough treatment of the qualitative and quantitative considerations involved in establishing binding conditions that allow one skilled in the art to design appropriate oligonucleotides for use under the desired conditions is provided by Beltz et al., 1983, *Methods Enzymol.* 100:266–285 and by Sambrook et al.

Thus for the present invention, one of ordinary skill in the art can readily design a nucleotide sequence for the HAP, P and AP domains of the subject circular oligonucleotides which exhibits sufficient complementarity to detectably bind to its target sequence. As used herein "binding" or "stable binding" means that a sufficient amount of the oligonucleotide is bound or hybridized to its target to permit detection of that binding. Binding can be detected by either physical or functional properties of the target:circular oligonucleotide complex.

Binding between a target and an oligonucleotide can be detected by any procedure known to one skilled in the art, including both functional or physical binding assays. Binding may be detected functionally by determining whether binding has an observable effect upon a biosynthetic process such as DNA replication, RNA transcription, protein translation and the like.

Physical methods of detecting the binding of complementary strands of DNA or RNA are well known in the art, and include such methods as DNase I or chemical footprinting, gel shift and affinity cleavage assays, Northern blotting, dot blotting and light absorption detection procedures. For example, a method which is widely used, because it is so simple and reliable, involves observing a change in light absorption of a solution containing an oligonucleotide and a target nucleic acid at 220 to 300 nm as the temperature is slowly increased. If the oligonucleotide has bound to its target, there is a sudden increase in absorption at a characteristic temperature as the oligonucleotide and target dissociate or melt.

The binding between an oligonucleotide and its target nucleic acid is frequently characterized by the temperature at which 50% of the oligonucleotide is melted from its target. This temperature is the melting temperature ($T_m$). A higher $T_m$ means a stronger or more stable complex relative to a complex with a lower $T_m$. The stability of a duplex increases with increasing G:C content since G:C base pairs have three hydrogen bonds whereas A:T base pairs have two. The circular oligonucleotides of the present invention that contain a P and AP domain provide additional hydrogen bonds and hence more stability since two binding domains are available for bonding to a single target nucleic acid. Hence, the triplex formed by such a circular oligonucleotide bound to a single stranded target nucleic acid should melt at a higher $T_m$ than the duplex formed by a linear oligonucleotide and a target.

Circular oligonucleotides bind to a nucleic acid target through hydrogen bonds formed between the nucleotides of the binding domains and the target. The AP domain can bind by forming Watson-Crick hydrogen bonds. The P or HAP domain can bind to the target nucleotides by forming non-Watson-Crick hydrogen bonds (Table 1). When two nucleotides from different strands of DNA or RNA hydrogen bond by the base pairing rules defined herein, a base pair or duplex is formed. When a nucleotide from AP and a nucleotide from P both bind to the same target nucleotide, a base triad is formed.

Parallel domain base pairing with a complementary target strand of nucleic acid is thermodynamically less favorable than Watson-Crick base pairing; however, when both parallel and antiparallel pairing modes are present in a single molecule, highly stable complexes can form. Thus, two opposing domains of a circular oligomer form a complex with a central target, giving a triplex structure, or a triple helical complex, bounded by the two looped ends of the circle. For example, this arrangement can allow formation of up to four hydrogen bonds when two thymines bind to a target adenine and up to five hydrogen bonds when two cytosines bind to a target guanine.

Furthermore, because of the binding characteristics of the P and AP domains, the present circular oligonucleotides have a higher selectivity for a single stranded target than do corresponding linear oligonucleotides. At least two factors can contribute to this high selectivity. First, circular oligonucleotides of this invention bind twice to the same central target strand. Hence two domains are involved in selecting a target. Second, protonation of cytosine in a C+G–C triad is favored only when this triad forms and the additional proton gives the triad a positive charge. This positive charge can lessen the negative charge repulsions arising from the juxtapositioning of three phosphodiester backbones.

Protonation of C+G–C triads occurs most readily at low pH and formation of C+G–C triads is favored over formation of many other triads at low pH. Therefore, P and AP domains which are cytosine-rich more stably bind a complementary guanine-rich target at low pH than cytosine-poor P and AP domains bind a guanine-poor target. The skilled artisan can take advantage of the effect of protonation upon C+G–C triad formation to design circular oligonucleotides in accordance with the present invention whose selectivity for a target is enhanced if the pH of the hybridization reaction is known or can be adjusted. This is done simply by selecting a guanine-rich target and constructing cytosine-rich P and AP binding domains if the hybridization pH is low, or by selecting a guanine-poor target and constructing cytosine-poor P and AP binding domains if the hybridization pH is high. For these purposes a low pH is about 5.0 to about 6.8, and preferably about 5.5, whereas a high pH is about 7.0 to about 9.0, and for use in vivo preferably about 7.4. As used herein a cytosine-rich P or AP binding domain has about 2 to about 20 cytosines, and a guanine-rich target has about 2 to about 20 guanines. Conversely, a cytosine-poor P or AP binding domain has no more than one cytosine, while a guanine-poor target has no more than one guanine.

The circular oligonucleotides of the present invention can be constructed to include more than one HAP or P or AP binding domain to permit binding of the oligonucleotide to more than one target. The skilled artisan can also select target sites for such multiple-binding domain oligonucleotides which permit construction of cytosine-rich and cytosine-poor pairs of P and AP binding domains. By including a cytosine-rich pair of binding domains with a cytosine-poor pair of binding domains, the skilled artisan can direct the circle to a particular target either by adjusting the pH or by taking advantage of natural variations in pH.

For example, two targets can be selected, a first target having many guanines and a second target with few guanines. A circular oligonucleotide can be prepared to include a first pair of cytosine-rich AP and P binding domains complementary to the first target and a second pair of cytosine-poor AP and P binding domains complementary to the second target in accordance with the procedures provided by the present invention. At low pH values, e.g. about pH 5.0 to 6.5, binding to the guanine-rich target is very highly favored whereas at high pH values, e.g. about pH 7.2 to 9.0, binding to the guanine-poor target is highly favored.

Such oligonucleotides are therefore multifunctional, conformationally mobile ligands capable of controlled, selective binding to more than a single target site.

Moreover the selectivity of circular oligonucleotides can be controlled by taking advantage of pH variations in vivo as well as in vitro, since variations in pH occur naturally in vivo as well as being experimentally generated in vitro. For example, solid tumors can have a pH of 5.5 to 6.8 which is considerably lower than the average intracellular pH of 7.4 (Meyer et al. 1948 *Cancer Res.* 8:513).

Therefore, according to the present invention, the biosynthesis of a DNA, an RNA or a protein within a targeted mammalian tumor can be selectively regulated, without substantially affecting the biosynthesis of DNA, RNA or proteins in non-targeted cells, e.g., that DNA, RNA or protein in a neighboring normal cell. This can be accomplished in accordance with the present invention by administering a circular oligonucleotide having a cytosine-rich pair of P and AP binding domains as well as a cytosine-poor pair of P and AP binding domains, wherein the cytosine-rich P and AP domains bind to the target within a nucleic acid template for the DNA, RNA or protein. Since the pH in such a solid tumor is lower than the pH of surrounding normal tissues, the circular oligonucleotide preferentially binds to the guanine-rich target within the tumor. However, in normal tissues where the pH is higher, the circular oligonucleotide has less preference for the guanine-rich target and binds to the guanine-poor target. By selecting a guanine-rich target whose function is essential for cell growth or survival, and a guanine-poor target with a non-essential function, the growth of the tumor can thereby be inhibited or arrested.

Unlike linear oligonucleotides, the present circular oligonucleotides can displace one strand of a double-stranded target under conditions where denaturation of the double-stranded target is thermodynamically unfavorable. Linear oligonucleotides do not have this capacity to displace a strand of a duplex. For example, the half-life of a double-stranded target in the presence of a complementary linear oligonucleotide is about 58 min, and therefore the linear oligonucleotide has little utility for displacing one strand of the duplex target. However, a double-stranded target has a half-life of only 30 sec in the presence of the present circular oligonucleotides. Therefore, the circular oligonucleotides of the present invention have utility not only for binding single-stranded targets, but also for binding to double-stranded targets.

Further, the circular oligonucleotides of the present invention may bind to a double stranded target through the binding of only one binding domain, such that a triplex is formed, or to a single-stranded target through the binding of only one binding domain such that a duplex is formed. For example, a circular oligonucleotide comprising one AP domain is useful for binding to a single-stranded target. A circular oligonucleotide comprising one P or one HAP domain is useful for binding to a double-stranded target. The in vitro binding affinity of circles utilizing one binding domain to form a duplex with a single stranded target is comparable to the binding affinity of the analogous linear oligonucleotide. However, the circles that utilize one binding domain are far superior for both in vitro and in vivo applications due to their greater stability, and particularly nuclease resistance, relative to linear oligonucleotides.

Accordingly, since both single- and double-stranded nucleic acids are available as targets for the present circular oligonucleotides, these circular oligonucleotides can have greater utility than linear oligonucleotides. For example, the present circular oligonucleotides are better regulators of biological processes in vivo and better in vitro diagnostic probes than corresponding linear oligonucleotides.

When the nucleic acid template extends beyond the central triple-stranded target:circle complex, a P or an AP domain may bind as duplex on either side of the triple standard complex. Hence a target:circular oligonucleotide complex can be partially two stranded and partially three-stranded, wherein two-stranded portions can be P:target duplexes, without bound AP nucleotides, or AP:target duplexes, without bound P nucleotides. This binding arrangement is a staggered binding arrangement.

Each P domain, HAP domain, AP domain and target can independently have about 2 to about 200 nucleotides with preferred lengths being about 4 to about 100 nucleotides. The most preferred lengths are 6 to 36 nucleotides.

The binding domains are separated by loop domains which can independently have from about 2 to about 2000 nucleotides. A preferred loop length is from about 3 to about 8 nucleotides with an especially preferred length being about 5 nucleotides.

According to the present invention, the loop domains do not have to be composed of nucleotide bases. Non-nucleotide loops can make the present circular oligonucleotides less expensive to produce. More significantly, circular oligonucleotides with non-nucleotide loops are more resistent to nucleases and therefore have a longer biological half-life than linear oligonucleotides. Furthermore, loops having no charge, or a positive charge, can be used to promote binding by eliminating negative charge repulsions between the loop and target. In addition, circular oligonucleotides having uncharged or hydrophobic non-nucleotide loops can penetrate cellular membranes better than circular oligonucleotides with nucleotide loops.

As contemplated herein, non-nucleotide loop domains can be composed of alkyl chains, polyethylene glycol or oligoethylene glycol chains or other chains providing the necessary steric or flexibility properties which are compatible with oligonucleotide synthesis. The length of these chains is equivalent to about 2 to about 2000 nucleotides, with preferred lengths equivalent to about 3 to about 8 nucleotides. The most preferred length for these chains is equivalent to about 5 nucleotides.

Preferred chains for non-nucleotide loop domains are polyethylene glycol or oligoethylene glycol chains. In particular, oligoethylene glycol chains having a length similar to a 5 nucleotide chain, e.g. a pentaethylene glycol, a hexaethylene glycol or a heptaethylene glycol chain, are preferred. Covalent bonds, for example disulfide bonds, may comprise the loop domain.

The circular oligonucleotides of the present invention are composed of single stranded DNA, RNA or a mixture thereof. Circular oligonucleotides comprising DNA and RNA are referred to herein as chimeric oligonucleotides. All possible chimeric oligonucleotides, for example, chimeric oligonucleotide circles containing a DNA binding domain and an RNA binding domain, or RNA binding domains and DNA loops, are contemplated by the present invention. The base composition of the nucleotides can vary and may include guanine (G), adenine (A), thymine (T), cytosine (C), or uracil (U) or any nucleotide analog that is capable of hydrogen bonding in a parallel or anti-parallel manner to a target nucleotide.

Nucleotide analogs include pseudocytidine, isopseudocytidine, imidazole, 3-aminophenyl-imidazole, 2'-O-methyl-adenosine, 7-deazadenosine, 7-deazaguanosine, 7-deazaxanthosine, 4-acetylcytidine, 5-(carboxy-hydroxylmethyl)-uridine, 2'-O-methylcytidine, 5-carboxymethylaminomethyl-2-thioridine, 5-carboxymethylamino-methyluridine, dihydrouridine, 2'-O-methyluridine, pseudouridine, 2'-O-methyl-pseudouridine, beta, D-galactosylqueosine, 2'-O-methylguanosine, inosine, N6-isopentenyladenosine, 1-methyladenosine, 1-methyl-pseudouridine, 1-methylguanosine, 1-methylinosine, 2,2-dimethylguanosine, 2-methyladenosine, 2-methylguanosine, 3-methylcytidine, 5-methylcytidine, 5-methyluridine, N6-methyl-adenosine, 7-methylguanosine, 5-methylamino-methyluridine, 5-methoxyaminomethyl-2-thiouridine, β-D-mannosylqueosine, 5-methoxycarbonylmethyluridine, 5-methoxyuridine, 2-methyl-thio-N6-isopentenyladenosine, N-(9-beta-D-ribofuranosyl-2-methylthiopurine-6-yl)-carbamoyl) threonine, N-(9-beta-D-ribofuranosylpurine-6-yl)-N-methylcarbamoyl)threonine, and thioguanosine.

When possible, either ribose or deoxyribose or 2'-O-methylribose sugars can be used with these analogs. Nucleotides bases in an α-anomeric conformation can also be used in the circular oligonucleotides of the present invention.

Preferred nucleotide analogs are unmodified G, A, T, C and U nucleotides; pyrimidine analogs with lower alkyl, lower alkoxy, lower alkynyl, lower alkenyl, lower alkylamine, phenyl or lower alkyl substituted phenyl groups in the 5 position of the base and purine analogs with similar groups in the 7 or 8 position of the base. Especially preferred nucleotide analogs are 5-methylcytosine, 5-methyluracil, diaminopurine, and nucleotides with a 2'-O-methylribose, 2'-fluorodeoxyribose or 2'-aminodeoxyribose moiety in place of ribose or deoxyribose. In a particularly preferred embodiment, the oligonucleotide circle comprises RNA in which some of the pyrimidines are C-5 methylated and some of the ribose moieties are 2'-O-methylribose (other sugar modifications?).

As used herein lower alkyl, lower alkoxy and lower alkylamine contain from 1 to 6 carbon atoms and can be straight chain or branched. These groups include methyl, ethyl, propyl, isopropyl, butyl, isobutyl, tertiary butyl, amyl, hexyl and the like. A preferred alkyl group is methyl.

It has been discovered in accordance with the present invention that the composition of the binding domains may be designed to optimize binding to a particular target species. Optimization is contingent upon the intended use of the oligonucleotides. For example, for in vivo use or diagnostic applications involving biological fluids, resistance to nucleases is a critical consideration. In other diagnostic applications, binding affinity can be optimized with less consideration of nuclease resistance. For example, for binding to a single-stranded DNA target in applications involving biological fluids, a preferred circle contains an DNA P domain and a DNA AP domain. For binding to a single-stranded RNA target, the preferred circle contains RNA in both P and AP binding domains. In both cases, affinity can be increased by incorporating methylated pyrimidine bases into the binding domains.

For binding to duplex DNA at neutral pH, pyrimidine rich binding domains composed of RNA or 2'-O-methyl RNA are preferred. Affinity can be increased by incorporating methylated pyrimidine bases into the binding domains.

For binding to duplex RNA, or RNA-DNA hybrids, binding domains composed of RNA are preferred in embodiments in which susceptibility to nucleases is minimal. Again C-5 methylation of pyrimidine bases is preferred.

The skilled artisan can modify the composition of the circles in accordance with the foregoing guidelines to determine the preferred circle for binding under specific conditions.

It has been further discovered in accordance with the present invention that circles can be designed to selectively bind DNA versus RNA targets. For example, at both neutral and acidic pH, a circle with DNA P and AP domains hybridizes to a complementary single-stranded DNA target with significantly higher affinity than to an RNA target having the same affinity. In contrast, circles composed of RNA P and AP domains generally exhibit a small preference for binding RNA targets.

In view of the discovery of the selectivity properties of DNA and RNA circles in accordance with the present invention, one of ordinary skill in the art is able to choose circular oligonucleotides that select RNA or DNA strands from a mixture thereof. The ability to bind RNA or DNA strands with high selectivity under physiological conditions is useful in diagnostic and therapeutic applications where both RNA and DNA strands are present.

Circular oligonucleotides can be made first as linear oligonucleotides and then circularized. Linear oligonucleotides can be made by any of a myriad of procedures known for making DNA or RNA oligonucleotides. For example, such procedures include enzymatic synthesis and chemical synthesis.

Enzymatic methods of DNA oligonucleotide synthesis frequently employ Klenow, T7, T4, Taq or *E. coli* DNA polymerases as described in Sambrook et al. Enzymatic methods of RNA oligonucleotide synthesis frequently employ SP6, T3 or T7 RNA polymerase as described in Sambrook et al. Reverse transcriptase can also be used to synthesize DNA from RNA (Sambrook et al.). To prepare oligonucleotides enzymatically requires a template nucleic acid which can either be synthesized chemically, or be obtained as mRNA, genomic DNA, cloned genomic DNA, cloned cDNA or other recombinant DNA. Some enzymatic methods of DNA oligonucleotide synthesis can require an additional primer oligonucleotide which can be synthesized chemically. Finally, linear oligonucleotides can be prepared by PCR techniques as described, for example, by Saiki et al., 1988, *Science* 239:487.

Chemical synthesis of linear oligonucleotides is well known in the art and can be achieved by solution or solid phase techniques. Moreover, linear oligonucleotides of defined sequence can be purchased commercially or can be made by any of several different synthetic procedures including the phosphoramidite, phosphite triester, H-phosphonate and phosphotriester methods, typically by automated synthesis methods. The synthesis method selected can depend on the length of the desired oligonucleotide and such choice is within the skill of the ordinary artisan. For example, the phosphoramidite and phosphite triester method produce oligonucleotides having 175 or more nucleotides while the H-phosphonate method works well for oligonucleotides of less than 100 nucleotides. If modified bases are incorporated into the oligonucleotide, and particularly if modified phosphodiester linkages are used, then the synthetic procedures are altered as needed according to known procedures. In this regard, Uhlmann et al. (1990, Chemical Reviews 90:543–584) provide references and outline procedures for making oligonucleotides with modified bases and modified phosphodiester linkages.

Synthetic, linear oligonucleotides may be purified by polyacrylamide gel electrophoresis, or by any of a number of chromatographic methods, including gel chromatography and high pressure liquid chromatography. To confirm a nucleotide sequence, oligonucleotides may be subjected to DNA sequencing by any of the known procedures, including Maxam and Gilbert sequencing, Sanger sequencing, capillary electrophoresis sequencing the wandering spot sequencing procedure or by using selective chemical degradation of oligonucleotides bound to Hybond paper. Sequences of short oligonucleotides can also be analyzed by laser desorption mass spectroscopy or by fast atom bombardment (McNeal, et al., 1982, *J. Am. Chem. Soc.* 104:976; Viari, et al., 1987, *Biomed. Environ. Mass Spectrom.* 14:83; Grotjahn et al., 1982, *Nuc. Acid Res.* 10:4671). Sequencing methods are also available for RNA oligonucleotides.

The present invention provides several methods of preparing circular oligonucleotides from linear precursors (i.e. precircles), including a method wherein a precircle is synthesized and bound to an end-joining-oligonucleotide and the two ends of the precircle are joined. Any method of joining two ends of an oligonucleotide is contemplated by the present invention, including chemical methods employing, for example, known coupling agents like BrCN, N-cyanoimidazole $ZnCl_2$, 1-ethyl-3-(3-dimethylaminopropyl)-carbodiimide and other carbodiimides and carbonyl diimidazoles. Furthermore, the ends of a precircle can be joined by condensing a 5' phosphate and a 3' hydroxy, or a 5' hydroxy and a 3' phosphate.

In accordance with the present invention, a simple one-step chemical method is provided to construct the subject circular oligonucleotides, or circles, from precircles. An oligonucleotide is constructed which has the same sequence as the target nucleic acid; this is the end-joining oligonucleotide, or adaptor. A DNA or RNA linear precircle is chemically or enzymatically synthesized and phosphorylated on its 5' or 3' end, again by either chemical or enzymatic means. The precircle and the end-joining oligonucleotide are mixed and annealed, thereby forming a complex in which the 5' and 3' ends of the precircle are adjacent, as depicted in FIG. 1. It is preferred that the ends of the precircle fall within a binding domain, not within a loop, and preferably within the anti-parallel binding domain rather than the parallel domain. Moreover, it is preferred that a precircle have a 3'-phosphate rather than a 5'-phosphate. After complex formation, the ends undergo a condensation reaction in a buffered aqueous solution containing divalent metal ions and BrCN at about pH 7.0. In a preferred embodiment the buffer is imidazole-Cl at pH 7.0 with a divalent metal such as Ni, Zn, Mn, or Co. Ni is the most preferred divalent metal. Condensation occurs after about 6–48 hr. of incubation at 4°–37° C. Other divalent metals, such as Cu, Pb, Ca and Mg, can also be used.

One method for RNA circularization incorporates the appropriate nucleotide sequences, preferably in a loop domain, into an RNA oligonucleotide to promote self splicing, since a circular product is formed under the appropriate conditions (Sugimoto et al., 1988, *Biochemistry* 27:6384–6392).

Enzymatic circle closure is also possible using DNA ligase or RNA ligase under conditions appropriate for these enzymes.

Circular oligonucleotides can be separated from the end-joining oligonucleotide by denaturing gel electrophoresis or melting followed by gel electrophoresis, size selective chromatography, or other appropriate chromatographic or electrophoretic methods. The recovered circular oligonucleotide can be further purified by standard techniques as needed for its use in the methods of the present invention. Alternatively, the end-joining oligonucleotide may be attached to a solid support and recovered by filtration.

The present invention also contemplates derivatization or chemical modification of the subject oligonucleotides with chemical groups to facilitate cellular uptake. For example, covalent linkage of a cholesterol moiety to an oligonucleotide can improve cellular uptake by 5- to 10- fold which in turn improves DNA binding by about 10- fold (Boutorin et al., 1989, *FEBS Letters* 254:129–132). Other ligands for cellular receptors may also have utility for improving cellular uptake, including, e.g. insulin, transferrin and others. Similarly, derivatization of oligonucleotides with poly-L-lysine can aid oligonucleotide uptake by cells (Schell, 1974, *Biochem. Biophys. Acta* 340:323, and Lemaitre et al., 1987, *Proc. Natl. Acad. Sci. USA* 84:648). Certain protein carriers can also facilitate cellular uptake of oligonucleotides, including, for example, serum albumin, nuclear proteins possessing signals for transport to the nucleus, and viral or bacterial proteins capable of cell membrane penetration. Therefore, protein carriers are useful when associated with or linked to the circular oligonucleotides of this invention. Accordingly, the present invention contemplates derivatization of the subject circular oligonucleotides with groups capable of facilitating cellular uptake, including hydrocarbons and non-polar groups, cholesterol, poly-L-lysine and proteins, as well as other aryl or steroid groups and polycations having analogous beneficial effects, such as phenyl or naphthyl groups, quinoline, anthracene or phenanthracene groups, fatty acids, fatty alcohols and sesquiterpenes, diterpenes and steroids.

The present invention further contemplates derivatization of the subject oligonucleotides with agents that can cleave or modify the target nucleic acid or other nucleic acid strands associated with or in the vicinity of the target. For example, viral DNA or RNA can be targeted for destruction without harming cellular nucleic acids by administering a circular oligonucleotide complementary to the targeted nucleic acid which is linked to an agent that, upon binding, can cut or render the viral DNA or RNA inactive. Nucleic acid destroying agents that are contemplated by the present invention as having cleavage or modifying activities include, for example, RNA and DNA nucleases, ribozymes that can cleave RNA, azidoproflavine, acridine, EDTA/Fe, chloroethylamine, azidophenacyl and phenanthroline/Cu. Uhlmann et al. (1990, *Chemical Reviews* 90:543–584) provide further information on the use of such agents and methods of derivatizing oligonucleotides that can be adapted for use with the subject circular oligonucleotides.

Derivatization of the subject circular oligonucleotides with groups that facilitate cellular uptake or target binding, as well as derivatization with nucleic acid destroying agents or drugs, can be done by any of the procedures known to one skilled in the art. Moreover, the desired groups can be added to nucleotides before synthesis of the oligonucleotide. For example, these groups can be linked to the 5-position of T or C and these modified T and C nucleotides can be used for synthesis of the present circular oligonucleotides. In addition, derivatization of selected nucleotides permits incorporation of the group into selected domains of the circular oligonucleotide. For example, in some instances it is preferable to incorporate certain groups into a loop where that group will not interfere with binding, or into an AP, HAP or P domain to facilitate cleavage or modification of the target nucleic acid.

In accordance with the present invention, modification in the phosphodiester backbone of circular oligonucleotides is also contemplated. Such modifications can aid uptake of the oligonucleotide by cells or can extend the biological half-life of such nucleotides. For example, circular oligonucleotides may penetrate the cell membrane more readily if the negative charge on the internucleotide phosphate is eliminated. This can be done by replacing the negatively charged phosphate oxygen with a methyl group, an amine or by changing the phosphodiester linkage into a phosphotriester linkage by addition of an alkyl group to the negatively charged phosphate oxygen. Alternatively, one or more of the phosphate atoms which is part of the normal phosphodiester linkage can be replaced. For example, NH-P, $CH_2$-P or S-P linkages can be formed. Accordingly, the present invention contemplates using methylphosphonates, phosphorothioates, phosphorodithioates, phosphotriesters and phosphorus-boron (Sood et al., 1990, *J. Am. Chem. Soc.* 112:9000) linkages. The phosphodiester group can be replaced with siloxane, carbonate, acetamidate or thioether groups. These modifications can also increase the resistance of the subject oligonucleotides to nucleases. Methods for synthesis of oligonucleotides with modified phosphodiester linkages are reviewed by Uhlmann et al.

Circular oligonucleotides with non-nucleotide loops can be prepared by any known procedure. For example, Durand et al. (1990, *Nucleic Acids Res.* 18:6353–6359) provides synthetic procedures for linking non-nucleotide chains to DNA. Such procedures can generally be adapted to permit an automated synthesis of a linear oligonucleotide precursor which is then used to make a circular oligonucleotide of the present invention. In general, groups reactive with nucleotides in standard DNA synthesis, e.g. phosphoramidite, H-phosphonate, dimethoxytrityl, monomethoxytrityl and the like, can be placed at the ends of non-nucleotide chains and nucleotides corresponding to the ends of P and AP domains can be linked thereto.

Phosphoramidite chemistry can be used to synthesize RNA oligonucleotides as described (Reese, C. B. In *Nucleic Acids & Molecular Biology;* Springer-Verlag: Berlin, 1989; Vol. 3, p. 164; and Rao, et al., 1987, *Tetrahedron Lett.* 28:4897). Also, different nucleotide sugars, for example 2'-O-methylribose can be incorporated into the oligonucleotides of this invention.

The synthesis of RNA 2'-O-methyl-oligoribonucleotides and DNA oligonucleotides differ only slightly. RNA 2'-O-methyloligonucleotides can be prepared with minor modifications of the amidite, H-phosphonate or phosphotriester methods (Shibahara et al, 1987, *Nucleic Acids Res.* 15:4403; Shibahara et al., 1989, *Nucleic Acids Res.* 17:239; Anoue et al., 1987, *Nucleic Acids Res.* 15:6131).

The present invention contemplates a variety of utilities for the subject circular oligonucleotides which are made possible by their selective and stable binding properties with both single- and double-stranded targets. Some utilities include, but are not limited to: use of circular oligonucleotides of defined sequence, bound to a solid support, for affinity isolation of complementary nucleic acids; use of the subject oligonucleotides to provide sequence specific stop signals during polymerase chain reaction (PCR); covalent attachment of a drug, drug analog or other therapeutic agent to circular oligonucleotides to allow cell type specific drug delivery; labeling circular oligonucleotides with a detectable reporter group for localizing, quantitating or identifying complementary target nucleic acids; and binding circular oligonucleotides to a cellular or viral nucleic acid template and regulating biosynthesis directed by that template.

The subject circular oligonucleotides can be attached to a solid support such as silica, cellulose, nylon, polystyrene, polyacrylamide, agarose and other natural or synthetic materials that are used to make beads, filters, and column chromatography resins. Attachment procedures for nucleic acids to solid supports of these types are well known; any known attachment procedure is contemplated by the present invention. A circular oligonucleotide attached to a solid support can then be used to isolate a complementary nucleic acid. Isolation of the complementary nucleic acid can be effected by incorporating the oligonucleotide:solid support into a column for chromatographic procedures. Other isolation methods can be accomplished without incorporation of the oligonucleotide:solid support into a column, e.g. by utilization of filtration procedures. Circular oligonucleotide-:solid supports can be used, for example, to isolate poly(A)$^+$ mRNA from total cellular or viral RNA by making a circular oligonucleotide with P and AP domain poly(dT) or poly(U) sequences. Circular oligonucleotides are ideally suited to applications of this type because they are nuclease resistant and bind target nucleic acids so strongly.

Further utilities are available for the subject oligonucleotides in the field of polymerase chain reaction (PCR) technology. PCR technology provides methods of synthesizing a double-standard DNA fragment encoded in a nucleic acid template between two known nucleic acid sequences which are employed as primer binding sites. In some instances it is desirable to produce a single-stranded DNA fragment before or after having made some of the double stranded fragment, or to selectively prevent amplification of a particular species. This can be done by, for example, binding a circular oligonucleotide of the present invention to one of the primer binding sites or to a site lying between the primer binding sites.

The present invention also contemplates use of the subject circular oligonucleotides for targeting drugs to specific cell types. Such targeting can allow selective destruction or enhancement of particular cell types, e.g. inhibition of tumor cell growth can be attained. Different cell types express different genes, so that the concentration of a particular mRNA can be greater in one cell type relative to another cell type. Such an mRNA is a target mRNA for cell type specific drug delivery by circular oligonucleotides linked to drugs or drug analogs. Cells with high concentrations of target mRNA are targeted for drug delivery by administering to the cell a circular oligonucleotide with a covalently linked drug that is complementary to the target mRNA.

The present invention also contemplates labeling the subject circular oligonucleotides for use as probes to detect a target nucleic acid. Labelled circular oligonucleotide probes have utility in diagnostic and analytical hybridization procedures for localizing, quantitating or detecting a target nucleic acid in tissues, chromosomes or in mixtures of nucleic acids.

Labeling of a circular oligonucleotide can be accomplished by incorporating nucleotides linked to a reporter group into the subject circular oligonucleotides. A reporter group, as defined herein, is a molecule or group which, by its chemical nature, provides an identifiable signal allowing detection of the circular oligonucleotide. Detection can be either qualitative or quantitative. The present invention contemplates using any commonly used reporter molecule including radionuclides, enzymes, biotins, psoralens, fluorophores, chelated heavy metals, and luciferin. The most commonly used reporter groups are either enzymes, fluorophores or radionuclides linked to the nucleotides which are used in circular oligonucleotide synthesis. Commonly used enzymes include horseradish peroxidase, alkaline phosphatase, glucose oxidase and β-galactosidase, among others. The substrates to be used with the specific enzymes are generally chosen because a detectably colored product is formed by the enzyme acting upon the substrate. For example, p-nitrophenyl phosphate is suitable for use with alkaline phosphatase conjugates; for horseradish peroxidase, 1,2-phenylenediamine, 5-aminosalicyclic acid or toluidine are commonly used. Fluorophores may be detected, for example by microscopy or digital imaging. Similarly, methods for detecting radionuclides are well-known in the art. The probes so generated have utility in the detection of a specific DNA or RNA target in, for example, Southern analysis, Northern analysis, in situ hybridization to tissue sections or chromosomal squashes and other analytical and diagnostic procedures. The methods of using such hybridization probes are well known and some examples of such methodology are provided by Sambrook et al.

The present circular oligonucleotides can be used in conjunction with any known detection or diagnostic procedure which is based upon hybridization of a probe to a target nucleic acid. Moreover, the present circular oligonucleotides can be used in any hybridization procedure which quantitates a target nucleic acid, e.g., by competitive hybridization between a target nucleic acid present in a sample and a labeled tracer target for one of the present oligonucleotides. Furthermore, the reagents needed for making a circular oligonucleotide probe and for utilizing such a probe in a hybridization procedure can be marketed in a kit.

The kit can be compartmentalized for ease of utility and can contain at least one first container providing reagents for making a precircle precursor for a circular oligonucleotide, at least one second container providing reagents for labeling the precircle with a reporter molecule, at least one third container providing reagents for circularizing the precircle, and at least one fourth container providing reagents for isolating the labeled circular oligonucleotide.

Moreover the present invention provides a kit for isolation of a template nucleic acid. Such a kit has at least one first container providing a circular oligonucleotide which is complementary to a target contained within the template. For example, the template nucleic acid can be cellular and/or viral poly(A) $^+$ mRNA and the target can be the poly(A) $^+$ tail. Hence circular oligonucleotides of the present invention which have utility for isolation of poly(A) $^+$ mRNA have P and AP domain sequences of poly(dT) or poly(U).

Further, a kit for the detection of any target nucleic acid is provided which contains a circular oligonucleotide of the present invention linked to a reporter group. Additional containers providing reagents for detecting a linked reporter group can also be provided in the kit.

Furthermore, the present invention provides kits useful when diagnosis of a disease depends upon detection of a specific, known target nucleic acid. Such nucleic acid targets can be, for example, a viral nucleic acid, an extra or missing chromosome or gene, a mutant cellular gene or chromosome, an aberrantly expressed RNA and others. The kits can be compartmentalized to contain at least one first container providing a circular oligonucleotide linked to a reporter molecule and at least one second container providing reagents for detection of the reporter molecule.

Therefore, as contemplated by the present invention, the kits disclosed herein can include any elements recognized or conventionally used by the skilled artisan for constructing, purifying and using oligonucleotides. Moreover, the present kits can include specific chemical reagents or end-joining oligonucleotides for making the present circular oligonucleotide.

One aspect of the present invention provides a method of regulating biosynthesis of a DNA, an RNA or a protein by contacting at least one of the subject circular oligonucleotides with a nucleic acid template for that DNA, that RNA or that protein in an amount and under conditions sufficient to permit the binding of the oligonucleotide(s) to a target sequence contained in the template. The binding between the oligonucleotide(s) and the target blocks access to the template, and thereby regulates biosynthesis of the nucleic acid or the protein. Blocking access to the template prevents proteins and nucleic acids involved in the biosynthetic process from binding to the template, from moving along the template, or from recognizing signals encoded within the template. Alternatively, when the template is RNA, regulation can be accomplished by allowing selective degradation of the template. For example, RNA templates bound by the subject circular oligonucleotides are susceptible to degradation by RNase H and RNase H degradation of a selected RNA template can thereby regulate use of the template in biosynthetic processes.

As used herein, biosynthesis of a nucleic acid or a protein includes cellular and viral processes such as DNA replication, DNA reverse transcription, RNA transcription, RNA splicing, RNA polyadenylation, RNA translocation and protein translation, and of which can lead to production of DNA, RNA or protein, and involve a nucleic acid template at some stage of the biosynthetic process.

As used herein, regulating biosynthesis includes inhibiting, stopping, increasing, accelerating or delaying biosynthesis. Regulation may be direct or indirect, i.e. biosynthesis of a DNA, RNA or protein may be regulated directly by binding a circular oligonucleotide to the template for that DNA, RNA or protein; alternatively, biosynthesis may be regulated indirectly by oligonucleotide binding to a second template encoding a protein that plays a role in regulating the biosynthesis of the first DNA, RNA or protein.

The nucleic acid templates can be RNA or DNA and can be single-stranded or double-stranded. While the present circular oligonucleotides bind to only one strand of a target present in a duplex, such duplexes may be opened during biological processes and thereby a single strand becomes available for binding. Alternately, the HAP or P domain of the present circular oligonucleotides can bind to a double-stranded target without strand opening to form a stable triplex.

DNA replication from a DNA template is mediated by proteins which bind to an origin of replication where they open the DNA and initiate DNA synthesis along the DNA template. To inhibit DNA replication in accordance with the present invention, circular oligonucleotides are selected which bind to one or more targets in an origin of replication. Such binding blocks template access to proteins involved in DNA replication. Therefore initiation and procession of DNA replication is inhibited. As an alternative method of inhibiting DNA replication, expression of the proteins which mediate DNA replication can be inhibited at, for example, the transcriptional or translational level. As one skilled in the art recognizes, DNA replication can also be increased, e.g. by inhibiting expression of a protein repressor of DNA replication.

DNA replication from an RNA template is mediated by reverse transcriptase binding to a region of RNA also bound by a nucleic acid primer. To inhibit DNA replication from an RNA template, reverse transcriptase or primer binding can be blocked by binding a circular oligonucleotide to the primer binding site, and thereby blocking access to that site. Moreover, inhibition of DNA replication can occur by binding a circular oligonucleotide to a site residing in the RNA template since such binding can block access to that site and to downstream sites, i.e. sites on the 3' side of the target site.

To initiate RNA transcription, RNA polymerase recognizes and binds to specific start sequences, or promoters, on a DNA template. Binding of RNA polymerase opens the DNA template. There are also additional transcriptional regulatory elements that play a role in transcription and are located on the DNA template. These transcriptional regulatory elements include enhancer sequences, upstream activating sequences, repressor binding sites and others. All such promoter and transcriptional regulatory elements, singly or in combination, are targets for the subject circular oligonucleotides. Oligonucleotide binding to these sites can block RNA polymerase and transcription factors from gaining access to the template and thereby regulating, e.g., increasing or decreasing, the production of RNA, especially mRNA and tRNA. Additionally, the subject oligonucleotides can be targeted to the coding region or 3'-untranslated region of the DNA template to cause premature termination of transcription. One skilled in the art can readily design oligonucleotides for the above target sequences from the known sequence of these regulatory elements, from coding region sequences, and from consensus sequences.

RNA transcription can be increased by, for example, binding a circular oligonucleotide to a negative transcriptional regulatory element or by inhibiting biosynthesis of a protein that can repress transcription. Negative transcriptional regulatory elements include repressor sites or operator sites, wherein a repressor protein binds and blocks transcription. Oligonucleotide binding to repressor or operator sites can block access of repressor proteins to their binding sites and thereby increase transcription.

The primary RNA transcript made in eukaryotic cells, or pre-mRNA, is subject to a number of maturation processes before being translocated into the cytoplasm for protein translation. In the nucleus, introns are removed from the pre-mRNA in splicing reactions. The 5' end of the mRNA is modified to form the 5' cap structure, thereby stabilizing the mRNA. Various bases are also altered. The polyadenylation of the mRNA at the 3' end is thought to be linked with export from the nucleus. The subject circular oligonucleotides can be used to block any of these processes.

A pre-mRNA template is spliced in the nucleus by ribonucleoproteins which bind to splice junctions and intron branch point sequences in the pre-mRNA. Consensus sequences for 5' and 3' splice junctions and for the intron branch point are known. For example, inhibition of ribonucleoprotein binding to the splice junctions or inhibition of covalent linkage of the 5' end of the intron to the intron branch point can block splicing. Maturation of a pre-mRNA template can, therefore, be blocked by preventing access to these sites, i.e. by binding circular oligonucleotides of this invention to a 5' splice junction, an intron branch point or a 3' splice junction. Splicing of a specific pre-mRNA template can be inhibited by using circular oligonucleotides with sequences that are complementary to the specific pre-mRNA splice junction(s) or intron branch point. In a further embodiment, a collection of related splicing of pre-mRNA templates can be inhibited by using a mixture of circular oligonucleotides having a variety of sequences that, taken together, are complementary to the desired group of splice junction and intron branch point sequences.

Polyadenylation involves recognition and cleavage of a pre-mRNA by a specific RNA endonuclease at specific polyadenylation sites, followed by addition of a poly(A) tail onto the 3' end of the pre-mRNA. Hence, any of these steps can be inhibited by binding the subject oligonucleotides to the appropriate site.

RNA translocation from the nucleus to the cytoplasm of eukaryotic cells appears to require a poly(A) tail. Thus, a circular oligonucleotide is designed in accordance with this invention to bind to the poly(A) tail and thereby block access to the poly (A) tail and inhibit RNA translocation. For such an oligonucleotide, both the P and AP domains can consist of about 10 to about 50 thymine residues, and preferably about 20 residues. Especially preferred P and AP domain lengths for such an oligonucleotide are about 6 to about 12 thymine residues.

Protein biosynthesis begins with the binding of ribosomes to an mRNA template, followed by initiation and elongation of the amino acid chain via translational "reading" of the mRNA. Protein biosynthesis, or translation, can thus be blocked or inhibited by blocking access to the template using the subject circular oligonucleotides to bind to targets in the template mRNA. Such targets contemplated by this invention include the ribosome binding site (Shine-Delgarno sequence), the 5' mRNA cap site, the initiation codon, and sites in the protein coding sequence. There are also classes of protein which share domains of nucleotide sequence homology. Thus, inhibition of protein biosynthesis for such a class can be accomplished by targeting the homologous protein domains (via the coding sequence) with the subject circular oligonucleotides.

Regulation of biosynthesis by any of the aforementioned procedures has utility for many applications. For example, genetic disorders can be corrected by inhibiting the production of mutant or over-produced proteins, or by increasing production of under-expressed proteins; the expression of genes encoding factors that regulate cell proliferation can be inhibited to control the spread of cancer; and virally encoded functions can be inhibited to combat viral infection.

In accordance with the present invention, it has been determined that in some instances the biosynthesis of a DNA, RNA or protein is more effectively regulated by binding the template at more than one target site. The present circular oligonucleotides which are prepared to bind to multiple target sites, e.g. by having more than one P or AP domain, can also be more effective at regulating the biosynthesis of a DNA, RNA or protein than oligonucleotides which can bind only one target site. For example, the binding of two sites within a gene can provide greater inhibition than achieved with single-site binding (Lisziewicz et al., 1992, Proc. Natl. Acad. Sci. USA 89:11209; Maher et al., 1987, J. Arch. Biochem. Biophys. 253:214–220; Tannock, I. F. in "The Basic Science of Oncology" 2nd ed.; Tannock, I. F. and Hill, R. P., eds. McGraw-Hill, New York, 348–349). In targeting viral sequences, the binding of two genes in a virus can inhibit viral replication more effectively than binding a single target. It has been shown, for example, that the use of multiple probes against a virus reduces the ability of the virus to escape inhibition by mutation (Kern et al. 1991 Science 252:1708–1711). A broader spectrum of inhibition by targeting two mutants of one virus or two viruses which are commonly found together, such as HIV-1 and cytomegalovirus (CMV) can also be achieved in accordance with the present invention.

Therefore, the present methods of regulating the biosynthesis of a DNA, RNA or protein can also include binding to more than one target within a template, whether the targets are bound by separate circular oligonucleotides or by the same oligonucleotide which includes multiple P or multiple AP domains.

Some types of genetic disorders that can be treated by the circular oligonucleotides of the present invention include Alzheimer's disease, beta-thalassemia, osteogenesis imperfecta, some types of arthritis, sickle cell anemia and others. Many types of viral infections can be treated by utilizing the circular oligonucleotides of the present invention, including infections caused by hepatitis, influenza, rhinovirus, HIV, herpes simplex, papilloma virus, cytomegalovirus, Epstein-Barr virus, adenovirus, vesicular stomatitus virus, rotavirus and respiratory syncytial virus among others. According to the present invention, animal and plant viral infections may also be treated by administering the subject oligonucleotides.

The c-myc gene is one example of a gene which can have a role in cell proliferation. Inhibition of c-myc expression has been demonstrated in vitro using a linear oligonucleotide complementary to a target 115 bp upstream of the c-myc transcription start site (Cooney et al., 1988, Science 241:456–459). Circular oligonucleotides of SEQ ID NO:1, and SEQ ID NO:2, as depicted below, are complementary to the c-myc promoter at nucleotides −131 to −120 and −75 to −62, respectively, and are provided to inhibit c-myc expression in accordance with the present invention. As used in these depictions of SEQ ID NO:1 and SEQ ID NO:2, N can be any nucleotide or nucleotide analog. Arrows indicate 5' to 3' directionality.

SEQ ID NO: 1

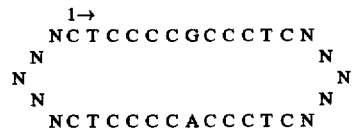

SEQ ID NO: 2

Chronic myeloid leukemia is a human malignant disease characterized by specific chromosomal translocations. The primary lesion in most cases is a reciprocal translocation between the long arms of chromosomes 9 and 22. This translocation results in the formation of a hybrid gene on chromosome 22 designated bcr-abl. The gene contains a 5' bcr portion and a 3' abl portion. Transcripts of this fusion gene appear to be primarily of two types, designated bcr exon 3/abl exon 2 and bcr exon 2/abl exon 2. These fusion genes are unique to the neoplastic cell and therefore make ideal targets for regulation by circular oligonucleotides.

Accordingly, the present invention provides two circular deoxyoligonucleotides capable of inhibiting proliferation of chronic myeloid leukemia cells, for example as set forth in SEQ ID NO: 36 and SEQ ID NO: 37. The circular deoxyoligonucleotide of SEQ ID NO: 36 is targeted toward a region in the bcr 3/abl 2 gene 385 nucleotides 5' to the bcr/abl junction and is depicted below.

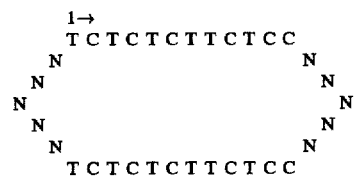

The circular deoxynucleotide of SEQ ID NO: 37 is targeted toward the bcr 2/abl 2 junction and is illustrated below.

Circular deoxyoligonucleotides of SEQ ID NO: 36 and SEQ ID NO: 37 significantly inhibit chronic myeloid leukemia cell proliferation when added directly to the cell culture medium of human K562 and BV173 cells, respectively. K562 cells (Lozzio et al., 1975, Blood 45:321) and BV173 cells (Pegoraro et al., 1983, Jour. Nat. Canc. Inst. 70:447) are model systems for the chromosomal translocations that characterize chronic myeloid leukemia. Accordingly, the circular oligonucleotides of the present invention are useful in inhibiting the proliferation of chronic myeloid leukemia cells. In vivo efficacy can be assessed in a suitable host by determining the numbers of myeloid leukemia cells before and after treatment.

Human immunodeficiency virus (HIV) is a retrovirus causing acquired immunodeficiency syndrome (AIDS). The circular oligonucleotides of this invention provide a means of blocking the replication of the virus without deleteriously affecting normal cellular replication in humans infected with HIV. The retroviral genome is transcribed as a single, long transcript, part of which is spliced to yield RNA encoding viral envelope proteins. Inhibition of HIV infection can be accomplished by designing oligonucleotides to bind to a number of regions within the HIV genome, including coding regions for functions that replicate the genome (i.e., the pol or reverse transcriptase function) or functions that control gene expression (e.g. the tat, rev or other functions). However, previous work with linear oligonucleotides has suggested that splice sites, poly(A) addition signals, cap or initiator codon sites, and sites implicated in ribosome assembly can be particularly effective for inhibiting eukaryotic protein expression. Furthermore, the terminal structures of the retroviral genome are also excellent targets for inhibiting retrovirus production not only because these structures encode control regions which mediate the rate of transcription and replication, but also because these structures are repeated, allowing an oligonucleotide to bind and block access to each repeat.

Accordingly, the present invention provides three circular oligonucleotides, set forth in SEQ ID NO:3, SEQ ID NO:4 and SEQ ID NO:41. SEQ ID NO:3 is complementary to a region of the gag start sequence (5'-CUAGAAGGAGAGAGAUGGGUGCGAGAG-3'; SEQ ID NO:42, wherein the target sequence is underlined). SEQ ID NO:4 is complementary to a region of the pol start sequence (5'-AUGGAAAAGGAAGGGAAAAUU-3', SEQ ID NO:43, wherein the target sequence is underlined). SEQ ID NO:41 is complementary to a polypurine tract in the HIV LTR (5'-UUUUAAAAGAAAAGGGGGGACUGG-3'; SEQ ID NO:44, wherein the target sequence is underlined). The circular form of SEQ ID NO:3 is depicted below, wherein nucleotide number 1 is the first nucleotide in the P domain, i.e., the first T on the top line corresponds to base 1.

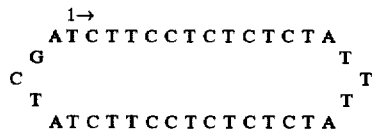

The circular form of SEQ ID NO:4 is depicted below wherein nucleotide number 1 is the first nucleotide of the P domain.

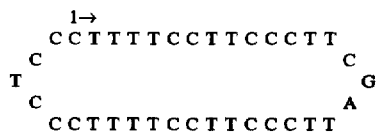

The circular form of SEQ ID NO:41 is depicted below wherein nucleotide number 1 is the first nucleotide of the P domain.

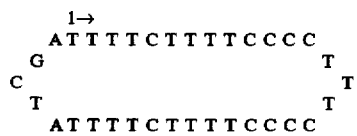

Circular oligonucleotides of SEQ ID NO:3 and SEQ ID NO:4 and SEQ ID NO: 41 can inhibit HIV infection both in vitro and in vivo. In vitro screening for circular oligonucleotide effectiveness against HIV infection permits one skilled in the art to judge the stability of oligonucleotide:target binding and to assess in vivo efficacy and binding stability. To observe in vitro inhibition circular oligonucleotides can be added to the growth medium of an appropriate cell line infected with HIV. Cells can be pretreated with the circular oligonucleotides or circular oligonucleotides can be added at the time of infection or after HIV infection. Addition before or after infection allows assessment of whether the subject oligonucleotide can prevent or simply inhibit HIV infection respectively.

The extent of inhibition of HIV infection or replication can be judged by any of several assay systems, including assessment of the proportion of oligonucleotide-treated cells surviving after infection relative to survival of untreated cells, assessment of the number of syncytia formed in treated and untreated HIV infected cells and determination of the amount of viral antigen produced in treated and untreated cells.

In vivo studies of the efficacy of circular oligonucleotides can be done in a suitable animal host, such as transgenic mice, immune deficient mice or chimpanzees. Levels of HIV antigens can be monitored to assess the effect of circular oligonucleotides on HIV replication and thereby to follow the course of the disease state. Alternatively, human volunteers with AIDS or ARC can be administered with the subject circular oligonucleotides since the oligonucleotides do not appear to be cytotoxic. The disease status of these volunteers can then be assessed to determine the efficacy of the subject oligonucleotides in treating and preventing AIDS infection.

A further aspect of this invention provides pharmaceutical compositions containing the subject circular oligonucleotides with a pharmaceutically acceptable carrier. In particular, the subject oligonucleotides are provided in a therapeutically effective amount of about 0.1 μg to about 100 mg per kg of body weight per day, and preferably of about 0.1 μg to about 10 mg per kg of body weight per day, to bind to a nucleic acid in accordance with the methods of this invention. Dosages can be readily determined by one of ordinary skill in the art and formulated into the subject pharmaceutical compositions.

As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The subject oligonucleotides may be administered topically or parenterally by, for example, by osmotic pump, intravenous, intramuscular, intraperitoneal subcutaneous or intradermal route, or when suitably protected, the subject oligonucleotides may be orally administered. The subject oligonucleotides may be incorporated into a cream, solution or suspension for topical administration. For oral administration, oligonucleotides may be protected by enclosure in a gelatin capsule. Oligonucleotides may be incorporated into liposomes or liposomes modified with polyethylene glycol or admixed with cationic lipids for parenteral administration. Incorporation of additional substances into the liposome, for example, antibodies reactive against membrane proteins found on specific target cells, can help target the oligonucleotides to specific cell types.

Moreover, the present invention contemplates administering the subject circular oligonucleotides with an osmotic pump providing continuous infusion of such oligonucleotides, for example, as described in Rataiczak et al. (1992 Proc. Natl. Acad. Sci. USA 89:11823–11827). Such osmotic pumps are commercially available, e.g., from Alzet Inc. (Palo Alto, Calif.). Topical administration and parenteral administration in a cationic lipid carrier are preferred.

The following examples further illustrate the invention.

EXAMPLE 1

Circularization of Oligonucleotides Using an End Joining Oligonucleotide

According to the present invention, a simple one-step chemical method has been developed to construct circles from linear precursors (precircles). A DNA oligonucleotide was constructed which had the same sequence as the eventual target; this is the end-joining-oligonucleotide. A precircle oligonucleotide was then constructed and chemically phosphorylated on the 5'-end or 3'-end. As depicted in FIG. 1, the precircle and end-joining-oligonucleotide were mixed and allowed to form a complex in which the ends were adjacent. Cyanogen bromide, imidazole buffer, and a divalent metal were added. After incubation for 6–48 hr, the mixture was dialyzed, lyophilized, and the products were separated by denaturing 20% polyacrylamide gel electrophoresis. UV shadowing revealed major bands which comigrated with the precircle and the end-joining-oligonucleotide, along with one new product which migrated slightly more slowly than the precircle. No product was observed without added end-joining-oligonucleotide or in the absence of a 5'- or 3'-phosphate group on the precircle. The major bands were excised and eluted from the gel, dialyzed to remove salts and quantitated by absorbance at 260 nm. For reactions with precircles 1 and 2 (SEQ ID NO:5 and SEQ ID NO:6, respectively), using end-joining-oligonucleotides 4 and 5 (SEQ ID NO:8 and SEQ ID NO:9, respectively), the circles 6 and 7 were obtained in 40% and 58% yields, respectively. The sequences of each of these molecules and other oligonucleotides are depicted in FIG. 2.

The circular structure of products 6 and 7 was confirmed by resistance to 3' exonuclease digestion and to 5' dephosphorylation under reaction conditions in which a linear precircle was completely destroyed or dephosphorylated. Accordingly, the 3' exonuclease activity of T4 DNA polymerase cleaved linear precircles 1 and 2, but not circles 6 and 7. The linear precircles were also 5'-end labeled with $^{32}P$ and then circularized. After reaction, the circular products were inert to calf alkaline phosphatase whereas the precircles completely released labeled $^{32}P$. The slightly slower gel mobility of the circles relative to the precircles was consistent with the occurrence of circularization.

Optimal Circularization Conditions

Many parameters were optimized to increase yields of the circular product, including oligonucleotide and precircle concentrations, temperature, reaction time, metal, metal concentration, BrCN concentration and pH. Improved circularization conditions provided an at least two-fold higher yield of circles compared to prior art conditions wherein two single-stranded oligonucleotides were joined (Luebke et al., 1989, J. Am. Chem. Soc. 111:8733 and Kanaya et al., 1986, Biochemistry 25:7423). These improved conditions were:

50 µM precircle
55 µM end-joining-oligonucleotide
100 mM $NiCl_2$
200 mM imidazole HCl (pH 7.0)
125 mM BrCN
25° C., 36 hr.

However circle closure was also effective under the following conditions:

3–200 µM precircle
3–200 µM end-joining-oligonucleotide
10–500 mM $NiCl_2$
50–500 mM imidazole-HCl
20–200 mM BrCN
4°–37° C., 6–48 hr.

Other metals ($Zn^{2+}$, $Mn^{2+}$, $Co^{2+}$, $Cu^{2+}$, $Pb^{2+}$, $Ca^{2+}$, $Mg^{2+}$) also work in place of $Ni^{2+}$. Additionally, the reaction is pH sensitive.

Closure in AP and P Domains

Closure of a circle in the AP domain was superior to closure in the P domain. Comparison of the circularization of precircles 2 and 3 (SEQ ID NO:6 and SEQ ID NO:7, respectively) around the same end-joining-oligonucleotide (i.e. 5, SEQ ID NO:9) indicated that circle 7 (having SEQ ID NO:6) was formed with a 58% yield when closed in the AP domain (i.e. using precircle 2) and only a 35% yield when closed in the P domain (i.e. using precircle 3).

Condensing Reagents

Figure 3:
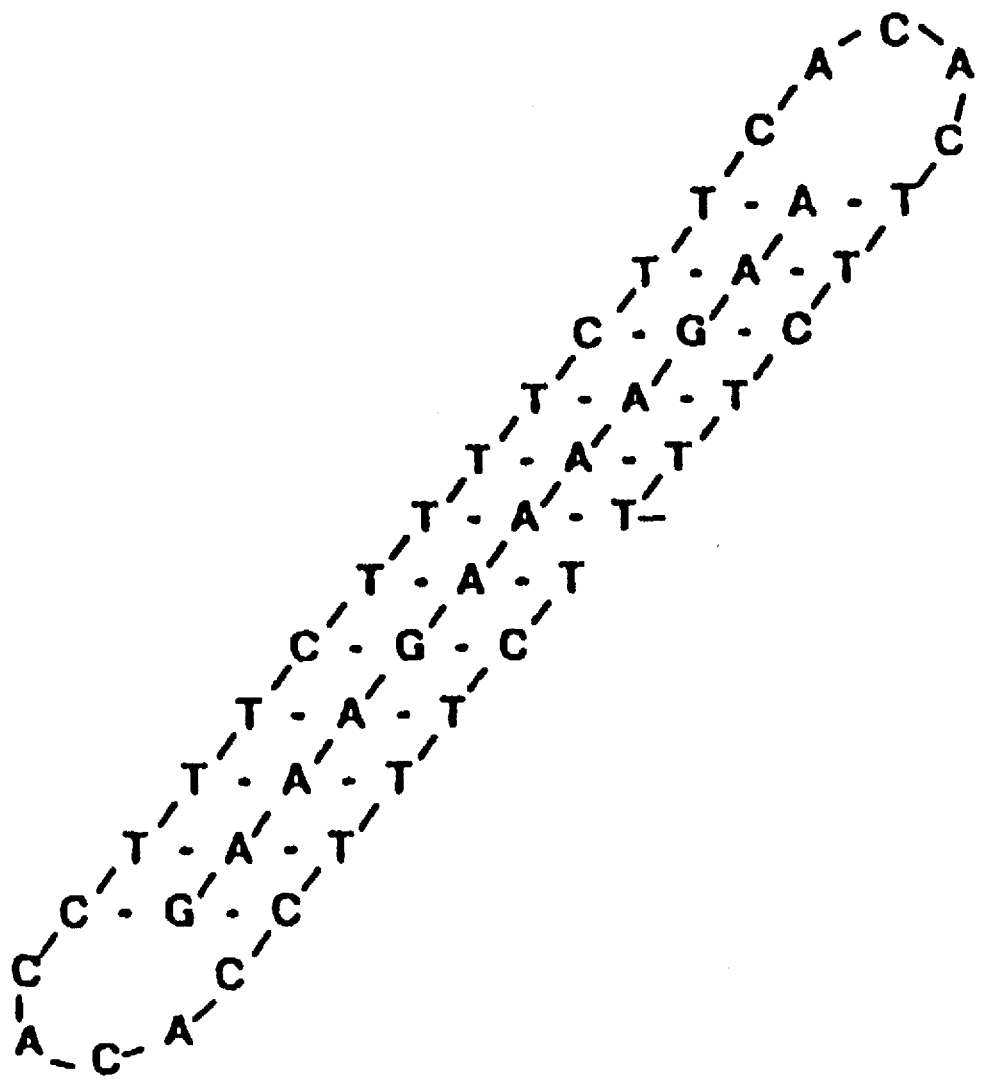
FIG. 3 depicts the structure of a linear precircle complexed with an end-joining-oligonucleotide before ligation.

Two reagents have been commonly used for chemical ligation of DNA and RNA, BrCN/imidazole/$NiCl_2$ and 1-ethyl-3-(3-dimethylaminopropyl)carbodiimide (EDC) (Kanaya et al. 1986 Biochemistry 25:7423 and Ashley et al. 1991 Biochemistry 30:2927). Therefore, these reagents were directly compared for efficacy in ligating a precircle to circular oligonucleotide 6 (FIG. 3 and SEQ ID NO:5) using a $dA_{12}$ (SEQ ID NO:8) end-joining-oligonucleotide.

BrCN/imidazole/$NiCl_2$ was used under the established optimal conditions except that ligation efficiency was observed at both 4° C. and 25° C. EDC was used at 200 mM with 20 mM $MgCl_2$, 50 mM MES (pH 6.0) at 4° C. or 25° C. with incubation for 4 days.

At 4° C. BrCN was more efficient, yielding 95% circular product while EDC yielded only 55% product. However, at 25° C. both EDC and BrCN yielded 95% product. Therefore, BrCN is more effective at lower temperatures but either EDC or BrCN can be used with equal success at 25° C. However, BrCN has an additional advantage over EDC since ligation with BrCN requires 24 hr or less while ligation with EDC requires about 4 days.

Use of a 5'- or 3'-Phosphate

Under different ligation conditions joining a 3'-phosphate with a 5'-OH yielded more ligated product than joining a 5'-phosphate with a 3'-OH (Ashley, et al.).

Therefore, the percent conversion to circular oligonucleotide 6 (SEQ ID NO: 5; FIG. 2) by a 5'-phosphate or by a 3'-phosphate precircles was compared:

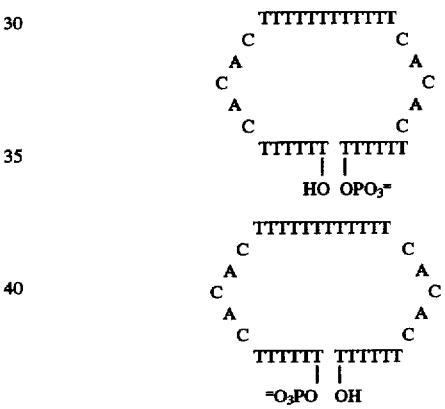

Circularization reactions were performed using a $dA_{12}$ end-joining-oligonucleotide (SEQ ID NO: 8) and the established optimal conditions, except that 5 nmoles of precircle and end-joining-oligonucleotide were used. Products were visualized under UV light after separation by denaturing gel electrophoresis.

Conversion to circular product was 60% (±5%) when a 5'-phosphate was present and 95% when a 3'-phosphate was present. No increase in yield was observed when increased reaction times or increased reagent concentrations were used.

Accordingly, use of a 3'-phosphate rather than a 5'-phosphate improves circularization.

EXAMPLE 2

Circular Oligonucleotides Bind Containing P and AP Domains Bind Target Nucleic Acids with Higher Affinity Than Do Linear Oligonucleotides The binding affinities of circles 6 and 7 (SEQ ID NO:5 and SEQ ID NO:6, respectively) for their targets were measured by comparison of the melting temperatures of the circular and linear complexes. Solutions contained 1:1 ratios of oligonucleotide and target (3 μM each) in 100 mM NaCl, 10 mM MgCl$_2$, and 10 mM Tris-HCl (pH 7.0). Mixing curves measured at 260 nm confirmed that 1:1 complexes were formed. The free energies ($-\Delta G°_{37}$) of the complexes were derived from the melting data using a two-state curve-fitting method (Petersheim, et al., 1983, Biochemistry 22:256).

The results show that the circular oligonucleotides containing P and AP domains bound to their targets more strongly than did linear precircles or Watson-Crick complementary target-sized oligonucleotides (Table 2). For example, target 4 (SEQ ID NO:8) formed a duplex with its target-sized Watson-Crick complement having a T$_m$ of 37.1° C. while the precircle 1:target 4 complex (i.e. SEQ ID NO:5 bound to SEQ ID NO:8) had a T$_m$ of 44.7° C. By comparison, circle 6, having the same sequence as precircle 1, bound to target 4 with a T$_m$ of 57.5° C. and a free energy of binding that was 8.6 kcal/mol more favorable than the corresponding Watson-Crick duplex. The corresponding association constant at 37° C. is $6 \times 10^{11}$ M$^{-1}$, which is more than six orders of magnitude greater than for the Watson-Crick duplex. A similar effect was observed for the binding of circle 7 (SEQ ID NO:6) to target 5 (SEQ ID NO:9); this complex had a T$_m$ of 62.3° C., whereas the corresponding Watson-Crick duplex melted at 43.8° C. These data indicate that the binding of circular oligonucleotides containing P and AP domains to a single stranded target is stronger than the binding of a linear oligonucleotide to a corresponding target.

To determine the binding characteristics when the target sequence was embedded within a longer sequence, a 36 nucleotide oligonucleotide was synthesized with a 12 base target sequence (equivalent to target 4) in the middle. Melting studies revealed that circle 6 bound to this longer oligonucleotide more strongly than it did to a target having the same size as the binding domains of the circle: the Tm of circle 6 with target 4 was 59.8° C. whereas with the 36 base oligonucleotide containing an embedded target the Tm was 63.4° C. Therefore the binding strength of circles with embedded targets was higher than that with binding-domain-sized-targets.

TABLE 2

| oligonucleotide: target | complex | T$_m$, °C. | $-G°_{37}$(kcal/mol) |
|---|---|---|---|
| | 3'-TTTTTTTTTTTT<br>5'-AAAAAAAAAAAA | 37.1 | 8.1 |
| | 3'-TTCTTTTCTTTC<br>5'-AAGAAAAGAAAG | 43.8 | 10.3 |
| 1:4 | TTTTTTTTTTTT<br>C          C<br>A          A<br>C  AAAAAAAAAAAA  C<br>A          A<br>C          C<br>TTTTTT TTTTTT<br>        \|<br>      OPO$_3^-$ | 44.7 | 10.5 |

TABLE 2-continued

| oligonucleotide: target | complex | T$_m$, °C. | $-G°_{37}$(kcal/mol) |
|---|---|---|---|
| 3:5 | TTCTTTTCTTTC<br>C          C<br>A          A<br>C  AAGAAAAGAAAG  C<br>A          A<br>C          C<br>TTCTTT TCTTTC<br>        \|<br>      OPO$_3^-$ | 47.0 | 10.8 |
| 6:4 | →<br>TTTTTTTTTTTT<br>C          C<br>A          A<br>C  AAAAAAAAAAAA  C<br>A          A<br>C          C<br>TTTTTTTTTTTT<br>→ | 57.4 | 16.7 |
| 7:5 | →<br>TTCTTTTCTTTC<br>C          C<br>A          A<br>C  AAGAAAAGAAAG  C<br>A          A<br>C          C<br>TTCTTTTCTTTC | 62.3 | 16.4 |

EXAMPLE 3

Circular Oligonucleotides Bind Target More Selectively Than Linear Oligonucleotides In order to measure the sequence selectivity of circular oligonucleotides, a set of target oligonucleotides with one variable base was constructed. Binding energies for a circle complexed with these targets were measured; the selectivity was defined by the free energy difference between the correct sequence and mismatched sequences. The selectivity obtained with the circular structure was then directly compared to the selectivity of an analogous linear oligonucleotide.

DNA oligonucleotides were machine synthesized using the β-cyanoethyl phosphoramidite method. Circular oligonucleotide 8 was prepared from a linear precircle having SEQ ID NO:7:

5'-pTCTTTCCACACCTTTCTTTTCTTCACACTTC

TTT and was cyclized by assembly around an end-joining oligonucleotide having the sequence 5'-AAGAAAAGAAAG (SEQ ID NO:9) using BrCN/imidazole to close the final bond, as described in Example 1. The circular structure was confirmed by its resistance to a 3'-exonuclease and 5'-phosphatase.

The sequence selectivity of circle 8 was measured by hybridizing it with targets which contained a single mismatched base and determining the strength ($\Delta G°_{37}$) of the resulting complexes by thermal denaturation. Eight targets (SEQ ID NO: 38 and 39) were synthesized which were complementary to circle 8 (SEQ ID NO: 7) and linear oligonucleotide 9 (SEQ ID NO: 10) except for a single centrally positioned variable base (X or Y=A, G, C, T). Four targets have a variable base X which is matched with two opposing T's in the circle, resulting in a T-X-T triad. In the remaining four targets, the variable base Y is matched with two opposing C's in the circle, giving a C-Y-C triad. For comparison to this circle complex, a linear oligonucleotide 9 (SEQ ID NO: 10) was used; resulting in a duplex with a central T-X pair in the first four experiments or a C-Y pair in the remaining four.

| complex (X,Y = A,T,G,C) | expt. no. |
|---|---|
| 3'-T T C T T T T C T T T C<br>5'-A A G A X A A G A A A G | 1–4 |
| →<br>A C T T C T T T T C T T T C C A<br>C   A A G A X A A G A A A G   C<br>A C T T C T T T T C T T T C C A | 5–8 |
| 3'-T T C T T T T C T T T C<br>5'-A A G A A A A Y A A A G | 9–12 |
| →<br>A C T T C T T T T C T T T C C A<br>C   A A G A A A A Y A A A G   C<br>A C T T C T T T T C T T T C C A | 13–16 |

Thermal denaturation of the sixteen complexes was carried out in the presence of 10 mM $MgCl_2$, 100 mM NaCl, and 10 mM Tris·HCl (pH 7.0), with target and circular or linear oligonucleotide concentrations at 3 μM each. Experiments were carried out in duplicate and the results averaged. Oligonucleotide:target complex melting was monitored at 260 nm. The temperature vs. absorbance curves so generated showed a single transition from bound to free oligonucleotide. Free energies of association were obtained by fitting the data with a two-state curve-fitting method. The results were checked in two cases by measuring the association energies by the van't Hoff method; good agreement was seen between the two methods. Selectivities are defined as the difference in free energies ($\Delta G$) of complexation between matched and mismatched oliogmers.

Table 3 displays the results of the mismatch experiments. Experiments 1–4 show the effects of a T—X target mismatch on a DNA duplex. As expected, the true match (X=A) gives the most favorable complex ($-\Delta G°_{37}$=10.3 kcal/mol); the mismatches (X=G, C, T) result in a loss of 3.2–4.4 kcal/mol in binding energy, in good agreement with published mismatch studies. Experiments 5–8, by comparison, show the effects of a T—X—T mismatch on circle complex binding strength. Once again, the true match (X=A) gives the most favorable three stranded complexes ($-\Delta G°_{37}$=16.4 kcal) However, target mismatches (X=G, T, C) result in a considerably larger loss of binding energy (6.2–7.6 kcal/mol) for a circular oligonucleotide than for a linear oligonucleotide.

Similarly, experiments 9–12 give the effects of a C—Y mismatch on the two stranded duplex. The matched base (Y=G) gives a free energy of duplex association of –10.3 kcal/mol. The mismatches (Y=A, T, C) result in a loss of 5.2 to 5.8 kcal/mol of binding energy, in reasonable agreement with published data. By contrast, the effects of a C—Y—C mismatch are greater in a three stranded complex (experiments 13–16): the match (Y=G) gives a binding energy of –16.4 kcal/mol, and the mismatches (Y=A, T, C) are less stable by 7.1 to 7.5 kcal/mol.

Thus, in all the cases studied, the circular ligand shows greater selectivity for its correctly matched sequence than does the standard linear oligomer. The selectivity advantage ranges from 1.3 to 2.2 kcal/mol for the C—Y—C series to 3.0 to 3.4 kcal/mol for the T—X—T series. These are quite significant differences, considering they arise from a single base Change; in the T—X—T series, the circular oligonucleotide is nearly twice as selective as the linear oligonucleotide. This selectivity difference corresponds to one to two orders of magnitude in binding constant at 37° C.

There are two factors which may explain this high selectivity. First, because two domains of the circular oligonucleotide bind the central target strand, the circular oligonucleotide, in effect, checks the sequence twice for correct matching. Secondly, protonation of cytosine within a C+G—C triad may also be a factor in increasing selectivity. This protonation is likely to be favored only when there is base triad formation wherein guanine can share the positive charge; evidence suggests that the pKa of cytosine within a base triad is 2–3 units higher than that of free deoxycytosine. The addition of this positive charge may lessen the negative charge repulsions arising from the high density of phosphates in the complex and thereby increase binding stability.

Therefore, circular oligonucleotides containing a P and AP domain, as described herein, have both higher binding affinity and higher selectivity for single-stranded targets than can be achieved with Watson-Crick duplexes alone.

TABLE 3

| | expt. # | variable base | $T_m$,°C. | $-\Delta G°_{37}$ (kcal/mol) | Selectivity (kcal/mol) |
|---|---|---|---|---|---|
| duplex | 1 | X = A | 43.8 | 10.3 | — |
| | 2 | X = G | 33.8 | 7.1 | 3.2 |
| | 3 | X = C | 28.3 | 5.9 | 4.4 |
| | 4 | X = T | 31.1 | 6.4 | 3.9 |
| circle complex | 5 | X = A | 62.3 | 16.4 | — |
| | 6 | X = G | 44.2 | 10.2 | 6.2 |
| | 7 | X = C | 39.8 | 8.8 | 7.6 |
| | 8 | X = T | 40.8 | 9.1 | 7.3 |
| duplex | 9 | Y = A | 26.2 | 5.1 | 5.2 |
| | 10 | Y = G | 43.8 | 10.3 | — |
| | 11 | Y = C | 22.2 | 4.5 | 5.8 |
| | 12 | Y = T | 27.0 | 5.0 | 5.3 |
| circle complex | 13 | Y = A | 39.9 | 9.0 | 7.4 |
| | 14 | Y = G | 62.3 | 16.4 | — |
| | 15 | Y = C | 41.3 | 9.3 | 7.1 |
| | 16 | Y = T | 39.6 | 8.9 | 7.5 |

EXAMPLE 4

Factors Effecting Complex Formation

Figure 4:
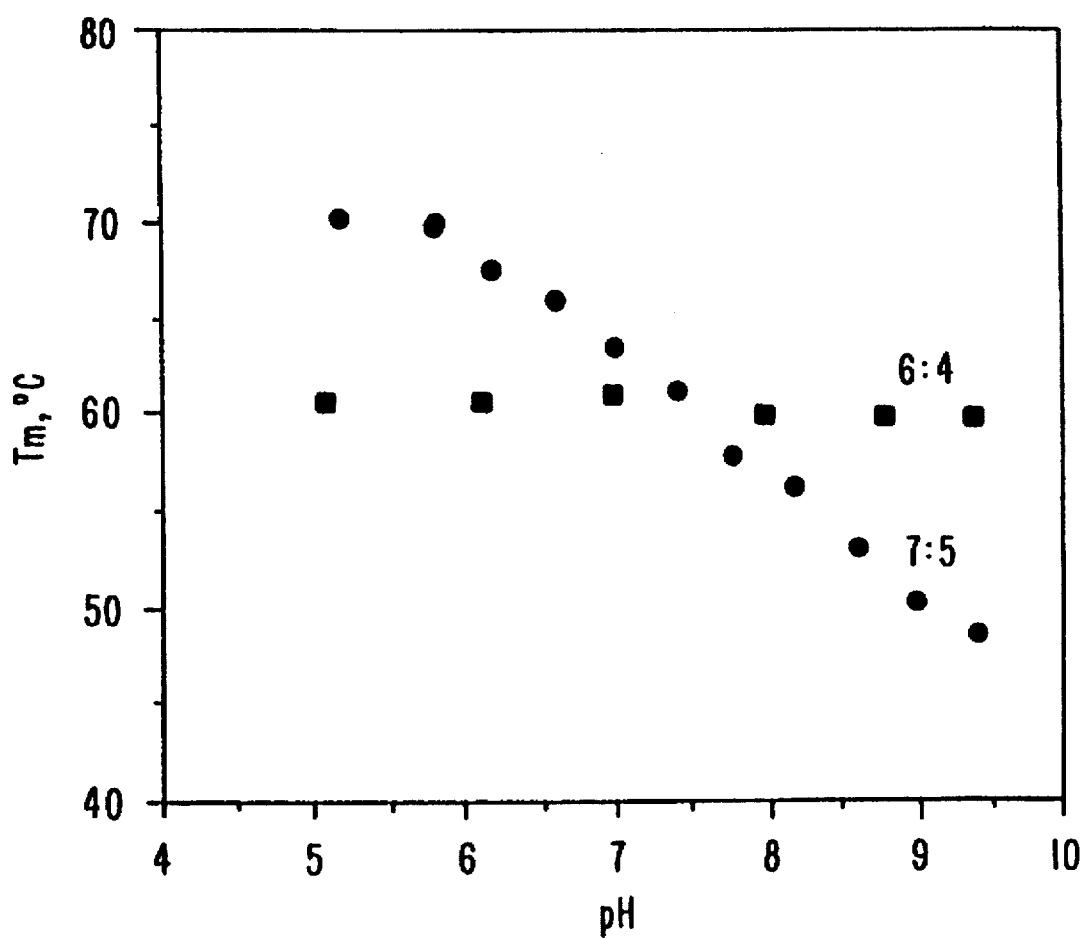
FIG. 4 depicts the effect of pH on circular oligonucleotide:target complex formation as measured by $T_m$. Filled circles represent the stability at different pH values for a 6:4 complex while filled squares depict the stability of a 7:5 complex. The sequences of circular oligonucleotides 6 and 7 and targets 4 and 5 are presented in FIG. 3.

1) Solution effects. The effects of NaCl, $Mg^{2+}$, spermine, and pH on circle:target complexes were examined. Circles with cytosines in the binding domains are sensitive to pH, and exhibited greater stability at lower pH values. However, these and other circle:target complexes are quite stable at the physiological pH of 7.0–7.4 (FIG. 4). The complexes show salt concentration sensitivity comparable to duplexes; however, small amounts of $Mg^{2+}$ or spermine increase the complex stability markedly. For example, in a concentration of 1 mM $Mg^{++}$ at pH 7.0, with no added salts, a stable 7:5 circle:target complex formed having a $T_m$ of 58° C. When a solution of 20 μm spermine containing no added salts was used the 7:5 complex again formed stably with a $T_m$ of 56° C. Both $Mg^{++}$ and spermine are present in at least these concentrations in mammals, and so circle:target complexes will be stable under physiological conditions.

2) Loop size. The optimum number of nucleotides for the loop domain of a circle was determined by observing complex formation between a target and circles with different loop sizes. Precircle linear oligonucleotides similar to precircle 1 were synthesized with 2, 3, 4, 5, 6 and 10 base loops using an arbitrary sequence of alternating C and A residues. Each of these precircles was designed to bind to the $A_{12}$ template (i.e. target 4 (SEQ ID NO:8)). The $T_m$'s for circles with 4, 5, 6 and 10 base loops showed that a five-nucleotide loop size was optimum for the circle binding either to template $A_{12}$ or to a longer 36mer sequence containing the $A_{12}$ binding site (see FIG. 5A).

Figure 5B:
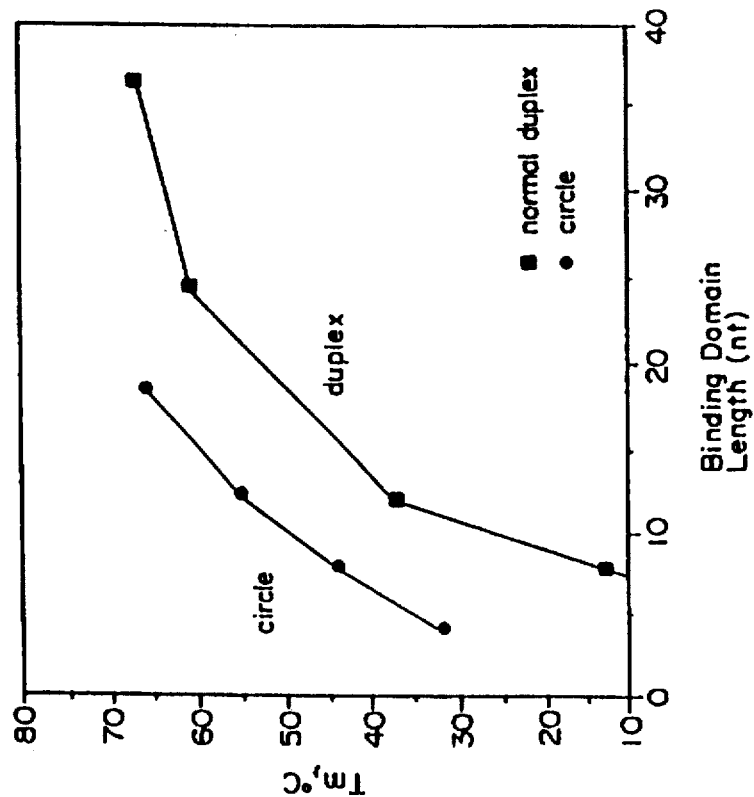
FIG. 5B depicts the effect of target and binding domain length on complex formation.
Figure 5A:
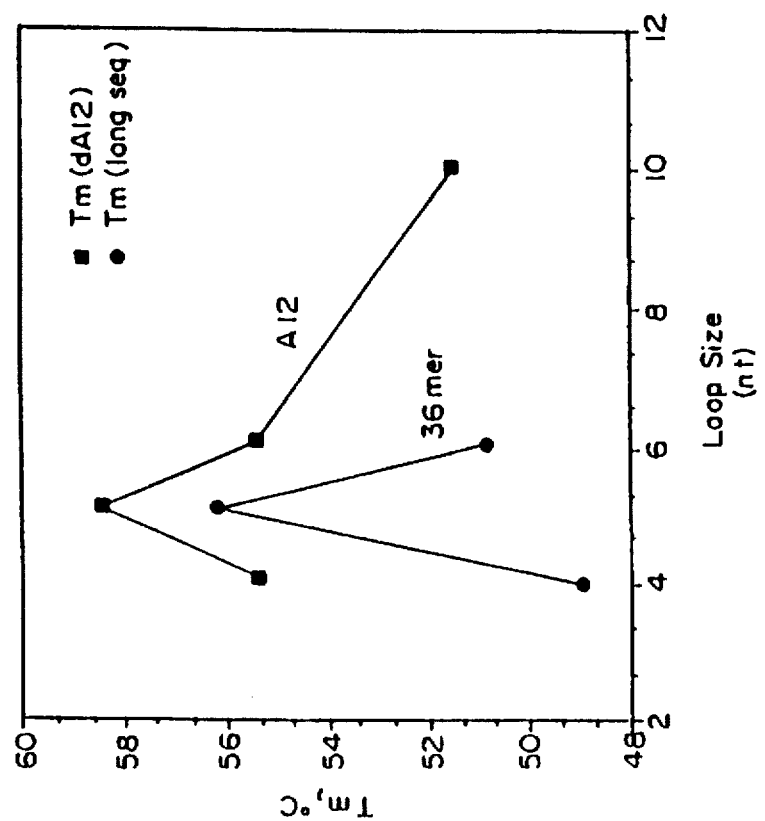
FIG. 5A depicts the effect of loop size on complex formation, with a comparison between binding to two targets: a simple $(dA)_{12}$ target (squares) and a 36 nucleotide oligonucleotide target (circles).
Figure 6:
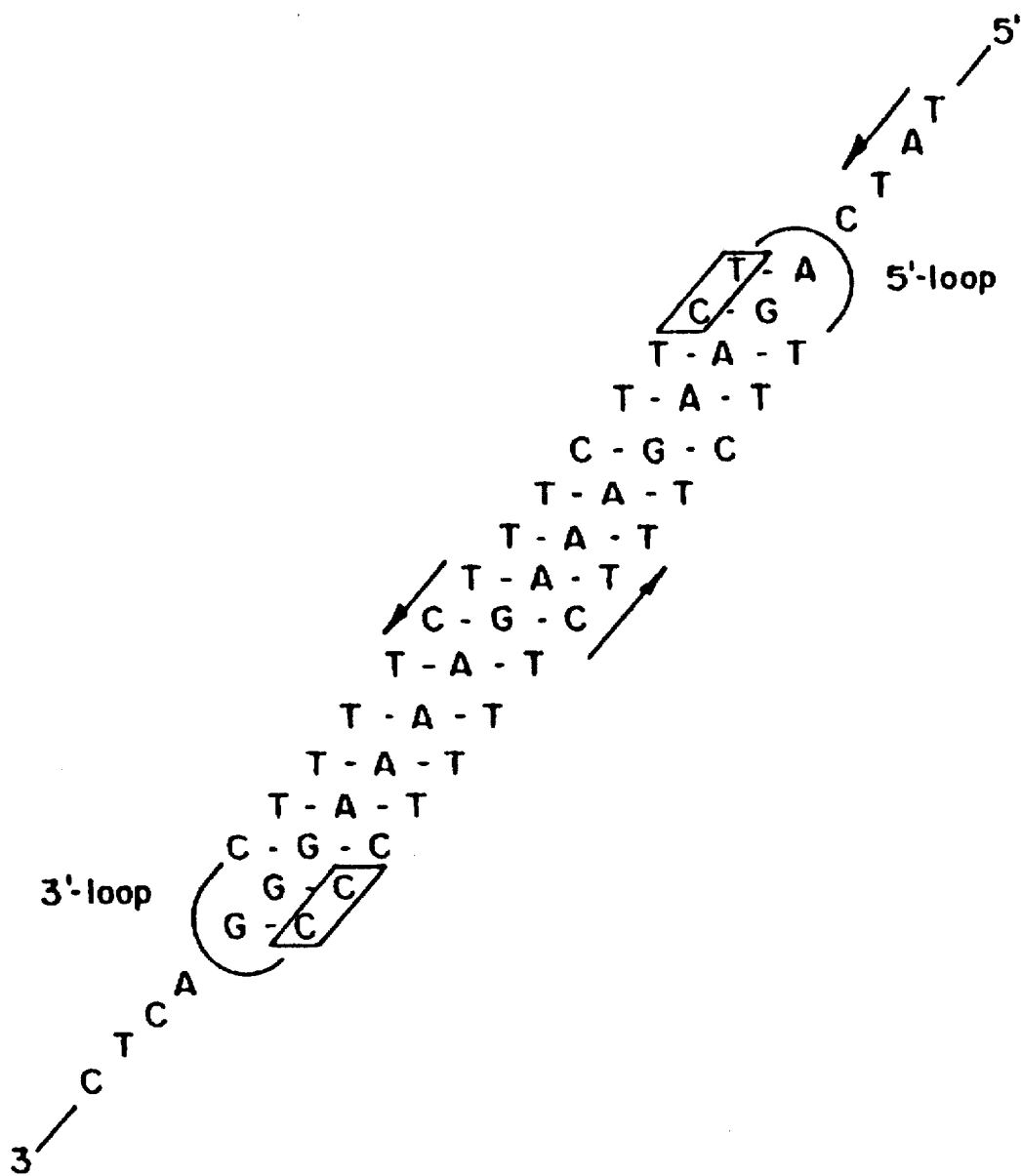
FIG. 6 depicts a complex formed between a circular oligonucleotide and a target where the P and AP binding domains are staggered on the target.

3) Binding Domain length. The effect of circular oligonucleotide binding domain length on circle:target complex melting temperature was compared to melting of duplexes having the same length. Circles with various size binding domains were constructed and complexed with single-stranded $dA_n$ targets for n equal to 4, 8, 12 and 18 nucleotides. FIG. 5B illustrates that considerably higher $T_m$'s were observed for circle:target complexes relative to Watson-Crick duplexes having the same length as the binding domains (determined in 0.1M NaCl, pH 7). For example, a 12-base circular complex melted at about the same temperature as a 24-base duplex. The 4-base circular complex melted at 34° C. whereas the corresponding Watson-Crick duplex $T_m$ was less than 0° C.

4) Methylation. It has been known for some time that methylation at the C-5 position of cytosine, forming the naturally-occurring base m5C, raises the $T_m$ of duplex DNA in which it occurs, relative to unmethylated sequences (Zmudzka et al., 1969, Biochemistry 8:3049). In order to investigate whether addition of this methyl group would stabilize circle:target complexes, two analogs of circle 7 (having SEQ ID NO:6) were synthesized. In one circle, the six C's in the binding domains were methylated leaving the loop unmethylated ($Me_6$). In the second circle, all twelve C's were methylated ($Me_{12}$). Melting temperatures for the complexes of these methylated circle with target 5 were measured. The $Me_6$ complex had a $T_m$ of 71.1° C. (compared to 61.8° C. for the unmethylated circle), and the $Me_{12}$ circle had a $T_m$ of 72.4° C. Thus, use of the natural base $m^5C$ in place of C increased stability substantially, and in one case resulted in a 12-base complex which melted 10.6° C. higher than an unmethylated circle and 28.6° C. higher than the corresponding unmethylated Watson-Crick duplex.

EXAMPLE 5

Replacement of Nucleotide Loop Domains with Non-Nucleotide Loop Domains

The loop domains of circular oligonucleotides were replaced with polyethylene or oligoethylene glycol chains of different lengths and the effect of such synthetic loops upon circular oligonucleotide binding and nuclease resistance was assessed.

Methods

Circular oligonucleotides were synthesized having tetra-, penta-, or hexa-ethylene glycol chain loop domains. In each case the ethylene glycol chain was synthetically prepared for automated DNA synthetic procedures using the method of Durand et al. (1990, Nucleic Acids Res. 18:6353–6359). Briefly, a phosphoramidite was placed on a hydroxy group at one end of the ethylene glycol chain and a dimethoxytrityl (DMT) moiety was placed on the other terminal ethylene glycol hydroxy group. This derivatized ethylene glycol chain was then added to the growing linear oligonucleotide at the appropriate step of automated DNA synthesis. Circularization steps were performed by procedures described in Example 1. A linear oligonucleotide precircle having a tetraethylene loop domain was not efficiently circularized. This result indicates that a tetraethylene loop domain may be too short for optimal binding to a target.

Two types of linear oligonucleotides were used as target binding domains for the circular oligonucleotides: Target I was a 12-base oligonucleotide having no non-target nucleotides and Target II was a 36-base oligonucleotide having a 12-base target within it. The target sequences utilized were 5'-AAGAAAAGAAAG-3' (SEQ ID NO:9) and 5'-AAAAAAAAAAAA-3' (SEQ ID NO:8), the latter is termed a poly($dA)_{12}$ target sequence.

The melting temperatures ($T_m$) of circular oligonucleotides with polyethylene loops were observed at pH 7.0 (10 mM Tris-HCl) in 10 mM $MgCl_2$ and 100 mM NaCl. Each linear target and each circular oligonucleotide was present at a 3 μM concentration.

Results

The $T_m$ of a circular oligonucleotide having a CACAC nucleotide loop sequence and a poly($dT)_{12}$ sequence for both P and AP domains was 57.8° C. when bound to a poly ($dA)_{12}$ target sequence. The $T_m$ of a circular oligonucleotide having the same P and AP domain sequences but hexaethylene glycol loop domains was 51.4° C. when bound to the same target.

A comparison of $T_m$ values observed for circular oligonucleotides having pentaethylene glycol (PEG) and hexaethylene glycol (HEG) loop domains is depicted in Table 4A.

TABLE 4A

| Complex | | | Target I Tm | Target II Tm |
|---|---|---|---|---|
| PEG | p TTCTTTTCTTTCp<br>AAGAAAAGAAAG<br>p TTCTTTTCTTTCp | PEG | 51.5 | 47.5 |
| HEG | p TTCTTTTCTTTCp<br>AAGAAAAGAAAG<br>p TTCTTTTCTTTCp | HEG | 58.0 | 51.1 |
| HEG | p TTTTTTTTTTTTp<br>AAAAAAAAAAAA<br>p TTTTTTTTTTTTp | HEG | 51.4 | 46.5 |

The $T_m$ value observed for a circular oligonucleotide having a HEG loop is about 4.5° C. higher than that of a circular oligonucleotide with a PEG loop. Therefore, circular oligonucleotides with hexaethylene glycol loop domains bind with greater stability than do circular oligonucleotides with tetra- or penta-ethylene glycol loops.

Figure 7A:
FIG. 7A presents the sequences of complexes of long and short targets with circular oligonucleotides containing polyethylene glycol linkers.
Figure 7B:
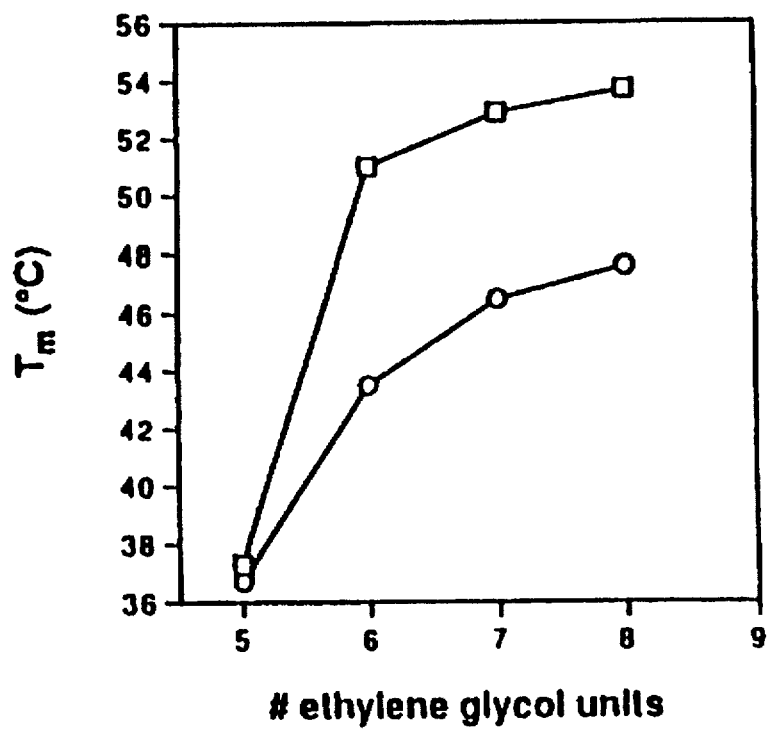
FIG. 7B depicts the effect of length of ethylene glycol loop on binding affinity of circular oligonucleotides for short and long targets.

In a second experiment, circular oligonucleotides having penta-, hexa-, septa- or octoethylene glycol chain loop domains were synthesized as described above and compared to circular nucleotides having nucleotide loop domains. Circular oligonucleotides were assessed for binding to a short target (5'-AAGAAAAGAAAG, SEQ ID NO: 9) representing a minimal binding domain that allows the loops to bridge the pyrimidine domains without interference from the central point strand. Circular oligonucleotides were further assessed for binding to an extended target (5'-GGACTCTATCAGAAGAAAAGAAAGGGACTCTATCAG, SEQ ID NO: 40) in order to test the interactions of the loop with the central strand as it extends outward from the complex (FIG. 7A). Results depicted in Table 4B and FIG. 7B show that binding affinity increases with increasing linker length up to the maximum length of the $EG_8$-linked compound. When the circular oligonucleotides are hybridized to the same target site embedded in a longer sequence, the same length-dependent trend is observed, with a preference for the longest ($EG_8$) linker.

TABLE 4B

Melting Temperatures ($T_m$) and free energies ($-\Delta G°_{37}$) for triple helical complexes bridged by oligoethylene glycol (EG) loops or by a pentanucleotide loop at pH 7.0.

| loop structure | $T_m^{a,b}$ (°C.) | $-\Delta G°_{37}^{a,b}$ (kcal) |
|---|---|---|
| TTCTTTTCTTTC AAGAAAAGAAAG TTCTTTTCTTTC | | |
| EG$_5$ | 37.3 | 8.8 |
| EG$_6$ | 51.0 | 15.6 |
| EG$_7$ | 52.9 | 16.6 |
| EG$_8$ | 53.7 | 17.0 |
| —CACAC— | 52.2 | 14.1 |
| TTCTTTTCTTTC 5' GGACTCTATCA GAAGAAAAGAAAGG GACTCTATCAG 3' TTCTTTTCTTTC | | |
| EG$_5$ | 36.8 | 8.8 |
| EG$_6$ | 43.5 | 11.7 |
| EG$_7$ | 46.5 | 13.0 |
| EG$_8$ | 47.6 | 13.9 |
| —CACAC— | 52.2 | 14.6 |

[a]Conditions: 2.0 µM total strand concentration, 100 mM NaCl, 10 mM MgCl$_2$, 10 mM Na-PIPES buffer.
[b]Error limits for individual measurements are estimated at ±0.5° C. in $T_m$ and ±10% in free energy.

Nuclease Resistance

Circular oligonucleotides were tested for nuclease resistance when unbound and when bound to a target oligonucleotide. All circular oligonucleotides, whether bound or unbound, were completely resistant to exonucleases. Endonuclease sensitivity was assessed using S1 nuclease according to the manufacturer's suggestions.

A comparison of the resistance of bound and unbound circular oligonucleotides to S1 nuclease is depicted in Table 5.

TABLE 5

| Oligonucleotide | Time For 50% S1 Cleavage |
|---|---|
| HEG pTTCTTTTCTTTCp HEG <br> pTTCTTTTCTTTCp | 1 min. |
| HEG pTTCTTTTCTTTCp <br> AAGAAAAGAAAG HEG <br> pTTCTTTTCTTTCp | >24 h |
| ACTTCTTTTCTTTCCA <br> C                C <br> ACTTCTTTTCTTTCCA | 1 min. |
| ACTTCTTTTCTTTCCA <br> C  AAGAAAAGAAAG  C <br> ACTTCTTTTCTTTCCA | 40 min. |

These data indicate that unbound circular oligonucleotides are vulnerable to S1 nuclease. However, when bound to a target, a circular oligonucleotide having a polyethylene loop domain is much more resistant to S1 nuclease, at least 36-fold more resistant, than a circular oligonucleotide with a nucleotide loop domain.

The nuclease resistance of circular and linear oligonucleotides was also compared when these oligonucleotides were incubated in human plasma for varying time periods. Circular oligonucleotide 7 and the precursor to this circle, linear oligonucleotide 2, were incubated at a 50 µM concentration in plasma at 37° C. Aliquots were removed at various time points and cleavage products were separated by gel electrophoresis. Nuclease resistance was assessed by observing whether degradation products were evident on the gels.

When incubated in human plasma the half-life of linear oligonucleotide 2 was 20 min. In contrast, circular oligonucleotide 7 underwent no measurable nuclease degradation during a 48 hr incubation. Accordingly, the half-life of a circular oligonucleotide is greater than 48 hr in human plasma, i.e. more than 140 times longer than a linear oligonucleotide having an equivalent sequence.

EXAMPLE 6

Circular Deoxyoliognucleotides Selectively Bind DNA

The experimental data presented in this example demonstrate that circular deoxyoligonucleotides preferentially bind to linear DNA targets over their RNA counterparts.

Two sets of linear DNA and RNA target oligonucleotides were synthesized:

| Sequence 1: | rAAAAAAAAAAAA (SEQ ID. NO. 11) | dAAAAAAAAAAAA (SEQ ID. NO. 8) |
|---|---|---|
| Sequence 2: | rAAGAAAGAAAAG (SEQ ID. NO. 12) | dAAGAAAGAAAAG (SEQ ID. NO. 13) |

The following complementary circular RNA (SEQ. ID. NO. 23 and 25) and DNA (SEQ. ID. NO. 5 and 26) probes were synthesized. Underlined residues in the circular RNAs lack a 2'-OH and thus differ from completely RNA strands by a single 2' hydroxyl group. Arrows indicate 5' to 3' directionality. Use of deoxynucleotides in this position was done to ensure the isomeric purity of the circles.

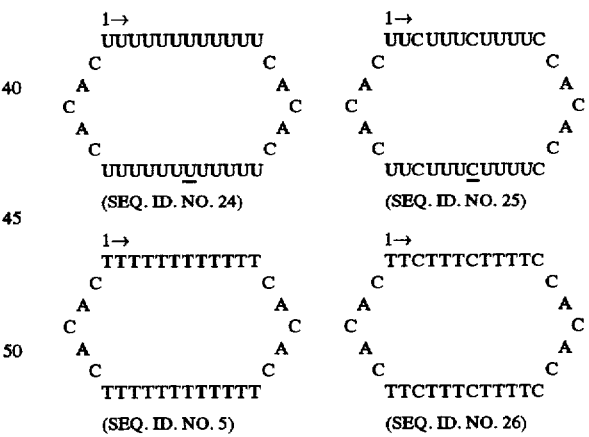

DNA oligonucleotides were synthesized on a Pharmacia LKB automated synthesizer or an Applied Biosystems 392 synthesizer using standard β-cyanoethylphosphoramidite chemistry as described by Beaucage et al., 1981, Tetrahedron Lett. 22:1859. RNA oligonucleotides were prepared using t-butyl-dimethylsilyl-protected phosphoramidites (Applied Biosystems), and following the oligoribonucleotide synthesis procedure of Scaringe et al. (1990) Nucleic Acids Res. 18:5433. For the synthesis of the 34mer RNAs to be cyclized, 2'-deoxynucleoside supports (dU-CPG and dC-CPG, Glen Research) were used in the synthesis, so that the 3'-end residue lacks a 2'-OH group. 5'-phosphorylation was carried out with a phorphoramidite reagent described by Horn et al., 1986, Tetrahedron Lett. 27:4705 purchased from Glen Research. Tetrabutylammonium fluoride in THF (Aldrich) was dried over molecular sieves prior to use in the desilylation step. Oligomers were purified by preparative 20% denaturing polyacrylamide gel electrophoresis and quantitated by absorbance at 260 nm. Molar extinction coefficients for the oligomers were calculated by the nearest neighbor method.

Circularization of linear precursors was achieved by non-enzymatic template-directed cyclization as described in Example 1. The reactions contained 50 µM precircle, 55 µM template strand, 200 mM imidazole•HCl (from a pH 7.0 stock), 100 mM $NiCl_2$. BrCN was added last as a solid to the mixture to give a final calculated concentration of 125 mM. Reactions were dialyzed against water and lyophilized. Purification of the circular products was carried out using preparative denaturing PAGE.

The ability of the circular probes to bind to linear targets was examined by thermal denaturation studies. Solutions for the thermal denaturation studies contained a one-to-one ratio of 34-nucleotide circular pyrimidine oligomer and 12-nucleotide complementary purine oligomer (1.5 µM each). Also present were 100 mM NaCl and 10 mM $MgCl_2$. Solutions were buffered with 10 mM Na•PIPES (1,4-piperazine-bis(ethanesulfonate), Sigma) at pH 7.0 or 5.5. The buffer pH is that of a 1.4×stock solution at 25° C. containing the buffer and salts. After the solutions were prepared they were heated to 90° C. and allowed to cool slowly to room temperature prior to the melting experiments.

The melting studies were carried out in teflon-stoppered 1 cm pathlength quartz cells under nitrogen atmosphere on a Varian Cary 1 UV-vis spectophotometer equipped with thermoprogrammer. Absorbance (260 nm) was monitored while temperature was raised from 5° to 80° C. at a rate of 0.5° C./min.; a slower heating rate did not affect the results. In all cases the complexes displayed sharp, apparently two-state transitions, with all-or-none melting from bound complex to free oligomers. Melting temperatures ($T_m$) were determined by computer fit of the first derivative of absorbance with respect to 1/T. Uncertainty in $T_m$ is estimated at ±0.5° C. based on repetitions of experiments.

Free energy values were derived by computer-fitting the denaturation data, using the two-state approximation for melting described by Petersheim et al., 1983, Biochemistry 22:256.

Melting temperatures ($T_m$) and free energy values for the association of the circular probes with their target strands at pH 7.0 and 5.5 are presented in Table 6.

Data for the binding of the circular oligonucleotide probes to RNA and DNA targets of Sequence 1 at pH 7 indicate that the RNA probes bind DNA and RNA with similar high affinity. The RNA-RNA-RNA complex (RRR) exhibits a free energy of association of 11.7 kcal while that for the RNA-DNA-RNA complex (RDR) is 11.2 kcal. Thus, the all RNA complex is favored by 0.5 kcal.

Data for the binding of circular DNA probes to RNA and DNA of target Sequence 1 at pH 7.0 demonstrate that circular DNA probes preferentially bind to DNA targets. The free energy of association for the all DNA complex (DDD) is 8.9 kcal greater than that for the complex of the circular DNA and the RNA target (DRD). Likewise, the all DNA complex exhibits a $T_m$ value 30° higher than that of the DRD complex.

None of the free energy or $T_m$ values for the oligonucleotide complexes involving DNA or RNA of target Sequence 1 show any pH dependence (Table 6). This is expected since no CGC triads are present in these complexes.

Inspection of the data for the binding of circular probes to DNA and RNA of target Sequence 2 at neutral pH again indicates that RNA probes bind to RNA and DNA ligands with similar high affinity (Table 6). The all RNA complex has a $T_m$ of 51.2° C. and a free energy of 12.6 kcal while that of the RDR complex is 48.5° C. and 11.8 kcal. Formation of the all RNA complex is slightly favored.

Data for the binding of DNA probes to RNA and DNA targets of Sequence 2 at pH 7.0 also support the conclusion that DNA circles selectively bind to DNA targets. The free energy of association for the all DNA complex is 14.5 kcal while that for the DRD complex is only 10.4 kcal.

All complexes except the DRD complex exhibit a pH dependent increase in $T_m$ and free energy of association (Table 6). Such a pH dependent increase in affinity is indicative of the presence of a triple helix and is due to the protonation of C residues and the formation of C+GC triads. Triplexes of this type are very stable at lower pH and this stability is reflected in the higher $T_m$ and free energy values. The fact that the DNA—RNA—DNA complex does not display any pH dependence indicates that this complex may not be triple helical in nature.

In summary, the results illustrated above clearly demonstrate that circular RNA probes bind to RNA and DNA ligands. RNA probes exhibit a slight preference for binding RNA. Circular DNA probes exhibit a strong preference for binding DNA ligands. The overall order of affinity for binding of RNA and DNA circles with RNA and DNA complements for the two sequences studied in this example is DDD>>RRR>RDR>>DRD. One can take significant advantage of these binding preferences by selectively targeting DNA over RNA, in vivo or in vitro.

TABLE 6

Melting transition temperatures ($T_m$(°C.)) and free energies ($-\Delta G°_{37}$(kcal/mol)) for complexes of two circular RNAs and two circular DNAs with complementary purine RNA and DNA single strands at two pH values. Underlined residues in circular RNAs lack a 2'-OH.

| Complex | Type | pH = 7.0 $T_m$(°C.) | pH = 7.0 $-\Delta G°_{37}$(kcal) | pH = 5.5 $T_m$(°C.) | pH = 5.5 $-\Delta G°_{37}$(kcal) |
|---|---|---|---|---|---|
| → UUUUUUUUUUUU<br>C               C<br>A               A<br>C rAAAAAAAAAAAA C<br>A               A<br>C               C<br>UUUUUU<u>U</u>UUUUU | RNA<br><br>RNA<br><br>RNA | 48.2 | 11.7 | 48.7 | 11.8 |
| → UUUUUUUUUUUU<br>C               C<br>A               A<br>C dAAAAAAAAAAAA C<br>A               A<br>C               C<br>UUUUUU<u>U</u>UUUUU | RNA<br><br>DNA<br><br>RNA | 45.5 | 11.2 | 46.4 | 11.2 |
| → TTTTTTTTTTTT<br>C               C<br>A               A<br>C dAAAAAAAAAAAA C<br>A               A<br>C               C<br>TTTTTTTTTTTT | DNA<br><br>DNA<br><br>DNA | 53.6 | 15.0 | 54.1 | 15.7 |
| → TTTTTTTTTTTT<br>C               C<br>A               A<br>C rAAAAAAAAAAAA C<br>A               A<br>C               C<br>TTTTTTTTTTTT | DNA<br><br>RNA<br><br>DNA | 23.6 | 6.1 | 20.4 | 6.1 |
| → UUCUUUCUUUUC<br>C               C<br>A               A<br>C rAAGAAAGAAAAG C<br>A               A<br>C               C<br>UUCUUU<u>C</u>UUUUC | RNA<br><br>RNA<br><br>RNA | 51.2 | 12.6 | 62.9 | 17.7 |
| → UUCUUUCUUUUC<br>C               C<br>A               A<br>C dAAGAAAGAAAAG C<br>A               A<br>C               C<br>UUCUUU<u>C</u>UUUUC | RNA<br><br>DNA<br><br>RNA | 48.5 | 11.8 | 62.3 | 16.4 |
| → TTCTTTCTTTTC<br>C               C<br>A               A<br>C dAAGAAAGAAAAG C<br>A               A<br>C               C<br>TTCTTTCTTTTC | DNA<br><br>DNA<br><br>DNA | 55.5 | 14.5 | 69.7 | 21.2 |

TABLE 6-continued

Melting transition temperatures ($T_m$(°C.)) and free energies ($-\Delta G°_{37}$(kcal/mol)) for complexes of two circular RNAs and two circular DNAs with complementary purine RNA and DNA single strands at two pH values. Underlined residues in circular RNAs lack a 2'-OH.

| Complex | Type | pH = 7.0 | | pH = 5.5 | |
|---|---|---|---|---|---|
| | | $T_m$(°C.) | $-\Delta G°_{37}$(kcal) | $T_m$(°C.) | $-\Delta G°_{37}$(kcal) |
| →<br>TTCTTTCTTTTC<br>C           C<br>A           A<br>C rAAGAAAGAAAAG C<br>A           A<br>C           C<br>TTCTTTCTTTTC | DNA<br><br><br>RNA<br><br><br>DNA | 44.0 | 10.4 | 42.0 | 10.1 |

EXAMPLE 7

Strand Replacement By Circular Oligonucleotides

To test whether a circular oligonucleotide can readily dissociate duplex DNA and displace one strand of a duplex DNA target, the kinetics of strand displacement were observed for a duplex DNA target in the presence of a complementary linear or circular oligonucleotide.

A DNA duplex target with a fluorescein group on one strand and a tetramethylrhodamine group on the other strand was prepared using published procedures (Cardullo et al., 1988, Proc. Natl. Acad. Sci. USA 85:8790; Cooper et al., 1990, Biochemistry 29:9261). The structure of the duplex target (SEQ ID NO.:15) was as follows:

5'-fluorescein-A A A A A A A A A A A A 3'-rhodamine-T T T T T T T T T T T T.

The $T_m$ of this labeled duplex target was normal, therefore the fluorescent substituents had no significant effect upon association kinetics. Moreover, the emission maxima of the fluorescein-$dA_{12}$ strand was 523 nm while the emission maxima of the rhodamine-$dT_{12}$ strand was 590 nm, allowing the association kinetics of the two strands to be separately monitored.

Strand displacement reactions were done at 10° C. in a 1 cm fluorescence cuvette. Reaction conditions were 100 mM NaCl, 10 mM Mg Cl$_2$ and 10 mM Tris-HCl, pH 7.0 with a reaction volume of 3 ml. Labeled duplex was allowed to equilibrate for at least 1 hr at 10° C. before addition of a 100-fold excess of linear or circular oligonucleotide. A Spex Flurolog F 111A fluorescence instrument with 5 mm slit widths was used. An excitation wavelength of 450 nm and a monitored emission wavelength of 523 nm was used. The results were independent of both excitation and monitored emission wavelengths. Reactions were followed for at least 5 half-lives.

Addition of rhodamine-$dT_{12}$ to fluorescein-$dA_{12}$ caused a decrease in fluorescein fluorescence and an increase in rhodamine fluorescence. Such effects are due to energy transfer between the fluorescent moieties (Cardullo et al.).

The association rate constant of the two fluorescently-labeled strands was determined by mixing the strands under pseudo-first order conditions and monitoring the rate of decrease in fluorescein emission. At 10° C. the observed association constant was 3.2×10$^6$ M$^{-1}$ sec$^{-1}$ which agrees well with published rates of association for DNA oligonucleotides (Nelson et al. 1982 Biochemistry 21:5289; Turner et al. 1990 in Nucleic Acids (subvolume C), W. Saenger, Ed. Springer-Verlag, Berlin:201–227).

To compare the rates at which a single linear strand (SEQ ID NO.:8) or a circular oligonucleotide having SEQ ID NO.:5 (i.e. circular oligonucleotide 6) exchanged with strands in a duplex DNA, an excess of an unlabeled linear or circular oligonucleotide was mixed with the fluorescently-labeled duplex DNA target. The increase in fluorescein emission was then observed at a temperature significantly below the $T_m$ of the duplex target as a measure of duplex target strand dissociation.

Figure 8:
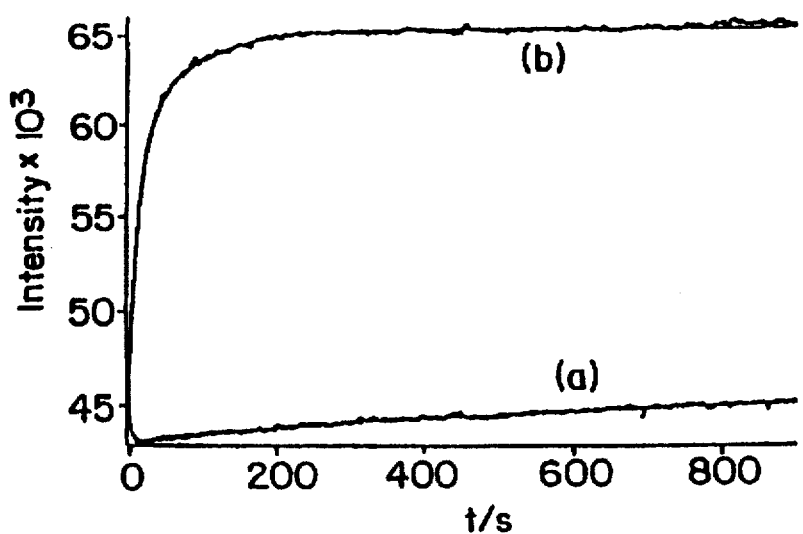
FIG. 8 depicts replacement of one strand of a fluorescently labeled double stranded target (SEQ ID NO:11) by either a linear oligonucleotide having SEQ ID NO:8 (a) or a circular oligonucleotide having SEQ ID NO:5 (b). Strand replacement was measured by an increase in fluorescein fluorescence intensity (Y-axis) as a function of time (X-axis).

FIG. 8 depicts a typical kinetic run for the reaction of the preformed labelled 1:1 duplex (0.01 μmol dm$^{-3}$) with unlabelled d(A)$_{12}$ strand (1.0 μmol dm$^{-3}$) at 10° C. The observed first-order rate constant was similar for the addition of either unlabelled d(A)$_{12}$ or d(T)$_{12}$ single strands and was independent of unlabelled strand concentration (0.1–0.4 μmol dm$^{-3}$). Under the reaction conditions, the exchange is a slow process, with a half-life of 58 min. at 10° C., which is 30° C. below the melting temperature for the duplex. This reflects the slow rates at which even short duplexes dissociate.

In contrast to the above behavior, when the complementary circle was instead added to the duplex, the rate of increase in the fluorescein emission was considerably faster (FIG. 8). The experimental first-order-rate constant for the reaction of duplex with added circle (100-fold excess) at 10° C. was 2.3×10$^{-2}$s$^{-1}$, a half-life of only 30s.

Figure 9:
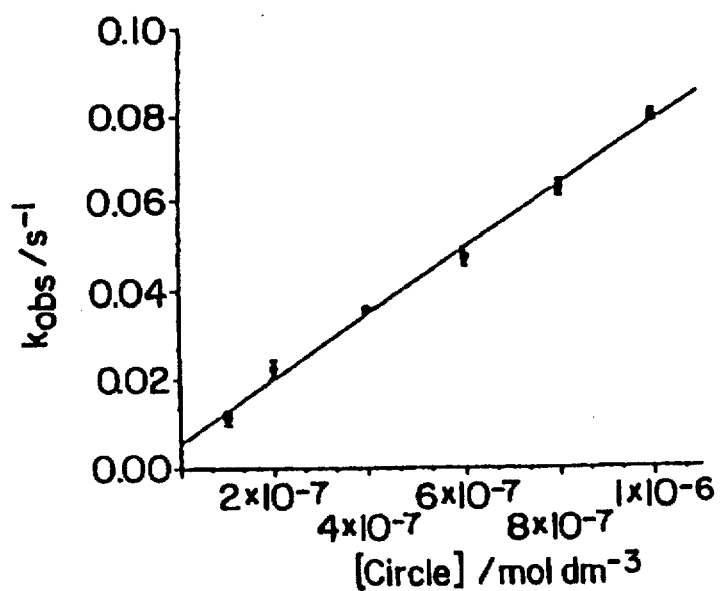
FIG. 9 depicts a plot of observed pseudo-first order rate constant, $K_{obs}$ for duplex target (SEQ ID NO:5) at several circle concentrations. Uncertainty in rate constants are no more than ±10%.

The rate of this reaction was dependent on the concentration of added circle (FIG. 9): a plot of [circle] vs. k$_{obs}$ is linear with a slope of 7.3×10$^4$ dm$^3$ mol$^{-1}$s$^{-1}$.

The second-order rate constant, 7.3×10$^4$ dm$^3$ mol$^{-1}$s$^{-1}$, for duplex dissociation by circle is similar to literature values for triple-helix formation. (Porschke et al., 1971, J. Mol. Biol. 62:361.) Saturation kinetics were not observed. The rate constant for dissociation, k$_2$, is greater than 0.08s$^{-1}$, the largest observed rate constant. This experiment demonstrates that it is possible to design a synthetic DNA molecule which can bind to duplex DNA by active displacement of the secondary structure.

EXAMPLE 8

Binding Properties of a Circular Oligonucleotide Having More Than One Pair of Binding Domains A circular oligonucleotide having two pairs of binding domains was synthesized. Such a circular oligonucleotide selectively bound one of two targets depending upon the pH of the hybridization reaction.

Materials and Methods

Oligonucleotide Synthesis

Oligonucleotides were synthesized using β-cyanoethylphosphoramidite chemistry (Beaucage et al.

1981Tetrahedron Lett. 22:1859). The concentration of oligonucleotide was determined by absorbance at 260 nm; extinction coefficients were calculated by the nearest neighbor method (Borer 1975 in *Handbook of Biochemistry and Molecular Biology* G. D. Fasman, ed. CRC Press: Cleveland, p. 589).

An oligonucleotide having SEQ ID NO:16 (5'-dTCTCTTTTTTTTTTTCTCTCTCTTTTTTTTTTTCTCp) was synthesized and circularized by the template-directed cyclization reaction described in Example 1 and in Prakash et al. (1992 J. Am. Chem. Soc. 114:3523). The end-joining-oligonucleotide employed for circularization had SEQ ID NO:17 (5'-dAAAGAGAGAGAAA). Conversion to circle was greater than or equal to 95% as assessed by UV-shadowing of the reaction mixture electrophoresed through a 20% denaturing polyacrylamide gel.

The circular oligonucleotide product having SEQ ID NO:18 was obtained from a polyacrylamide gel slice containing the slower moving band. To purify the circular oligonucleotide, the gel slice was crushed and dialyzed against water. The circularity of the oligonucleotide was tested by exposing the preparation to an exonuclease (T4 polymerase, Promega) under conditions leading to complete degradation of a linear oligonucleotide to mononucleotides. The SEQ ID NO:18 oligonucleotide was completely resistant to such exonuclease treatment.

The SEQ ID NO:18 circular oligonucleotide contained two pairs of nine base binding domains. One pair of binding domains (pair I) bound a target oligonucleotide having SEQ ID NO:19 (5'-dAGAGAGAGA), while the other pair of binding domains (pair II) bound a target oligonucleotide having SEQ ID NO:20 (5'-dAAAAAAAAA).

A thirty three nucleotide oligonucleotide was also synthesized which contained two target binding sites, one for the pair I and one for the pair II binding domains of the SEQ ID NO:18 circular oligonucleotide. This thirty three nucleotide oligonucleotide had SEQ ID NO:21 i.e. 5'-dCACA AGAGAGAGAATCCCTAAAAAAAAAAAACAC wherein the two target sites are indicated by underlining.

Two linear oligonucleotides complementary to the target sites within the SEQ ID NO:21 oligonucleotide were also synthesized: an oligonucleotide having SEQ ID NO:22 (5'-dTCTCTCTCT) and an oligonucleotide having SEQ ID NO:23 (5'-dTTTTTTTTT).

Thermal Denaturation Procedures

Thermal denaturation experiments with the circular oligonucleotide having SEQ ID NO:18 and the two target oligonucleotides having SEQ ID NO:19 and SEQ ID NO:20 were performed as described in Example 2. In particular, 1.5 µM of target oligonucleotide and 1.5 µM of circular oligonucleotide was placed in a buffer containing 100 mM NaCl, 10 mM MgCl$_2$ and 10 mM Na-PIPES (from Signa Chemical Co.). To assess the effect of pH upon binding, thermal denaturation experiments were performed using pH values varying from 5.5 to 9.0.

To generate thermal denaturation profiles of hyperchromicity vs. temperature the reaction mixture was first placed in a 1 cm-pathlength stoppered quartz microcell under nitrogen. The absorbance of the reaction mixture was recorded at 260 nm using a Cary 1 spectrophotometer when the temperature was increased at a rate of 0.5° C./min. The $T_m$ was assigned as the temperature of the inflection point in the denaturation curve. Measurement precision was ±0.5° C. as determined by observation of $T_m$ variability in several experiments.

Stoichiometric Determinations

The proportion of SEQ ID NO:18 circular oligonucleotide added to either SEQ ID NO:19 or SEQ ID NO:20 targets was varied in mixing experiments to determine the mole fraction of circular oligonucleotide present at complete complexation of target with circular oligonucleotide. To detect binding by observing a change in hyperchromicity using absorbance readings at 260 nm, the total DNA concentration was maintained at 4.5 µM while the proportion of circular oligonucleotide to target was varied.

Under such conditions, a change in the slope of the observed absorbance vs circular oligonucleotide mole fraction indicates that no further binding of target will occur as the proportion of circular oligonucleotide is increased. Therefore the inflection point in such a curve provides the mole fraction at which complete complexation has occurred. If the inflection point is approximately 0.5 then half of the oligonucleotide present in the hybridized complex is the circular oligonucleotide and half is a target oligonucleotide. Accordingly a mole fraction of about 0.5 for complete complexation indicates the stoichiometry of circular oligonucleotide to target is 1:1.

When the mole fraction for complete complexation is less than 0.5, more circular oligonucleotide than target oligonucleotide is present in the complex, e.g., a mole fraction of 0.33 means that two circular oligonucleotides are present per target. Therefore the stoichiometry of circular oligonucleotide to target in the complex will be greater than 1:1. Similarly, when the mole fraction for complete complexation is more than 0.5, less circular oligonucleotide than target oligonucleotide is present in the complex and the stoichiometry of circular oligonucleotide to target will be less than 1:1, e.g. a mole fraction of 0.66 means that one circular oligonucleotide and two targets are present.

Figure 10A:
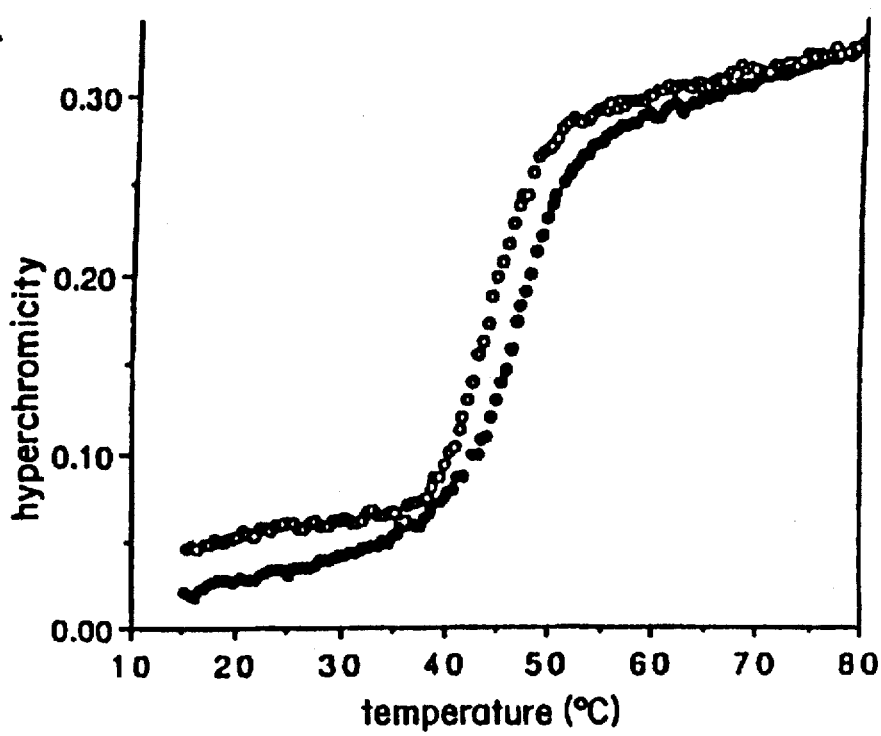
FIG. 10A depicts plots of the observed hyperchromicity (at 260 nm) as the temperature is increased for a circular oligonucleotide having two sets of binding domains and SEQ ID NO:18 when bound to either a target oligonucleotide having SEQ ID NO:19 (open circles) or to a target oligonucleotide having SEQ ID NO:20 (filled circles). These data indicate the melting temperature $(T_m)$ of the SEQ ID NO:18-SEQ ID NO:19 complex is 44.5° C. and the $T_m$ of the SEQ ID NO:18-SEQ ID NO:20 complex is 47.5° C.

Binding of SEQ ID NO:18 Circular Oligonucleotide to SEQ ID NOS:19–21 Targets At pH 7.0 the circular oligonucleotide having SEQ ID NO:18 bound target SEQ ID NO:19 with a $T_m$ of 44.5° C. (FIG. 10A, open circles) and an estimated free energy of association at 37° C. of −11.2 kcal/mole. Under similar conditions the circular oligonucleotide (SEQ ID NO:18) bound target SEQ ID NO:20 with a $T_m$ of 47.5° C. (FIG. 10A, filled circles) and a free energy of association at 37° C. of −13.2 kcal/mole. Accordingly the circular oligonucleotide had roughly the same affinity for target SEQ ID NO:19 and SEQ ID NO:20.

Figure 10B:
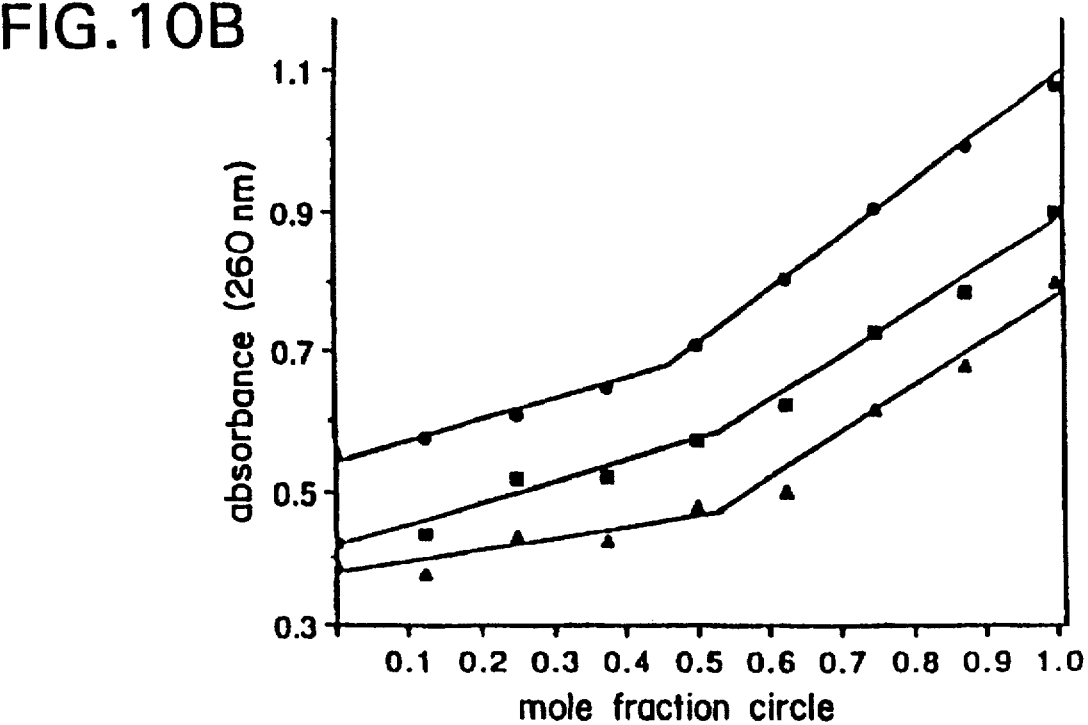
FIG. 10B depicts the mole fraction of the (SEQ ID NO:18) circular oligonucleotide having two pairs of binding domains versus the absorbance, when mixed with the SEQ ID NO:19 target (squares), the SEQ ID NO:20 target (triangles) or when mixed with a 1:1 combination both SEQ ID NO:19 and SEQ ID NO:20 targets (circles). The inflection point of the observed absorbance provides the mole fraction of SEQ ID NO:18 circular oligonucleotide needed for complete complexation with the indicated target oligonucleotides.

FIG. 10B depicts the mole fraction of SEQ ID NO:18 circular oligonucleotide present in a mixture of target and circular oligonucleotide versus the absorbance of that mixture. The mole fraction of SEQ ID NO:18 circular oligonucleotide when fully complexed with SEQ ID NO:19 target (squares) or SEQ ID NO:20 target (triangles) was 0.52 or 0.53, respectively. Similarly, when SEQ ID NO:18 circular oligonucleotide was mixed with a 1:1 combination both SEQ ID NO:19 and SEQ ID NO:20 targets (circles) the mole fraction circular oligonucleotide bound was 0.47 (FIG. 10B). Therefore, there was no significant difference in mole fraction of circular oligonucleotide bound when only one or when both targets were present. Accordingly, the stoichiometry of circular oligonucleotide to target in the hybridized complex was 1:1 whether one or both targets were present. These data indicate that the circular oligonucleotide undergoes a conformational change upon binding and that a single target is bound. These data further indicate and that binding of both targets by a single SEQ ID NO:18 circular oligonucleotide is precluded.

Figure 11A:
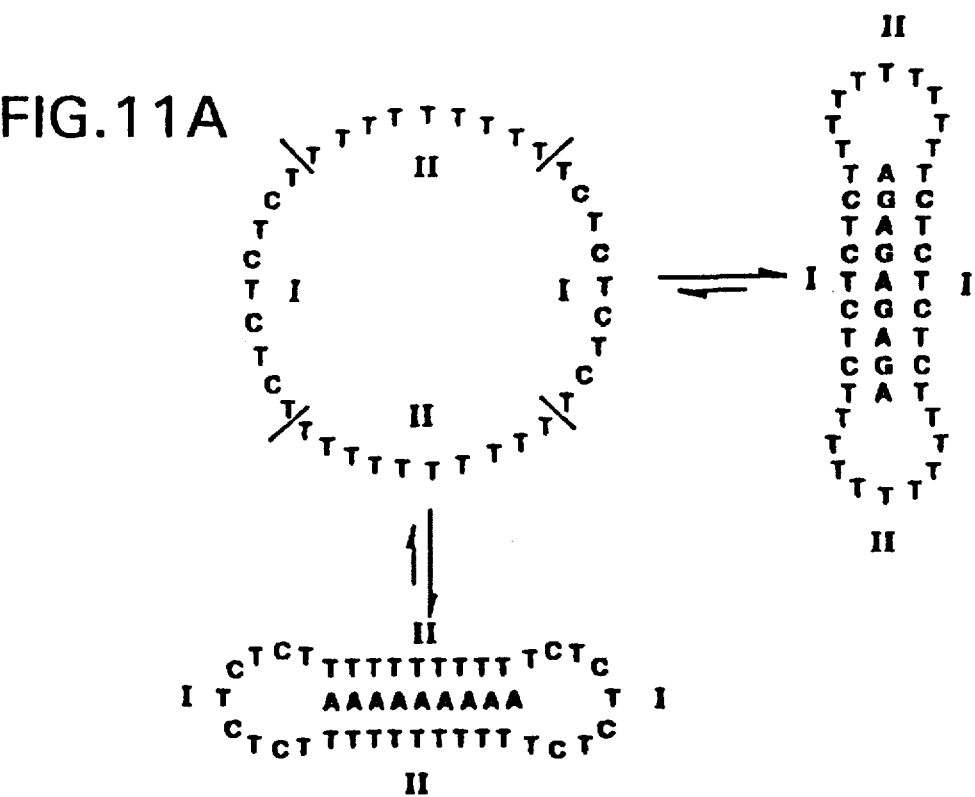
FIG. 11A is a schematic diagram illustrating the binding of a SEQ ID NO:18 circular oligonucleotide having two pairs of binding domains, i.e. I and II, with either of target oligonucleotide SEQ ID NO:19 or target oligonucleotide SEQ ID NO:20. This figure illustrates that when binding domain pair I has bound its target oligonucleotide, the P and AP domains of pair II serve as loop domains separating the P and AP binding domains of pair I, and vice versa.
Figure 11B:
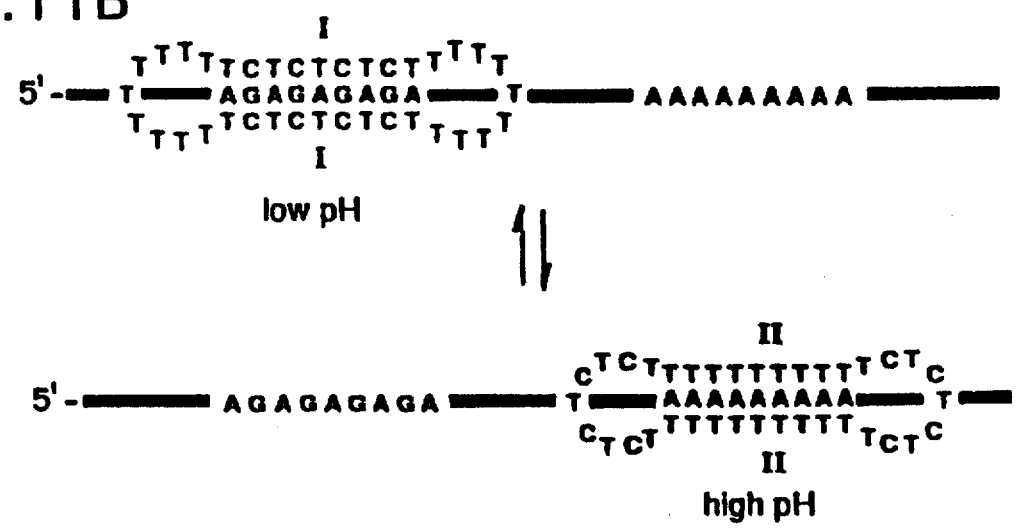
FIG. 11b is a schematic diagram illustrating the effect of pH upon target selection by the SEQ ID NO:18 circular oligonucleotide which has two pairs of binding domains, i.e. I and II. In this case two target sites, complementary to the pair I and pair II binding domains, are present within a single oligonucleotide. When the pH is low, pair I binding domains which contain cytosine preferentially bind to their complementary target, while the pair II binding domains which contain no cytosine do not bind their target. However, when the pH is high, pair II binding domains containing no cytosine preferentially bind to their target while the pair I binding domains remain unbound.

Accordingly, when binding domain pair I bound its target oligonucleotide, the P and AP domains of pair II served as loop domains between the parallel and anti-parallel binding domains of pair I. Similarly, when binding domain pair II bound its target, the P and AP domains of pair I served as loop domains separating the parallel and anti-parallel binding domains of pair II. These two binding arrangements are depicted in FIG. 11A.

Figure 13A:
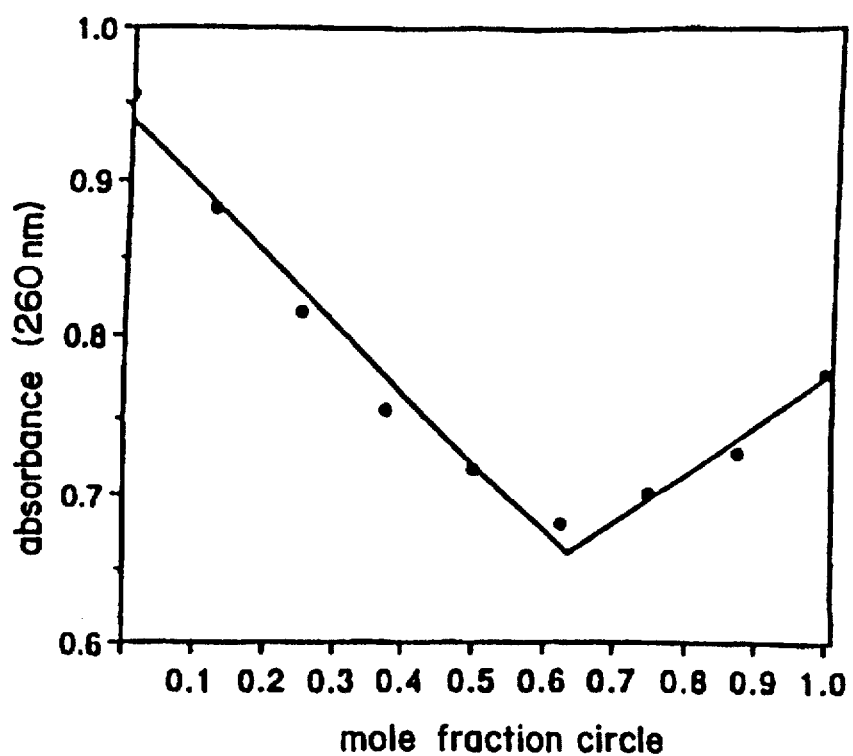
FIG. 13A depicts the absorbance versus mole fraction of SEQ ID NO:18 circular oligonucleotide present in a mixture with the longer two-target site oligonucleotide having SEQ ID NO:21. The mole fraction of circular oligonucleotide at complete complexation (inflection point in the observed absorbance) is about 0.63.

FIG. 13A depicts the absorbance versus mole fraction of SEQ ID NO:18 circular oligonucleotide present in a mixture with the longer two-target site oligonucleotide having SEQ ID NO:21. The mole fraction of circular oligonucleotide at complete complexation is about 0.63. This roughly corresponds to a stoichiometry of two circular oligonucleotides per target. Therefore separate circular oligonucleotides can bind to each of the two target binding sites present in the SEQ ID NO:21 oligonucleotide.

The complexes formed between circular oligonucleotide with SEQ ID NO:18 and targets having SEQ ID NO:19 or SEQ ID NO:20 were considerably stronger than corresponding complexes formed between a linear single binding domain oligonucleotide and target. For example, a nine base duplex formed between $d(A)_9$ (i.e. SEQ ID NO:20) and $d(T)_9$ (i.e. SEQ ID NO:23) had a $T_m$ of 25° C. and a duplex formed between $d(AG)_4A$ (i.e. SEQ ID NO:19) and $d(TC)_4T$ (i.e. SEQ ID NO:22) had a $T_m$ of 29° C. Therefore, the SEQ ID NO:18 circular oligonucleotide formed complexes with $T_m$ values that were at least 15° C. higher than corresponding linear duplex complexes. These results are summarized in Table 7 below. Given the high $T_m$ values and the 1:1 stoichiometry of the SEQ ID NO:18 oligonucleotide-target complexes, the complexes formed were triple-helical, and not double-helical.

TABLE 7

$T_m$ VALUES OF LINEAR OLIGONUCLEOTIDES
BOUND TO DIFFERENT TARGETS AT NEUTRAL pH

| LINEAR OLIGONUCLEOTIDE | TARGET OLIGONUCLEOTIDE | $T_m$ |
| --- | --- | --- |
| $d(TC)_4T$ (SEQ ID NO:22) | $d(AG)_4A$ (SEQ ID NO:19) | 29° C. |
| $d(T)_9$ (SEQ ID NO:23) | $d(A)_9$ (SEQ ID NO:20) | 25° C. |

$T_m$ VALUES OF THE SEQ ID NO:18
CIRCULAR OLIGONUCLEOTIDE
BOUND TO DIFFERENT TARGETS AT NEUTRAL pH

Figure 12:
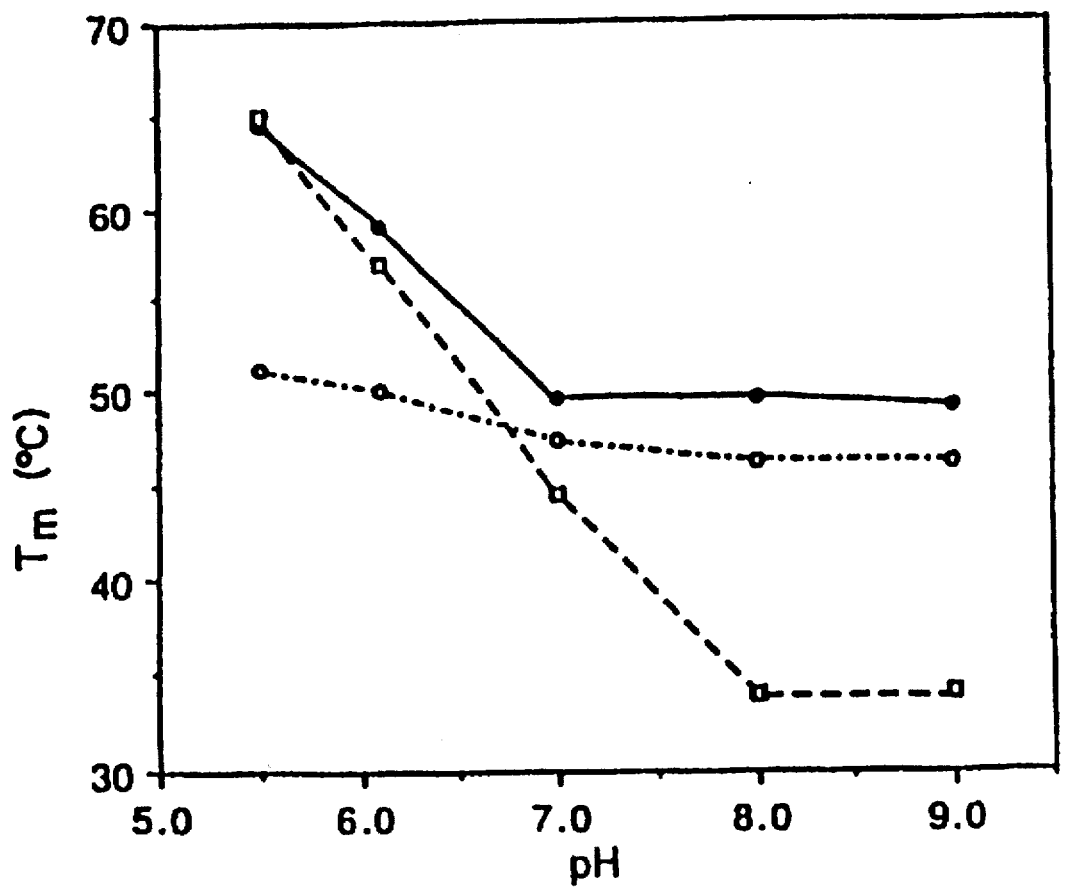
FIG. 12 depicts the melting temperature $(T_m)$ as a function of pH when the two binding domain SEQ ID NO:18 circular oligonucleotide is bound to target oligonucleotide SEQ ID NO:20 (open circles), SEQ ID NO:19 (open squares) or SEQ ID NO:21 (filled circles). Oligonucleotides having SEQ ID NO:19 or SEQ ID NO:20 have a single target for the SEQ ID NO:18 circular oligonucleotide, however the oligonucleotide having SEQ ID NO:21 encoded two separate target sites for the SEQ ID NO:18 circular oligonucleotide.

| CIRCULAR OLIGONUCLEOTIDE | TARGET OLIGONUCLEOTIDE | $T_m$ |
| --- | --- | --- |
| SEQ ID NO:18 | SEQ ID NO:19 | 44.5° C. |
| SEQ ID NO:18 | SEQ ID NO:20 | 47.5° C. | pH Dependence of SEQ ID NO:18 Circular Oligonucleotide Binding to SEQ ID NO:19 and SEQ ID NO:20 Target Oligonucleotides The observed $T_m$ for the SEQ ID NO:20 target bound to the SEQ ID NO:18 circular oligonucleotide did not vary greatly from pH 5.5 to 9.0 (FIG. 12, open circles). In particular the $T_m$ of this complex at pH 5.5 was 51.5° C. and at pH 9.0 the $T_m$ was 46° C. These data are consistent with triple-helical complexes having only T—A—T triads, which require no protonation changes to optimize binding (Morgan et al. 1968 J. Mol. Biol. 37:63–80; Moser et al. 1987 Science 238:645; and Rajagopal et al. 1989 Nature 339:637).

In contrast, the observed $T_m$ for the SEQ ID NO:19 target bound to the SEQ ID NO:18 circular oligonucleotide varied significantly over a range of 30° C. when the pH was varied from 5.5 to 9.0 (FIG. 12, open squares). In particular, at pH 5.5 the $T_m$ of the SEQ ID NO:19 target-SEQ ID NO:18 circular oligonucleotide complex was 65° C. However at pH 9.0 the same complex had a $T_m$ of 35° C. These observations are consistent with previous observations that efficient formation of a C—G—C triad requires protonation of the cytosine in the parallel binding domain (Lipsett et al. 1963 Biochem. Biophys. Res. Comm. 11:224–228 and Morgan et al. 1968).

Figure 13B:
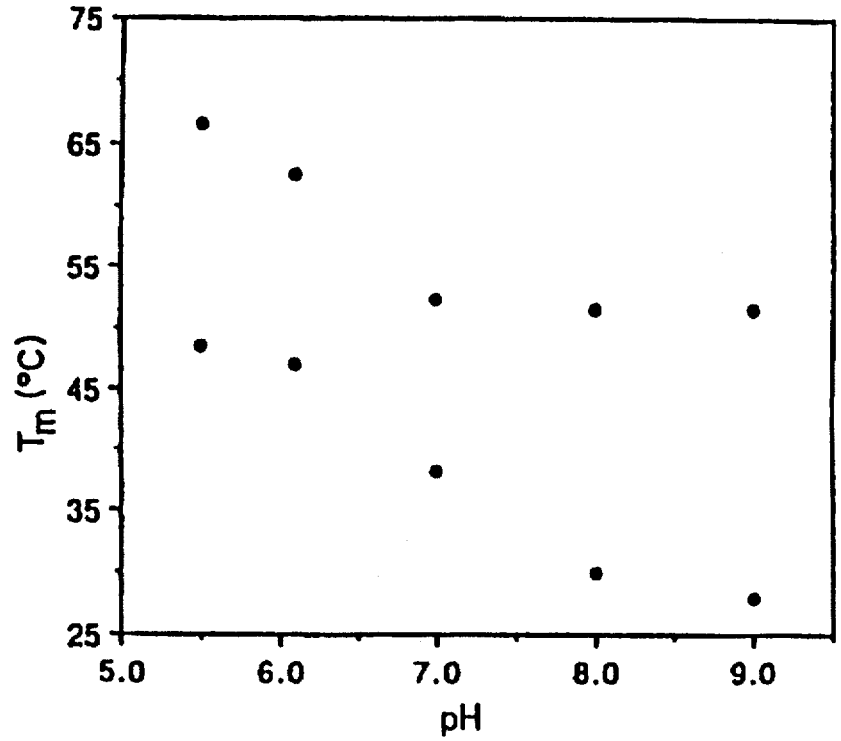
FIG. 13B depicts the observed $T_m$ values for the SEQ ID NO:18 circular oligonucleotide bound to the two target-site oligonucleotide having SEQ ID NO:21. As shown, there are two $T_m$ values at each of the pH values tested. These two $T_m$ values correspond to separate melting events at each of the two target sites within the SEQ ID NO:21 oligonucleotide.

Therefore, at pH 5.5 the complex having C—G—C triads (i.e. target SEQ ID NO:19 bound to SEQ ID NO:18 circular oligonucleotide) had a $T_m$ which was about 14° C. higher than the complex having only T—A—T triads (i.e target SEQ ID NO:19 bound to SEQ ID NO:18 circular oligonucleotide). However at pH 9.0 the $T_m$ of the C—G—C triad containing complex was about 13° C. lower than the T—A—T triad containing complex. The pH of $T_m$ equivalency for the C—G—C and T—A—T containing complexes was pH 6.8.

pH Dependence of SEQ ID NO:18 Circular Oligonucleotide Binding to the Two-Target Site SEQ ID NO:21 Oligonucleotide The effect of pH upon binding of the SEQ ID NO:18 circular oligonucleotide with the longer two-target site oligonucleotide having SEQ ID NO:21 was also observed. FIG. 13B depicts the observed $T_m$ values for two molar equivalents SEQ ID NO:18 circular oligonucleotide bound to the SEQ ID NO:21 target. As shown, there were two $T_m$ values at each of the pH values tested. These two $T_m$ values correspond to separate melting events at each of the two target sites within the SEQ ID NO:21 oligonucleotide. Moreover the pattern of observed $T_m$ values for the SEQ ID NO:21 oligonucleotide parallels the pattern of $T_m$ values observed separately for the SEQ ID NO:19 and SEQ ID NO:20 target oligonucleotides. Therefore, each of the two $T_m$ values observed at a single pH for the SEQ ID NO:21 oligonucleotide can be assigned to a specific target site within this oligonucleotide. For example, at pH 5.5, $T_m$ values of 47° C. and 67° C. were observed for the SEQ ID NO:21 oligonucleotide. The $T_m$ values for the SEQ ID NO:19 and SEQ ID NO:20 targets were 65° C. and 51.5° C., respectively. Therefore the 47° C. $T_m$ value observed at pH 5.5 for the SEQ ID NO:21 oligonucleotide corresponds to the target encoding the same sequence as SEQ ID NO:20, i.e. (5'-dAAAAAAAAA). Similarly the 67° C. $T_m$ value observed at pH 5.5 for the SEQ ID NO:21 oligonucleotide corresponds to the target encoding the same sequence as SEQ ID NO:19, i.e. (5'-dAGAGAGAGA).

Therefore, the melting of each target within the SEQ ID NO:21 oligonucleotide can be separately observed and monitored at pH values ranging from 5.5 to 9.0.

Figure 14A:
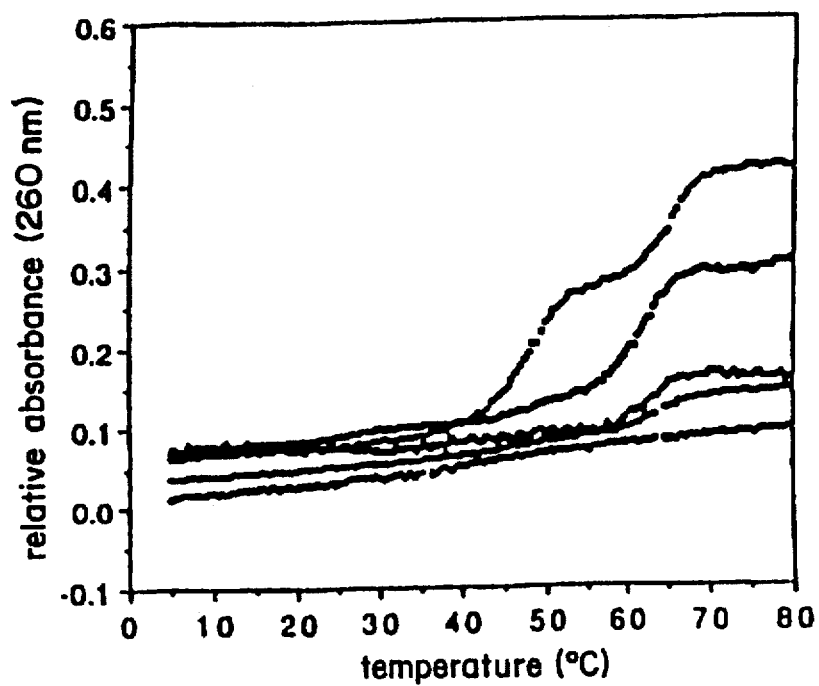
FIG. 14A depicts the relative absorbance at 260 nm of increasing amounts of the SEQ ID NO:18 circular oligonucleotide bound to the two-target site SEQ ID NO:21 oligonucleotide at pH 5.5. The SEQ ID NO:21 oligonucleotide was present at 1.5 µM and the SEQ ID NO:18 circular oligonucleotide concentration was present at 0, 0.25, 0.5, 1.0 and 2.0 molar equivalents (lower to upper curves, respectively). The temperature at which the absorbance increases dramatically corresponds to the melting temperature. Only one sharp increase in absorbance was observed at about 60° C. when the circular oligonucleotide was present at 0, 0.25, 0.5 and 1.0 molar equivalents (lower four curves). However, two sharp increases in absorbance were observed at about 47° C. and about 60° C. when 2.0 molar equivalents of circular oligonucleotide were mixed with 1.0 molar equivalents of the SEQ ID NO:21 oligonucleotide.
Figure 14B:
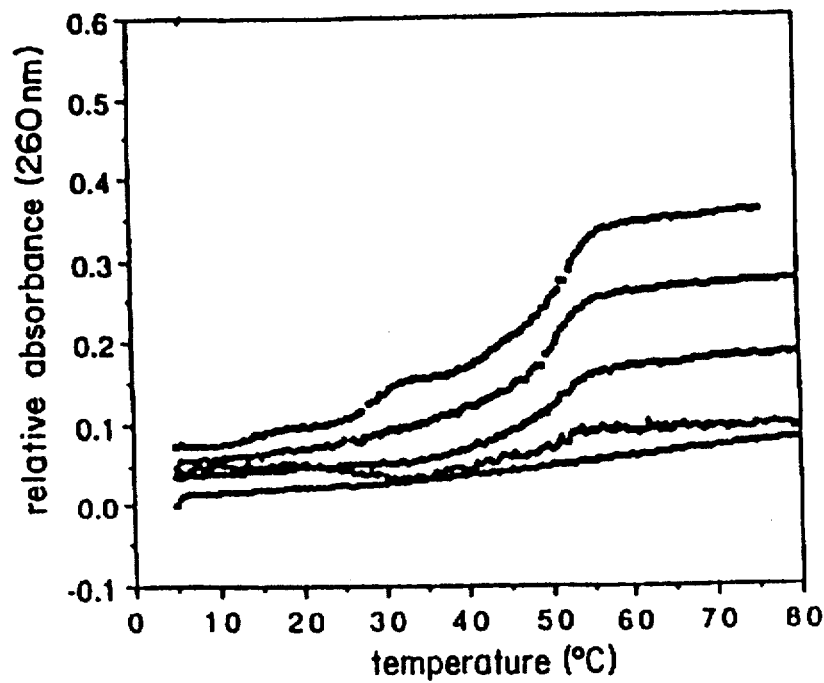
FIG. 14B depicts the relative absorbance at 260 nm of increasing amounts of the SEQ ID NO:18 circular oligonucleotide bound to the two-target site SEQ ID NO:21 oligonucleotide at pH 8.5. The SEQ ID NO:21 oligonucleotide was present at 1.5 µM and the SEQ ID NO:18 circular oligonucleotide was present at 0, 0.25, 0.5, 1.0 and 2.0 molar equivalents (lower to upper curves, respectively). The observed melting points at low molar ratios of circular oligonucleotide to SEQ ID NO:21 oligonucleotide is about 52° C.

Modulation of pH Can Selectively Direct Circular Oligonucleotide Binding to One Target vs Another The melting of varying amounts of the SEQ ID NO:18 circular oligonucleotide from the two-target site SEQ ID NO:21 oligonucleotide was monitored by observing the absorbance at 260 nm as the temperature was increased (FIG. 14). A sharp increase in the absorbance at this wavelength indicates that melting has occurred and provides a $T_m$ value for the SEQ ID NO:18–SEQ ID NO:21 complex at a given pH. These data also indicate which target site within the SEQ ID NO:21 oligonucleotide is occupied first by the circular oligonucleotide.

For example, FIG. 14A depicts the absorbance changes occurring as temperature is increased at pH 5.5 when the SEQ ID NO:21 oligonucleotide was present at 1.5 µM and the SEQ ID NO:18 circular oligonucleotide concentration was present at 0, 0.25, 0.5, 1.0 and 2.0 molar equivalents (lower to upper curves, respectively).

At low molar ratios of circular oligonucleotide (0.25, 0.50 and 1.0) a single sharp increase in absorbance was observed when the temperature was about 63° C. to 64° C. (FIG. 14A, middle three curves). This $T_m$ of about 63° C. to 64° C. indicates that melting is occurring from the SEQ ID NO:21 target site having the sequence AGAGAGAGA. Therefore at pH 5.5 when the proton concentration is relatively high, the target site having guanine residues is occupied first since formation of C—G—G triads is favored over formation of T—A—T triads.

However, when the circular oligonucleotide is present at 2.0 molar equivalents relative to the SEQ ID NO:21 oligonucleotide, two sharp increases in absorbance are apparent at pH 5.5 (FIG. 14A highest curve). Therefore when a molar excess of the circular oligonucleotide is present both target sites in the SEQ ID NO:21 oligonucleotide can be occupied by separate circular oligonucleotides.

At a higher pH of 8.5, when fewer protons are available, the observed $T_m$ at low molar ratios of circular oligonucleotide to SEQ ID NO:21 oligonucleotide, is significantly lower than observed at pH 5.5, i.e. about 52° C. (FIG. 13B middle three curves, corresponding to molar ratios of SEQ ID NO:18 to SEQ ID NO:21 oligonucleotide of 0.25, 0.5 and 1.0). A $T_m$ of about 52° C. indicates that melting is occurring from the target site encoding AAAAAAAA. Therefore at pH 8.5 the target site having only adenine residues is occupied first since the low concentration of protons makes formation of C—G—C triads less favorable than formation of T—A—T triads.

Figure 15:
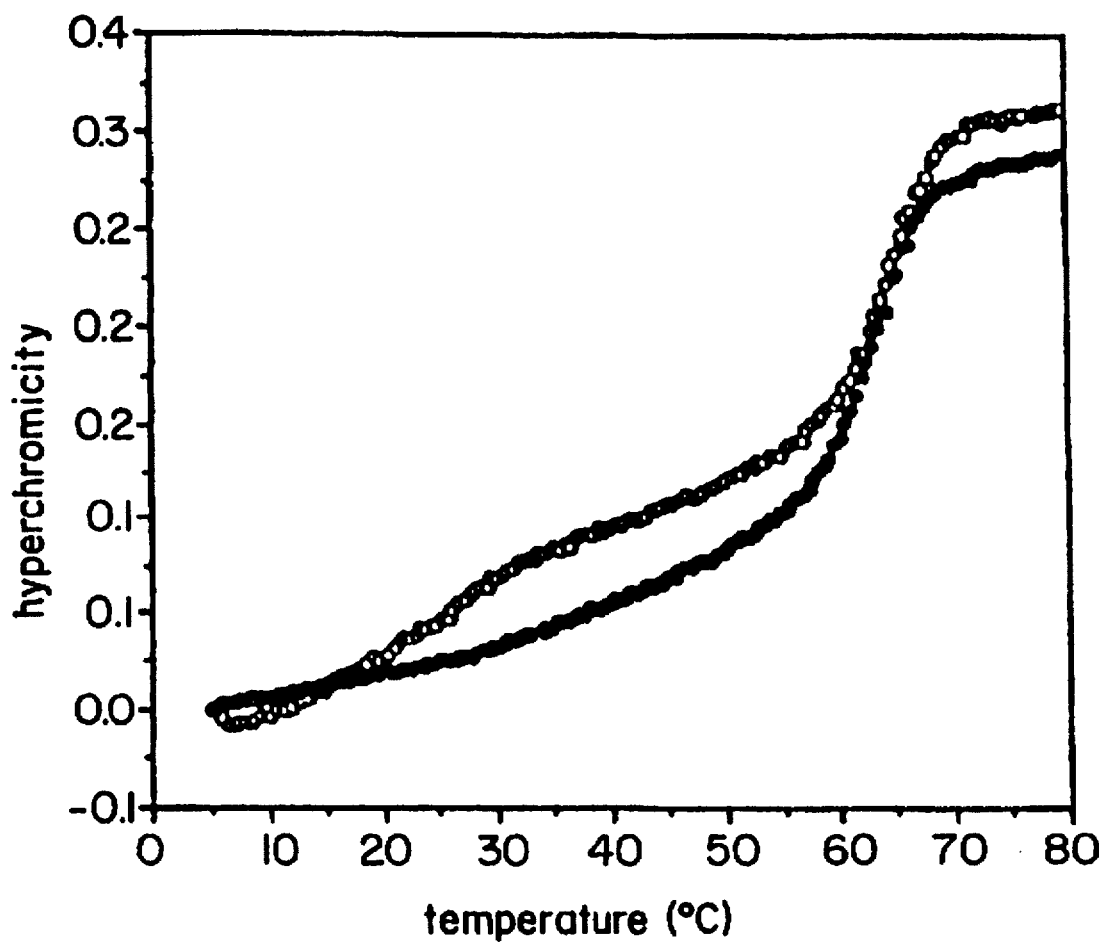
FIG. 15 depicts the hyperchromicity at pH 5.5 of a mixture of circular oligonucleotide (SEQ ID NO:18 at 1.5 µM) with two-target site oligonucleotide (SEQ ID NO:21 at 1.5 µM) in the presence of oligonucleotides having either SEQ ID NO:22 (TCTCTCTCT at 1.5 µM, filled circles) or SEQ ID NO:23 (TTTTTTTTT at 1.5 µM, open circles). Two inflections in hyperchromicity (open circles) indicate that binding has occurred at both target sites within the SEQ ID NO:21 oligonucleotide, whereas a single inflection (filled circles) indicates binding has occurred at only one site in the SEQ ID NO:21 oligonucleotide.

Addition of linear oligonucleotides having SEQ ID NO:22 (5'-dTCTCTCTCT) or SEQ ID NO:23 (5'-dTTTTTTTTT) confirmed that one target within the SEQ ID NO:21 oligonucleotide was unbound and the other target was bound by the SEQ ID NO:18 circular oligonucleotide at low pH. FIG. 14 depicts the hyperchromicity at pH 5.5 of a mixture of circular oligonucleotide (SEQ ID NO:18 at 1.5 µM) with two-target site oligonucleotide (SEQ ID NO:21 at 1.5 µM) in the presence of oligonucleotides having either SEQ ID NO:22 (TCTCTCTCT at 1.5 µM, filled circles) or SEQ ID NO:23 (TTTTTTTTT at 1.5 µM, open circles). At this low pH only the mixture of oligonucleotides having SEQ ID NO:18, 21 and 23 (open circles) had two melting temperatures, indicating that the SEQ ID NO:18 circular oligonucleotide bound to the AGAGAGAGA target site within the SEQ ID NO:21 oligonucleotide leaving the AAAAAAAA target site free for binding with the SEQ ID NO:23 oligonucleotide. Addition of the SEQ ID NO:22 oligonucleotide at pH 5.5 did not cause two melting events since this oligonucleotide was complementary to the target preferred by the circular oligonucleotide at low pH, i.e. the AGAGAGAGA target wherein C+G—C triads form. Accordingly, only one target site within the SEQ ID NO:21 oligonucleotide was occupied and only a single inflection in the hyperchromicity was observed (FIG. 15 filled circles).

Therefore, a circular oligonucleotide having two pairs of binding domains can be directed to bind one target as opposed to another by adjusting the pH of the hybridization reaction when one pair of binding domains contains more cytosine residues than the other pair.

EXAMPLE 9

Circular Oligonucleotides containing 2'-O-Methyl Nucleotides Can Bind Single-Stranded Nucleic Acid Targets The data presented in this example show that circular oligonucleotides containing 2'-O-Me nucleotides can form stable triple helical complexes with linear purine rich DNA and RNA targets.

Linear DNA (dAAGAAAGAAAAG, SEQ ID NO:13) and RNA (rAAGAAAGAAAAG, SEQ ID NO:12) targets were synthesized as described in Example 6. A circular 2'-O-methyl RNA oligonucleotide was synthesized from the precursor 5'-pr UUUCUUdCACACrUUCUUUCUUUUCdCACACr CUUUUC (SEQ ID NO:27) by the method of Example 1 to yield the circular oligonucleotide:

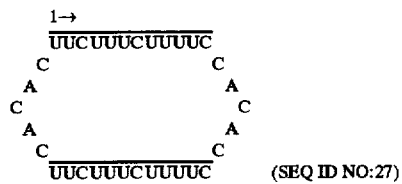

(SEQ ID NO:27)

wherein 2'-O-Me residues are designated by a line over the sequence and loop regions are composed of alternating C and A deoxynucleotides.

Also synthesized was the linear 12 nucleotide pyrimidine oligomers 2'-O-Me-RNA (rCUUUUCUUUCUU, SEQ ID NO:30) for comparison to the circles. SEQ ID NO:30 was assessed for binding to DNA (dGAAAAGAAAGAA, SEQ ID NO:28) and RNA (rGAAAAGAAAGAA, SEQ ID NO:29). A circular RNA complementary to SEQ ID NO:28 but without the 2'-O-Me modification (Table 8) was also synthesized (SEQ ID NO:27). The loop regions contain 5 deoxynucleotides and the underlined residue lacks a 2'-OH.

Melting temperatures and free energies of association for complexation of 2'-O-Me RNA circular oligonucleotide and linear target were measured at pH 7.0 and pH 5.5 as described in Example 6. These values were compared with those of the unmodified RNA circle to linear DNA and RNA targets, as well as to a Watson-Crick complex of a linear DNA or RNA target and the 2'-O-Me RNA complement. Melting temperatures and free energy values are shown in Table 8.

TABLE 8

| Complex | Type | pH = 7.0 | | pH = 5.5 | |
|---|---|---|---|---|---|
| | | $T_m(°C.)$ | $-\Delta G°_{37}(kcal)$ | $T_m(°C.)$ | $-\Delta G°_{37}(kcal)$ |
| UUCUUUCUUUC<br>C               C<br>A               A<br>C  dAAGAAAGAAAAG  C<br>A               A<br>C               C<br>UUCUUUCUUUC | M<br><br><br>D<br><br><br>M | 58.6 | 13.6 | 70.0 | 15.6 |
| UUCUUUCUUUC<br>C               C<br>A               A<br>C  rAAGAAAGAAAAG  C<br>A               A<br>C               C<br>UUCUUUCUUUC | M<br><br><br>R<br><br><br>M | 57.8 | 14.2 | 57.8 | 13.9 |
| UUCUUUCUUUC<br>C               C<br>A               A<br>C  rAAGAAAGAAAAG  C<br>A               A<br>C               C<br>UUCUUUCUUUC | R<br><br><br>D<br><br><br>R | 51.1 | 12.8 | 63.2 | 15.9 |
| UUCUUUCUUUC<br>C               C<br>A               A<br>C  dAAGAAAGAAAAG  C<br>A               A<br>C               C<br>UUCUUUCUUUC | R<br><br><br>R<br><br><br>R | 54.0 | 14.3 | 63.9 | 16.7 |
| 3'-dGAAAAGAAAGAA<br>5'-rCUUUUCUUUCUU | DM | 21.9 | 6.0 | 24.8 | 6.1 |
| 3'-rGAAAAGAAAGAA<br>5'-rCUUUUCUUUCUU | RM | 54.9 | 12.8 | 55.6 | 12.9 |

*Conditions: 100 mM NaCl, 10 mM MgCl₂, 10 mM Na · PIPES buffer, 3 μM total DNA concentration.
ᵇUncertainties in $T_m$ values and in free energies are estimated at ±15%, respectively.

Comparison of 2'-O-Me RNA circular and linear oligonucleotides indicates that for binding to a DNA target, there is clear benefit from the Hoogsteen interaction. (Compare, for example, $T_m$ at pH 7.0 for MDM of 58.6° vs. 21.9° C. for DM). Further, the MDM complex exhibits pH dependency. These results indicate that the MDM complex is triple helical.

In contrast, the MRM complex is not pH dependent and exhibits only a slight advantage in binding relative to the RM duplex, suggesting that the MRM complex may be a duplex, with the third strand dissociated and not binding in the major groove.

Comparison of RNA circles to 2'-O-Me RNA circles illustrates a slight binding advantage for 2'-O-Me RNA circles in some cases, particularly to DNA targets. Since 2'-O-Me-RNA offers the significant advantage of resistance to degradation by endonuclease enzymes (Sproat et al., 1989, Nucleic Acids Eds. 17:3373), this analog is attractive for use in circles even in cases in which some binding affinity is sacrificed.

The data in Table 8 further demonstrate that unmodified RNA circles containing DNA loops exhibit high affinity, pH dependent binding to both RNA and DNA targets. Binding of such circles to single-stranded targets is thus consistent with triplex formation.

EXAMPLE 10

Circular Oligonucleotide Probes Containing DNA and RNA Binding Domains Bind DNA Targets Data presented in this example demonstrate that oligonucleotide circles containing both an RNA binding domain and a DNA binding domain can effectively bind linear DNA and RNA targets. A circular chimeric oligonucleotide probe containing a DNA binding domain and an RNA binding domain linked by deoxynucleotides was synthesized as described in Example 1 and is illustrated below. The RNA binding domain is the upper domain while the DNA binding domain is the lower domain.

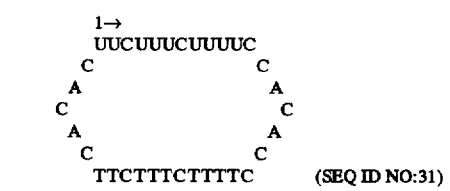

The linear targets 5'-dAAGAAAGAAAAG-3' (SEQ ID NO:13) and 5'-rAAGAAAGAAAAG-3' (SEQ ID NO:12) were synthesized and the binding affinity of the chimeric probe examined at pH 7.0 and 5.5 as described in Example 6. Melting temperatures and binding energies are presented in Table 9.

TABLE 9

| Complex | Type | pH = 7.0 | | pH = 5.5 | |
|---|---|---|---|---|---|
| | | $T_m(°C.)$ | $-\Delta G°_{37}(kcal)$ | $T_m(°C.)$ | $-\Delta G°_{37}(kcal)$ |
| UUCUUUCUUUUC / dAAGAAAGAAAAG / TTCTTTCTTTTC | R / D / D | 54.2 | 14.6 | 66.2 | 23.6 |
| UUCUUUCUUUUC / rAAGAAAGAAAAG / TTCTTTCTTTTC | R / R / D | 48.3 | 13.0 | 59.8 | 16.3 |

<sup>a</sup>Conditions: 100 nM NaCl, 10 mM MgCl₂, 10 mM Na · PIPES buffer, 3 µM total DNA concentration.
<sup>b</sup>Error in $T_m$ values and in free energies are estimated at ±1.0° C. and ±15%, respectively.

Examination of the data obtained at pH 7.0 reveals that the chimeric probes form high affinity complexes with the linear DNA and RNA targets.

At pH 5.5 the $T_m$ and binding energy dramatically increase suggesting in that circular chimeric oligonucleotides bind linear DNA and RNA targets with high affinity by triplex formation.

EXAMPLE 11

Circular Oligonucleotides Inhibit Proliferation of Chronic Myeloid Leukemia Cells in a Sequence Specific Manner Chronic myeloid leukemia is a human malignant disease characterized by a reciprocal translocation between the long arms of chromosomes 9 and 22. The resulting hybrid gene on chromosome 22 is designated bcr-abl and consists of a 5'bcr portion and a 3'abl portion. Transcripts of the fusion gene are primarily of two types, designated bcr exon 3/abl exon 2 and bcr exon 2/abl exon 2. These fusion genes are ideal targets for antisense attack since they are unique to malignant cells.

Human cell lines that contain bcr—abl fusions are available as model systems for chronic myeloid leukemia. K562 cells contain the bcr 3/abl 2 fusion gene (Lozzio et al., 1975, Blood 45:321) and BV173 cells contain the bcr 2/abl2 fusion gene. (Pegoraro et al., 1983, Jour. Nat. Cancer Inst. 70:447).

A polypurine sequence located 385 nucleotides 5' to the bcr 3/abl 2 junction was chosen as a target for K562 cells. The −385 bcr target has the sequence:

5'AGAGAGAAGAGG-3' (SEQ ID NO:32).

An antisense −385 bcr circle having binding domains parallel and antiparallel to the target sequence was synthesized by the method of Example 1. The −385 bcr circle has the sequence:

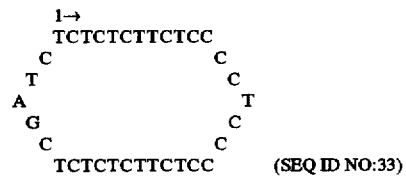

(SEQ ID NO:33)

A linear control containing the Watson-Crick complement of the target sequence, and a circular control containing a scrambled sequence of the same oligonucleotide composition as the −385bcr circle, were synthesized as controls.

For BV173 cells, the bcr 2/abl2 junction itself is a polypurine sequence and was chosen as the target, the b2a2 target has the sequence:

5'-ATAAGGAAGAAG-3' (SEQ ID NO: 34)

The antisense -b2a2 circle having binding domains parallel and antiparallel to the target sequence was synthesized. The antisense b2a2 circle has the sequence:

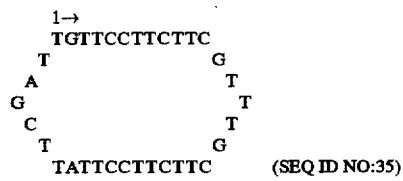

(SEQ ID NO:35)

A nonsense circle having the same nucleotide composition as the b2a2 circle but in random sequence was synthesized as a control. Also synthesized were two linear controls, a "long" linear antisense corresponding to the entire antisense circle sequence but with unligated ends, and a "short" linear antisense corresponding only to the Watson-Crick binding domain.

K562 cells were preincubated in RPM1-1640 with −385 bcr circle oligonucleotide or linear or circular control oligonucleotide at final concentrations of from zero to 13 µm. After four hours, heat-treated (65° C., 30 min.) fetal bovine serum was added to a final concentration of 10% and oligonucleotide was again added to the same final concentration. Viable cell as determined by trypan blue exclusion were counted daily and cell concentrations determined by hemocytometer.

Figure 16:
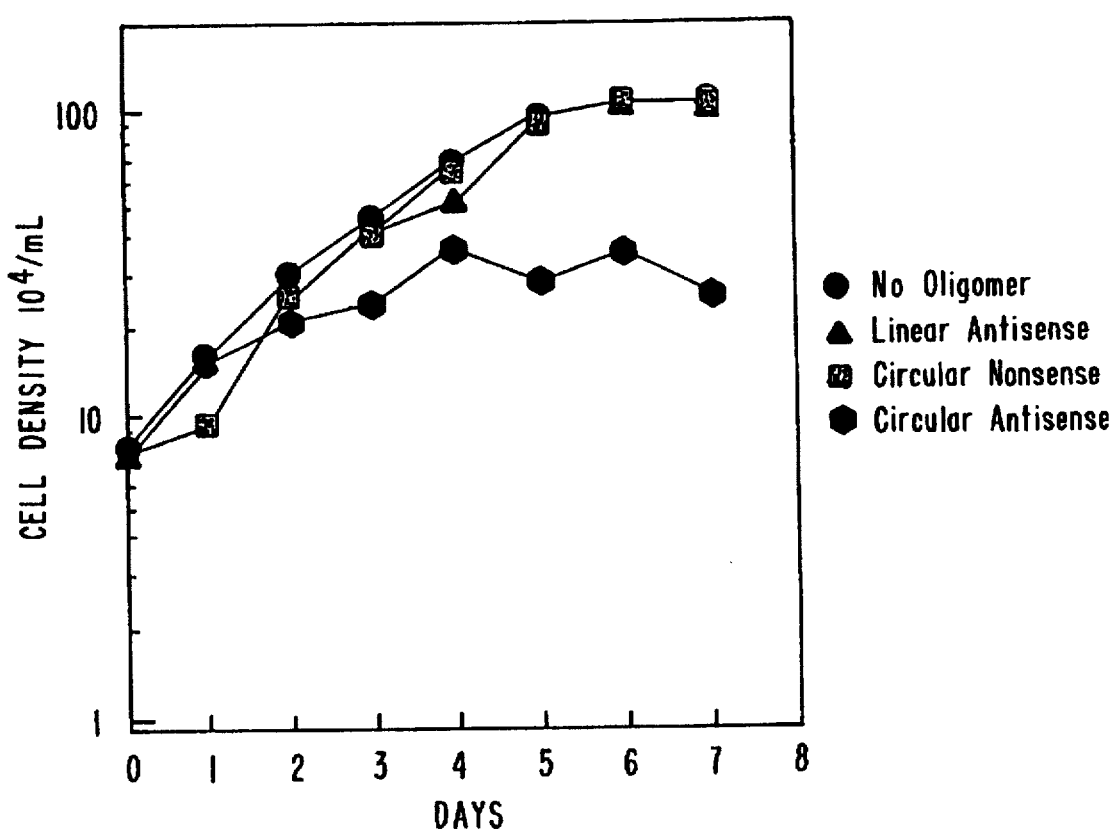
FIG. 16 depicts the effect of circular (SEQ ID NO:35) and control oligonucleotides at 13 µM on proliferation of K562 cells.
Figure 17:
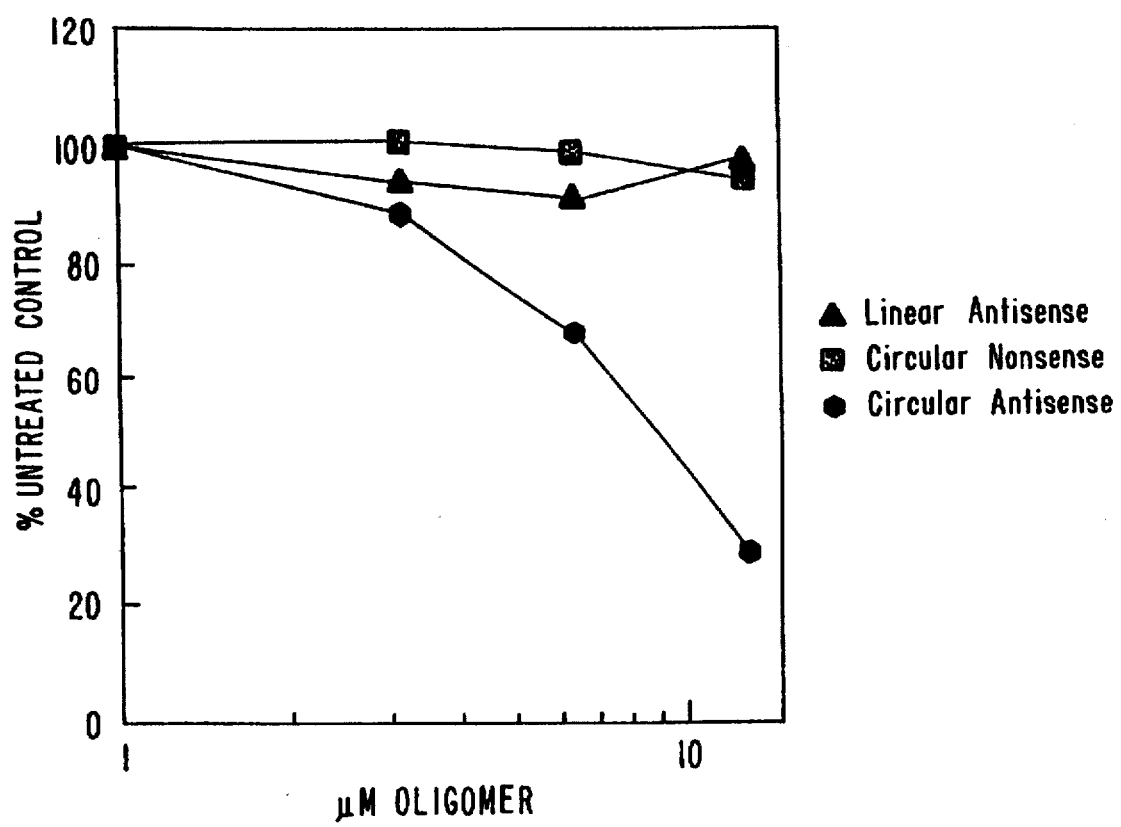
FIG. 17 shows the effect of circular (SEQ ID NO:35) and control oligonucleotides at varying concentrations on the proliferation of K562 cells at Day 5.

Results of the antisense inhibition of K562 cells are shown in FIGS. 16 and 17. FIG. 16 illustrates the effect of the −385 bcr circle (circular antisense) and the linear and circular controls at 13 µM concentrations. At 13 µM, the −385 bcr circle reduced the saturating cell number by 68%, whereas a nonsense circular and a linear control had no effect on cell growth.

The effect of the −385 bcr circle and the controls on cell growth at various concentrations on day 5 is shown in FIG. 17. The −385 bcr circle had an antiproliferative effect even at 6 µM, while both controls were ineffective in inhibiting cell growth.

BV173 cells were preincubated in RPMI-1640 with the b2a2 antisense circle, long linear control, short linear control or nonsense circular control at final concentrations of from 0 to 32 µM. After four hours, heat-treated (65° C., 30 min.) fetal bovine serum was added to a final concentration of 10% and oligonucleotide was again added to the same final concentration. Viable cell counts and cell concentrations were determined daily.

Figure 18A:
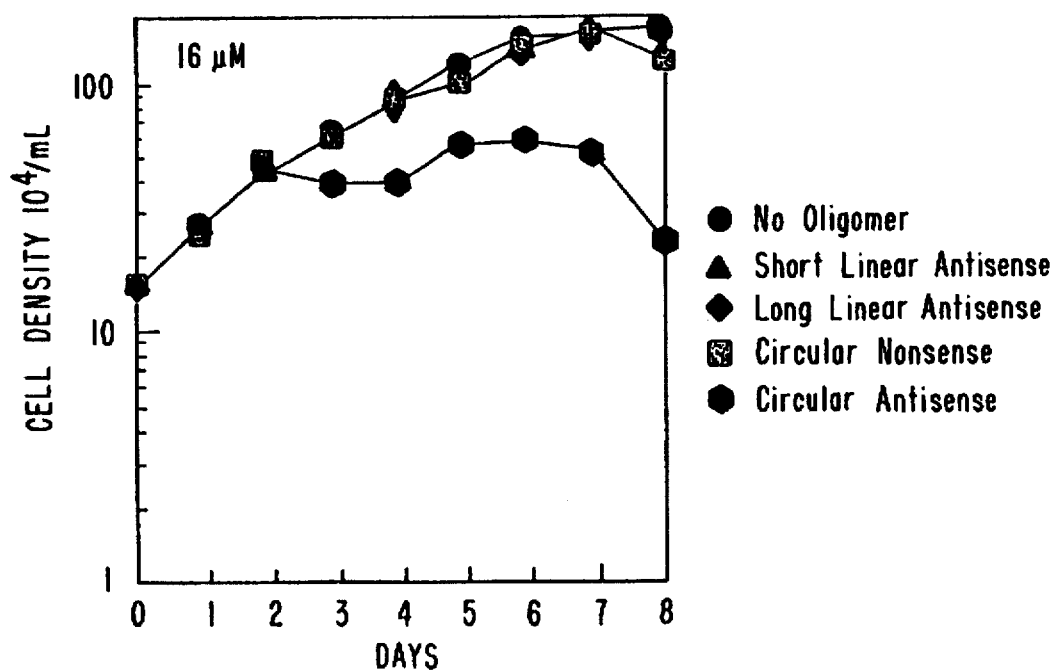
FIG. 18A and 18B illustrate the effect of circular (SEQ ID NO:37) and control oligonucleotides on the proliferation of BV173 cells at 16 µM (FIG. 18A) and 32 µM (FIG. 18B).
Figure 18B:
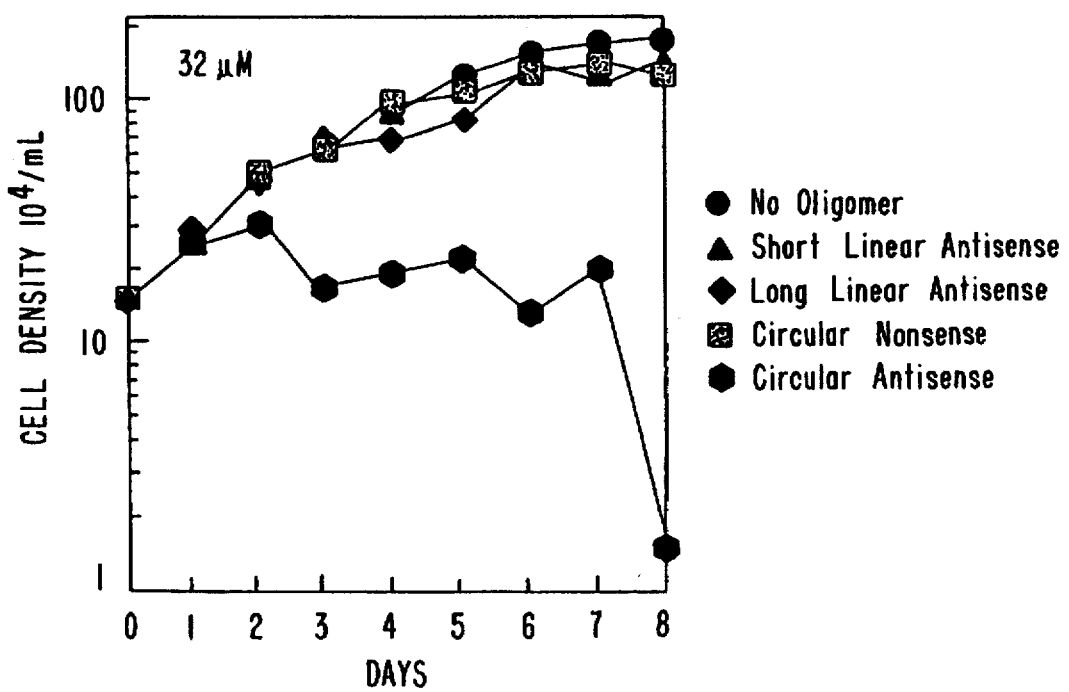
Figure 19:
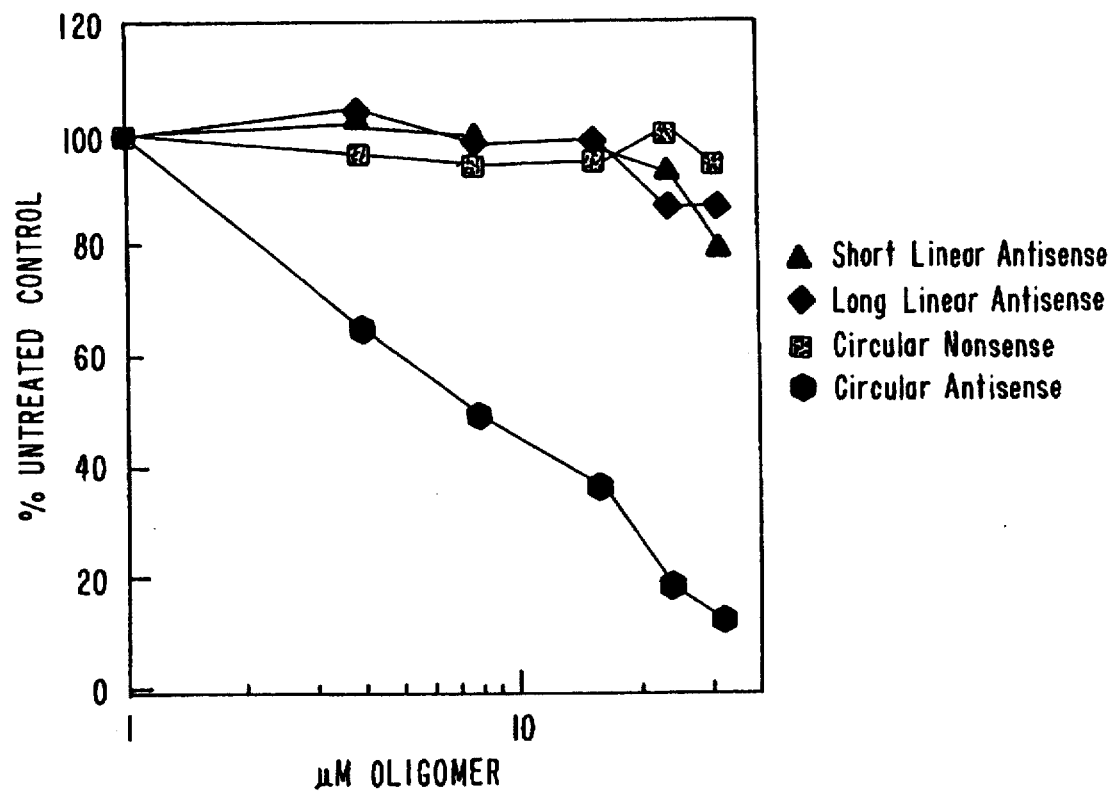
FIG. 19 depicts the effect of circular (SEQ ID NO:37) and control oligonucleotides at varying concentrations on the proliferation of BV173 cells at Day 7.

Results of the antisense inhibition of BV173 cells are shown in FIGS. 18 and 19. FIG. 18 illustrates the effect of the b2a2 circle and the various controls at 16 µM and 32 µM concentrations. At 16 µM, the cells arrested at a density 66% below that of the untreated control. At 32 µM, cells arrested at nearly 90% below the untreated control. The control sequences were ineffective in inhibiting cell growth.

The effect of the b2a2 circle and controls at various concentrations on day 7 is shown in FIG. 19. Day 7 was chosen because of the slower growth of the BV173 cell line relative to K562 cells. The b2a2 circle was effective in inhibiting cell growth at concentrations of 4 µM, while the controls were ineffective in inhibiting cell growth.

The foregoing results demonstrate that circular oligonucleotides inhibit the proliferation of chronic myeloid leukemia cells in culture in a sequence-specific manner.

EXAMPLE 12

Circular Oligonucleotides are Nuclease Resistant

Figure 20B:
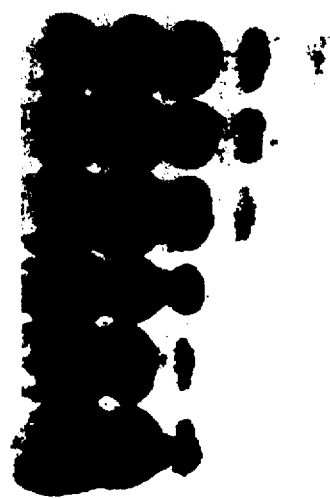
FIGS. 20A and B show sequencing gels of the products resulting from the incubation of circular and linear forms of SEQ ID NO:37 in 10% fetal bovine serum at 37° C. for 0 to 72 hours.
Figure 20A:
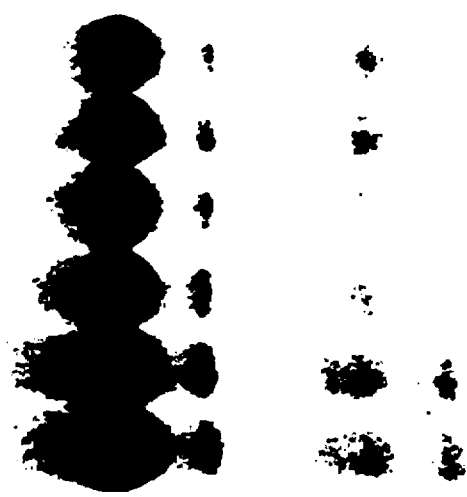

To demonstrate the enhanced stability of circular oligonucleotides, circularized and linear forms of the bcr 2/abl2 antisense deoxynucleotide of Example 11 were incubated in 10% fetal bovine serum at 37° C. for 0 to 72 hours and analyzed on a sequencing gel. As can be seen in FIG. 20, the linear oligonucleotide forms a ladder of breakdown products whereas the circular one remains intact.

---

What is claimed:

1. A single-stranded circular oligonucleotide comprising at least one parallel binding (P) domain and at least one anti-parallel binding (AP) domain and further comprising at least one first loop domain and at least one second loop domain wherein said P domain and said AP domain have sufficient complementarity to bind detectably to one strand of a defined nucleic acid target, wherein said P domain is capable of binding in a parallel manner to said target, and said AP domain is capable of binding in an anti-parallel manner to said target, and wherein a first end of said P and AP domains are separated by said first loop domain and a second end of said P and AP domains are separated by said second loop domain.

2. The oligonucleotide of claim 1 wherein a nucleotide sequence for a sufficient number of positions in said P domain and in said AP domain to achieve detectable binding is determined from the sequence of a target of known nucleotide sequence, and wherein for a sufficient number of positions in said P domain:

when a base for a position in said target is guanine or a guanine analog, then P has cytosine, or a suitable analog thereof, in a corresponding position;

when a base for a position in said target is adenine, or an adenine analog then P has thymine or uracil, or suitable analogs thereof, in a corresponding position;

when a base for a position in said target is thymine, or a thymine analog, then P has cytosine or guanine, or suitable analogs thereof, in a corresponding position;

when a base for a position in said target is cytosine, or a cytosine analog, then P has cytosine, thymine or uracil, or suitable analogs thereof, in a corresponding position; and when a base for a position in said target is uracil, or a uracil analog, then P has cytosine, guanine, thymine or uracil, or suitable analogs thereof, in a corresponding position;

and for a sufficient number of positions in said AP domain:

when a base for a position in said target is guanine, or a guanine analog, then AP has cytosine or uracil, or suitable analogs thereof, in a corresponding position;

when a base for a position in said target is adenine, or an adenine analog, then AP has thymine or uracil, or suitable analogs thereof, in a corresponding position;

when a base for a position in said target is thymine, or a thymine analog, then AP has adenine, or a suitable analog thereof, in a corresponding position;

when a base for a position in said target is cytosine, or a cytosine analog, then AP has a guanine, or a suitable analog thereof, in corresponding position; and when a base for a position in said target is uracil, or a uracil analog, then AP has adenine or guanine, or suitable analogs thereof, in a corresponding position;

wherein said sufficient number of positions is that number of positions to provide sufficient complementarity for said oligonucleotide to bind detectably to said target.

3. The oligonucleotide of claim 1 or 2 wherein said target, said P domain and said AP domain independently comprise 2 to 200 nucleotides.

4. The oligonucleotide of claim 3 wherein said target, said P domain and said AP domain independently comprise 6 to 36 nucleotides.

5. The oligonucleotide of claim 1 or 2 wherein each loop domain independently comprises 2 to 2000 nucleotides.

6. The oligonucleotide of claim 5 wherein each loop domain independently comprises 3 to 8 nucleotides.

7. The oligonucleotide of claim 1 or 2 wherein said target is single stranded or double stranded.

8. The oligonucleotide of claim 1 or 2 wherein said target is RNA or DNA.

9. The oligonucleotide of claim 1 or 2 wherein said target is a domain contained in a nucleic acid template.

10. The oligonucleotide of claim 1 or 2 wherein said P domain and said AP domain bind to said target in a staggered binding arrangement.

11. The oligonucleotide of claim 1 or 2 wherein sufficient complementarity is at least 50% complementarity.

12. The oligonucleotide of claim 1 or 2 wherein sufficient complementarity is 30% to 40% complementarity.

13. The oligonucleotide of claim 1 or 2 wherein said oligonucleotide comprises DNA, RNA or both DNA and RNA.

14. The oligonucleotide of claim 2 wherein a suitable analog of cytosine is 5-methylcytosine.

15. The oligonucleotide of claim 2 wherein a suitable analog of uracil is 5-methyluracil.

16. The oligonucleotide of claim 2 wherein a suitable analog of adenine is diaminopurine.

17. The oligonucleotide of claim 1 or 2 wherein at least one nucleotide has a 2'-O-methylribose in place of ribose or deoxyribose.

18. The oligonucleotide of claim 1 or 2 wherein said oligonucleotide further comprises a ligand for a cellular receptor, cholesterol group, an aryl group, a steroid group or a polycation.

19. The oligonucleotide of claim 1 or 2 wherein said oligonucleotide further comprises a drug or a drug analog.

20. The oligonucleotide of claim 1 or 2 wherein said loop domains comprise non-nucleotide loop domains.

21. The oligonucleotide of claim 20 wherein said non-nucleotide loop domains are polyethylene glycol.

22. The oligonucleotide of claim 21 wherein said polyethylene glycol is pentaethylene glycol, hexaethylene glycol or heptaethylene glycol.

23. The oligonucleotide of claim 1 or 2 wherein said oligonucleotide further comprises at least one methylphosphonate, phosphorothioate, phosphorodithioate, phosphotriester, siloxane, carbonate, acetamidate, thioether or phosphorus-boron linkage.

24. The oligonucleotide of claim 1 or 2 wherein said oligonucleotide further comprises a reporter molecule.

25. The oligonucleotide of claim 1 or 2 wherein said oligonucleotide comprises one P binding domain, one corresponding AP binding domain and two loop domains wherein said loop domains separate said P binding domain from said AP binding domain.

26. The oligonucleotide of claim 25 wherein said P domain is DNA and said AP domain is RNA.

27. The oligonucleotide of claim 25 wherein said P domain is RNA and said AP domain is DNA.

28. The oligonucleotide of claim 25 wherein said P and AP domains are RNA and said loop domains are DNA.

29. The oligonucleotide of claim 25 wherein said P and AP domains are DNA.

30. The oligonucleotide of claim 1 or 2 wherein said oligonucleotide comprises 2–5 pairs of corresponding P and AP binding domains.

31. The oligonucleotide of claim 1 or 2 wherein said oligonucleotide comprises a first pair of corresponding P and AP binding domains and a second pair of corresponding P and AP binding domains, wherein said second pair of corresponding P and AP binding domains each constitute at least part of a loop domain separating the P binding domain and the AP binding domain of said first pair when said first pair of binding domains are sufficiently complementary to bind to a first target nucleic acid, and wherein said first pair of corresponding P and AP binding domains each constitute at least part of a loop domain separating the P binding domain and the AP binding domain of said second pair of binding domains when said second pair of binding domains are sufficiently complementary to bind to a second target.

32. The oligonucleotide of claim 31 wherein said first pair of P and AP domains each comprise 2–20 cytosines while said second pair of P and AP binding domains each comprise no more than 1 cytosine.

33. A single-stranded circular oligonucleotide comprising at least one parallel binding (P) domain and at least one anti-parallel binding (AP) domain, wherein each P and AP domain has sufficient complementarity to bind detectably to one strand of a defined nucleic acid target and wherein said P domain binds in a parallel manner to said target, and a corresponding AP domain binds in an anti-parallel manner to said target.

34. A single-stranded circular oligonucleotide comprising a parallel binding (P) domain wherein said P domain has sufficient complementarity to bind detectably to one strand of a defined nucleic acid target in a parallel manner to said target.

35. A single-stranded circular oligonucleotide comprising at least one binding domain selected from the group consisting of a parallel binding (P) domain, and a Hoogstein anti-parallel (HAP) domain.

36. A single-stranded circular oligonucleotide comprising a Hoogsteen anti-parallel (HAP) domain wherein said HAP domain has sufficient complementarity to bind detectably to one strand of a duplex nucleic acid target in an anti-parallel manner to said target strand.

37. A complex formed between the oligonucleotide of claim 1 or 2 and a target.

38. A method of detecting a target nucleic acid which comprises:

contacting a sample to be tested for containing said target nucleic acid with a circular oligonucleotide of claim 1, 2 or 36 for a time and under conditions sufficient to form an oligonucleotide-target complex; and detecting said complex.

39. The method of claim 38 wherein said target nucleic acid comprises a single-stranded or a double-stranded nucleic acid target.

40. The method of claim 38 wherein said sample comprises a pure or impure nucleic acid sample, a tissue section, a cell smear or a chromosomal squash.

41. The method of claim 38 wherein said complex is detected by a fluorescence energy transfer assay.

42. A method for selectively binding the oligonucleotide of claim 32 to said first target which comprises contacting said oligonucleotide with said first target and said second target at a pH in the range of 4.5 to 7.5 under conditions sufficient for nucleic acid hybridization, wherein said first target is guanine-rich.

43. The method of claim 42 wherein said guanine-rich first target has 2–20 guanines and said second target has no more than one guanine.

44. The method of claim 42 wherein said pH is about 5.5.

45. A kit for detection or diagnosis of a target nucleic acid, or for isolation of a template nucleic acid comprising:

at least one first container providing a circular oligonucleotide of claim 1, 2 or 36.

46. The kit of claim 45 wherein said template is poly $(A)^+$ mRNA.

47. A pharmaceutical composition for regulating biosynthesis of a nucleic acid or protein comprising at least one of the oligonucleotides of claim 1, 2, or 36 and a pharmaceutically acceptable carrier.

48. A precircle complex for synthesizing the single-stranded circular oligonucleotide of claim 1 or 2 comprising the following serial arrangement: a first portion of an antiparallel (AP) domain, a first loop domain, a parallel (P) domain, a second loop domain, and a second portion of said AP domain; and further comprising an end-joining oligonucleotide having the same sequence as a target DNA which binds to the P domain and wherein said end-joining oligonucleotide functions to bring the 5' end of the first portion of said AP domain and the 3' end of the second portion of said AP domain in proximity sufficient for ligation.

49. A single stranded circular oligonucleotide comprising at least two different types of binding domains selected from the group consisting of a parallel binding (P) domain, a Hoogstein anti-parallel (HAP) domain and an anti-parallel binding (AP) domain and having loop domains which connect the ends of the binding domains.

50. A precircle complex for synthesizing the single-stranded circular oligonucleotide of claim 1 or 2 comprising the following serial arrangement: a first portion of a parallel (P) domain, a first loop domain, an anti-parallel (AP) domain, a second loop domain, and a second portion of said P domain; and further comprising an end-joining oligonucleotide having the same sequence as a target DNA which binds to the AP domain and wherein said end-joining oligonucleotide functions to bring the 5' end of the first portion of said P domain and the 3' end of the second portion of said P domain in proximity sufficient for ligation.

* * * * *

UNITED STATES PATENT AND TRADEMARK OFFICE
CERTIFICATE OF CORRECTION

PATENT NO. : 5,683,874

DATED : November 4, 1997

INVENTOR(S) : Eric T. Kool

It is certified that error appears in the above-identified patent and that said Letters Patent is hereby corrected as shown below:

Column 3, line 53: "domain (AP) domain" should read --(AP) domain--

Column 6, line 35: after "14B" delete --middle three curves--

Column 7, line 43: "21." should read --21).--

Column 9, line 35: after "in" insert --a--

Column 15, line 36: "moleties" should read --moieties--

Column 20, line 23: "standard" should read --stranded--

Column 26, line 63: "CUAGAAGGAGAGAGAUGGGUGCGAGAG-3"

should read --CUAGAAGGAGAGAGAUGGGUGCGAGAG-3'--

Column 26, line 66: "5'-AUGGAAAAGGAAGGGAAAAUU-3'"

should read --5'-AUGGAAAAGGAAGGGAAAAUU-3'--

Column 27, line 2: "5'-UUUUAAAAGAAAAGGGGGACUGG-3'"

should read --5'-UUUUAAAAGAAAAGGGGGACUGG-3'--

Column 28, line 22: after "example," delete --by--

UNITED STATES PATENT AND TRADEMARK OFFICE
CERTIFICATE OF CORRECTION

PATENT NO. : 5,683,874

DATED : November 4, 1997

INVENTOR(S) : Eric T. Kool

It is certified that error appears in the above-identified patent and that said Letters Patent is hereby corrected as shown below:

Column 33, line 33: "oliogmers" should read --oligomers--

Column 33, line 44: "kcal)" should read --kcal.--

Column 33, line 64: "Change" should read --change--

Column 35, line 19: "m5C" should read --m$^5$C--

Column 38, line 67: "phorphoramidite" should read --phosphoramidite--

Column 48, line 28: "T," should read --T$_m$--

Signed and Sealed this

Twenty-seventh Day of March, 2001

Attest:

NICHOLAS P. GODICI

Attesting Officer

Acting Director of the United States Patent and Trademark Office

SEQUENCE LISTING ( 1 ) GENERAL INFORMATION:

( i i i ) NUMBER OF SEQUENCES: 44

( 2 ) INFORMATION FOR SEQ ID NO:1:

( i ) SEQUENCE CHARACTERISTICS:
( A ) LENGTH: 34 base pairs
( B ) TYPE: nucleic acid
( C ) STRANDEDNESS: single
( D ) TOPOLOGY: circular ( x i ) SEQUENCE DESCRIPTION: SEQ ID NO:1:

CTCCCCGCCC TCNNNNCTC CCACCCCTCN NNNN    3 4

( 2 ) INFORMATION FOR SEQ ID NO:2:

( i ) SEQUENCE CHARACTERISTICS:
( A ) LENGTH: 38 base pairs
( B ) TYPE: nucleic acid
( C ) STRANDEDNESS: single
( D ) TOPOLOGY: circular ( x i ) SEQUENCE DESCRIPTION: SEQ ID NO:2:

TCTTTTTCT TTTCNNNNNC TTTCTTTTT TCTNNNNN    3 8

( 2 ) INFORMATION FOR SEQ ID NO:3:

( i ) SEQUENCE CHARACTERISTICS:
( A ) LENGTH: 36 base pairs
( B ) TYPE: nucleic acid
( C ) STRANDEDNESS: single
( D ) TOPOLOGY: circular ( x i ) SEQUENCE DESCRIPTION: SEQ ID NO:3:

TCTTCCTCTC TCTATTTATC TCTCCTTC TATCGA    3 6

( 2 ) INFORMATION FOR SEQ ID NO:4:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: circular ( x i ) SEQUENCE DESCRIPTION: SEQ ID NO:4:

```
CTTTTCCTTC CCTTCGATTC CCTTCCTTTT CCCTCC                                    36
```

( 2 ) INFORMATION FOR SEQ ID NO:5:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: both ( x i ) SEQUENCE DESCRIPTION: SEQ ID NO:5:

```
TTTTTTCACA CTTTTTTTT TTTCACACTT TTTT                                       34
```

( 2 ) INFORMATION FOR SEQ ID NO:6:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: both ( x i ) SEQUENCE DESCRIPTION: SEQ ID NO:6:

```
TCTTTCCACA CCTTTCTTTT CTTCACACTT CTTT                                      34
```

( 2 ) INFORMATION FOR SEQ ID NO:7:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: both ( x i ) SEQUENCE DESCRIPTION: SEQ ID NO:7:

```
TTTCTTCACA CTTCTTTTCT TTCCACACCT TTCT                                      34
```

( 2 ) INFORMATION FOR SEQ ID NO:8:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

```
AAAAAAAAA AA                                                               12
```

( 2 ) INFORMATION FOR SEQ ID NO:9:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

```
AAGAAAAGAA AG                                                              12
```

( 2 ) INFORMATION FOR SEQ ID NO:10:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

CTTTCTTTTC TT                                                                                                                                 12

( 2 ) INFORMATION FOR SEQ ID NO:11:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

AAAAAAAAAA AA                                                                                                                12

( 2 ) INFORMATION FOR SEQ ID NO:12:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

AAGAAAGAAA AG                                                                                                              12

( 2 ) INFORMATION FOR SEQ ID NO:13:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

AAGAAAGAAA AG                                                                                                              12

( 2 ) INFORMATION FOR SEQ ID NO:14:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: both ( x i ) SEQUENCE DESCRIPTION: SEQ ID NO:14:

TTCTTCTCTT TCCACACCTT TCTATTCTTC ACAC                                                                     34

( 2 ) INFORMATION FOR SEQ ID NO:15:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:15:

AAAAAAAAAA AA                                                                                                              12

( 2 ) INFORMATION FOR SEQ ID NO:16:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:16:

TCTCTTTTTT TTTTCTCTC TCTTTTTTTT TTTCTC                36

( 2 ) INFORMATION FOR SEQ ID NO:17:

( i ) SEQUENCE CHARACTERISTICS:
    ( A ) LENGTH: 13 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:17:

AAAGAGAGAG AAA                                        13

( 2 ) INFORMATION FOR SEQ ID NO:18:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: circular ( x i ) SEQUENCE DESCRIPTION: SEQ ID NO:18:

TTTTTTTTT CTCTCTCTTT TTTTTTTCT CTCTCT                 36

( 2 ) INFORMATION FOR SEQ ID NO:19:

( i ) SEQUENCE CHARACTERISTICS:
    ( A ) LENGTH: 9 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:19:

AGAGAGAGA                                             9

( 2 ) INFORMATION FOR SEQ ID NO:20:

( i ) SEQUENCE CHARACTERISTICS:
    ( A ) LENGTH: 9 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:20:

AAAAAAAAA                                             9

( 2 ) INFORMATION FOR SEQ ID NO:21:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:21:

CACAAGAGAG AGAATCCCTA AAAAAAAAA CAC                   33

( 2 ) INFORMATION FOR SEQ ID NO:22:

( i ) SEQUENCE CHARACTERISTICS:
    ( A ) LENGTH: 9 base pairs (B) TYPE: nucleic acid
(C) STRANDEDNESS: single
(D) TOPOLOGY: linear (xi) SEQUENCE DESCRIPTION: SEQ ID NO:22:

TCTCTCTCT 9

(2) INFORMATION FOR SEQ ID NO:23:

(i) SEQUENCE CHARACTERISTICS:
(A) LENGTH: 9 base pairs
(B) TYPE: nucleic acid
(C) STRANDEDNESS: single
(D) TOPOLOGY: linear (xi) SEQUENCE DESCRIPTION: SEQ ID NO:23:

TTTTTTTT 9

(2) INFORMATION FOR SEQ ID NO:24:

(i) SEQUENCE CHARACTERISTICS:
(A) LENGTH: 34 base pairs
(B) TYPE: nucleic acid
(C) STRANDEDNESS: single
(D) TOPOLOGY: circular (xi) SEQUENCE DESCRIPTION: SEQ ID NO:24:

UUUUUUUUUU UUCACACUUU UUUUUUUUUC ACAC 34

(2) INFORMATION FOR SEQ ID NO:25:

(i) SEQUENCE CHARACTERISTICS:
(A) LENGTH: 34 base pairs
(B) TYPE: nucleic acid
(C) STRANDEDNESS: single
(D) TOPOLOGY: circular (xi) SEQUENCE DESCRIPTION: SEQ ID NO:25:

UUCUUUCUUU UCCACACCUU UUCUUUCUUC ACAC 34

(2) INFORMATION FOR SEQ ID NO:26:

(i) SEQUENCE CHARACTERISTICS:
(A) LENGTH: 34 base pairs
(B) TYPE: nucleic acid
(C) STRANDEDNESS: single
(D) TOPOLOGY: circular (xi) SEQUENCE DESCRIPTION: SEQ ID NO:26:

TTCTTTCTTT TCCACACCTT TTCTTTCTTC ACAC 34

(2) INFORMATION FOR SEQ ID NO:27:

(i) SEQUENCE CHARACTERISTICS:
(A) LENGTH: 34 base pairs
(B) TYPE: nucleic acid
(C) STRANDEDNESS: single
(D) TOPOLOGY: linear (xi) SEQUENCE DESCRIPTION: SEQ ID NO:27:

UUUCUUCACA CUUCUUUCUU UUCCACACCU UUUC 34

(2) INFORMATION FOR SEQ ID NO:28:

(i) SEQUENCE CHARACTERISTICS:
(A) LENGTH: 12 base pairs
(B) TYPE: nucleic acid
(C) STRANDEDNESS: single ( D ) TOPOLOGY: linear ( x i ) SEQUENCE DESCRIPTION: SEQ ID NO:28:

GAAAAGAAAG AA 12

( 2 ) INFORMATION FOR SEQ ID NO:29:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

GAAAAGAAAG AA 12

( 2 ) INFORMATION FOR SEQ ID NO:30:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

CUUUUCUUUC UU 12

( 2 ) INFORMATION FOR SEQ ID NO:31:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: circular ( x i ) SEQUENCE DESCRIPTION: SEQ ID NO:31:

TTCTTTCTTT TC 12

( 2 ) INFORMATION FOR SEQ ID NO:32:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

AGAGAGAAGA GG 12

( 2 ) INFORMATION FOR SEQ ID NO:33:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: circular ( x i ) SEQUENCE DESCRIPTION: SEQ ID NO:33:

TCTCTCTTCT CC 12

( 2 ) INFORMATION FOR SEQ ID NO:34:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

ATAAGGAAGA AG    12

( 2 ) INFORMATION FOR SEQ ID NO:35:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: circular ( x i ) SEQUENCE DESCRIPTION: SEQ ID NO:35:

TATTCCTTCT TC    12

( 2 ) INFORMATION FOR SEQ ID NO:36:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: circular ( x i ) SEQUENCE DESCRIPTION: SEQ ID NO:36:

TCTCTCTTCT CCNNNNNCCT CTTCTCTCTN NNNN    34

( 2 ) INFORMATION FOR SEQ ID NO:37:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: circular ( x i ) SEQUENCE DESCRIPTION: SEQ ID NO:37:

TGTTCCTTCT TCNNNNNCTT CTTCCTTATN NNNN    34

( 2 ) INFORMATION FOR SEQ ID NO:38:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:38:

AAGANAAGAA AG    12

( 2 ) INFORMATION FOR SEQ ID NO:39:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:39:

AAGAAAANAA AG    12

( 2 ) INFORMATION FOR SEQ ID NO:40:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:40:

GGACTCTATC AGAAGAAAAG AAAGGGACTC TATCAG    36

( 2 ) INFORMATION FOR SEQ ID NO:41:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: circular ( x i ) SEQUENCE DESCRIPTION: SEQ ID NO:41:

TTTTCTTTTC CCCTTTCCCC TTTTCTTTTA TCGA    34

( 2 ) INFORMATION FOR SEQ ID NO:42:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:42:

CUAGAAGGAG AGAGAUGGGU GCGAGAG    27

( 2 ) INFORMATION FOR SEQ ID NO:43:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:43:

AUGGAAAAGG AAGGGAAAAU U    21

( 2 ) INFORMATION FOR SEQ ID NO:44:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:44:

UUUUAAAAGA AAAGGGGGGA CUGG    24